US012618115B2

(12) United States Patent (10) Patent No.: US 12,618,115 B2
Lau et al. (45) Date of Patent: May 5, 2026

(54) DETERMINATION OF CYTOTOXIC GENE SIGNATURE AND ASSOCIATED SYSTEMS AND METHODS FOR RESPONSE PREDICTION AND TREATMENT

(71) Applicant: Tempus AI, Inc., Chicago, IL (US)

(72) Inventors: Denise Lau, Chicago, IL (US); Aly A. Khan, Chicago, IL (US); Yinjie Gao, Los Angeles, CA (US); Michelle Marie Stein, Chicago, IL (US); Ameen Salahudeen, Oak Park, IL (US); Timothy Rand, Chicago, IL (US); Sonal Khare, Chicago, IL (US)

(73) Assignee: Tempus AI, Inc., Chicago, IL (US)

( * ) Notice: Subject to any disclaimer, the term of this patent is extended or adjusted under 35 U.S.C. 154(b) by 0 days.

(21) Appl. No.: 17/455,876

(22) Filed: Nov. 19, 2021

(65) Prior Publication Data

US 2022/0154284 A1 May 19, 2022

Related U.S. Application Data

(60) Provisional application No. 63/260,259, filed on Aug. 13, 2021, provisional application No. 63/176,100, filed on Apr. 16, 2021, provisional application No. 63/165,004, filed on Mar. 23, 2021, provisional application No. 63/115,760, filed on Nov. 19, 2020.

(51) Int. Cl.
*C12Q 1/6886* (2018.01)
*C12Q 1/6869* (2018.01)
*G16B 25/10* (2019.01)
*G16B 30/00* (2019.01)
*G16H 50/20* (2018.01)

(52) U.S. Cl.
CPC ......... *C12Q 1/6886* (2013.01); *C12Q 1/6869* (2013.01); *G16B 25/10* (2019.02); *G16H 50/20* (2018.01); *C12Q 2600/112* (2013.01); *G16B 30/00* (2019.02)

(58) Field of Classification Search
CPC ......... G16H 50/20; G16B 25/10; G16B 30/00
See application file for complete search history.

(56) References Cited

U.S. PATENT DOCUMENTS

| | | | |
|---|---|---|---|
| 10,395,772 B1 | 8/2019 | Lucas et al. | |
| 10,902,952 B2 | 1/2021 | Lucas et al. | |
| 10,957,041 B2 | 3/2021 | Yip et al. | |
| 10,975,445 B2 | 4/2021 | Venkat et al. | |
| 11,043,283 B1 | 6/2021 | Bell et al. | |
| 11,043,304 B2 | 6/2021 | Lozac'hmeur et al. | |
| 11,081,210 B2 | 8/2021 | Perera | |
| 11,145,416 B1 | 10/2021 | Hafez et al. | |
| 2017/0306416 A1 | 10/2017 | Bedoya et al. | |
| 2018/0363066 A1 | 12/2018 | Chalmers et al. | |
| 2020/0075169 A1 | 3/2020 | Lau et al. | |

| | | |
|---|---|---|
| 2020/0098448 A1 | 3/2020 | Shah et al. |
| 2020/0118644 A1 | 4/2020 | Khan et al. |
| 2020/0135303 A1 | 4/2020 | Barber |
| 2020/0157633 A1 | 5/2020 | Regev et al. |
| 2020/0210852 A1 | 7/2020 | Igartua et al. |
| 2020/0211716 A1 | 7/2020 | Lefkofsky et al. |
| 2020/0258601 A1 | 8/2020 | Lau |
| 2020/0335102 A1 | 10/2020 | Lefkofsky et al. |
| 2020/0365232 A1 | 11/2020 | Jaros et al. |
| 2020/0365268 A1 | 11/2020 | Michuda et al. |
| 2020/0381087 A1 | 12/2020 | Ozeran et al. |
| 2020/0395097 A1 | 12/2020 | Chang et al. |
| 2021/0057042 A1 | 2/2021 | Beaubier et al. |
| 2021/0057071 A1 | 2/2021 | Barber et al. |
| 2021/0090694 A1 | 3/2021 | Colley et al. |
| 2021/0098078 A1 | 4/2021 | Lozac'hmeur et al. |
| 2021/0115511 A1 | 4/2021 | Blidner |
| 2021/0118526 A1 | 4/2021 | Barber |
| 2021/0118559 A1 | 4/2021 | Lefkofsky |
| 2021/0151192 A1 | 5/2021 | Lucas et al. |
| 2021/0155989 A1 | 5/2021 | Salahudeen et al. |
| 2021/0172931 A1 | 6/2021 | Larsen et al. |

(Continued)

FOREIGN PATENT DOCUMENTS

| | | |
|---|---|---|
| WO | 2016109546 A2 | 7/2016 |
| WO | 2018231762 A1 | 12/2018 |

(Continued)

OTHER PUBLICATIONS

Heeke et al., Tumor mutational burden assessment as a predictive biomarker for immunotherapy in lung cancer patients: getting ready for prime-time or not, 2018, Trans Lung Cancer Res, 7(6), p. 631-638 (Year: 2018).*
Ballot et al., Tumor Infiltrating Lymphocytes Signature as a New Pan-Cancer Predictive Biomarker of Anti PD-1/PD-L1 Efficacy, 2020, Cancers, 12(2418), p. 1-15 (Year: 2020).*
Lee et al., Multiomics Prediction of Response Rates to Therapies to Inhibit Programmed Cell Death 1 and Programmed Cell Death 1 Ligand 1, 2019, JAMA Oncol., 5(11), p. 1614-1618 (Year: 2019).*
Newman et al., Robust enumeration of cell subsets from tissue expression profiles, 2015, 12(5), Nature Methods, 12(5), p. 453-457 (Year: 2015).*
Tian et al., A novel tumor mutational burden estimation model as a predictive and prognostic biomarker in NSCLC patients, 2020, BMC Medicine, 18:232, p. 1-11 (Year: 2020).*

(Continued)

*Primary Examiner* — Kaitlyn L Minchella
(74) *Attorney, Agent, or Firm* — Quarles & Brady LLP

(57) ABSTRACT

Disclosed herein are systems, methods, and compositions for treating a subject diagnosed with, or suffering from cancer. In some embodiments, the method comprises determining whether a tumor sample from the subject includes a cytotoxic gene signature, and treating the subject based on the determination. In some embodiments, the subject has or is suspected of having a loss of heterozygosity in human leukocyte antigen (HLA) class I genes. In some embodiments, the therapy comprises one or more checkpoint inhibitors. In some embodiments, the cancer is colorectal, uterine, stomach, lung, skin, head or neck, or non-small cell lung carcinoma.

14 Claims, 37 Drawing Sheets
(29 of 37 Drawing Sheet(s) Filed in Color)

(56) References Cited

U.S. PATENT DOCUMENTS

| | | | |
|---|---|---|---|
| 2021/0257047 A1 | 8/2021 | Zhu et al. |
| 2021/0257055 A1 | 8/2021 | Finkle et al. |
| 2021/0269878 A1 | 9/2021 | Blidner |
| 2021/0325308 A1 | 10/2021 | Kannan et al. |
| 2021/0343372 A1 | 11/2021 | Tell et al. |
| 2021/0355533 A1 | 11/2021 | Perera et al. |
| 2021/0398617 A1 | 12/2021 | Finkle et al. |
| 2022/0059190 A1 | 2/2022 | Ahmed et al. |

FOREIGN PATENT DOCUMENTS

| | | |
|---|---|---|
| WO | 2019070755 A1 | 4/2019 |
| WO | 2019204338 A1 | 10/2019 |
| WO | 2021081253 A1 | 4/2021 |
| WO | 2021168143 A1 | 8/2021 |

OTHER PUBLICATIONS

Zuo et al., A robust six-gene prognostic signature for prediction of both disease-free and overall survival in non-small cell lung cancer, May 14, 2019, Journal of Translational Medicine, 17(152), p. 1-16). (Year: 2019).*

Guo et al., Global characterization of T cells in non-small-cell lung cancer by single-cell sequencing, 2018, Nature Medicine, p. 978-985 (Year: 2018).*

Takeuchi et al., CRTAM Confers Late-Stage Activation of CD8+ T Cells to Regulate Retention within Lymph Node, Journal of Immunology, 2009, 183(7):4220-4228.

Takeuchi et al., CRTAM Determines the CD4+ Cytotoxic T Lymphocyte Lineage, Journal of Experimental Medicine, 2016, 213(1):123-138.

Takeuchi et al., CD4 CTL, a Cytotoxic Subset of CD4+ T Cells, Their Differentiation and Function, Frontiers in Immunology, 2017, vol. 8, Article 194, pp. 1-7.

Tan et al., Overview of Multiplex Immunohistochemistry/Immunofluorescence Techniques in the Era of Cancer Immunotherapy, Cancer Communications, 2020, 40(4):135-153.

Tay et al., Revisiting the Role of CD4+ T Cells in Cancer Immunotherapy—New Insights Into Old Paradigms, Cancer Gene Therapy, 2021, 28(1):5-17.

Thommen et al., A Transcriptionally and Functionally Distinct PD-1+ CD8+ T Cell Pool with Predictive Potential in Non-Small-Cell Lung Cancer Treated with PD-1 Blockade, Nature Medicine, 2018, 24(7):994-1004.

Tirosh et al., Dissecting the Multicellular Ecosystem of Metastatic Melanoma by Single-Cell RNA-seq, Science, 2016, 352(6282):189-196.

Voskoboinik et al., Perforin and Granzymes: Function, Dysfunction and Human Pathology, Nature Reviews Immunology, 2015, 15(6):388-400.

Wolf et al., SCANPY: Large-Scale Single-Cell Gene Expression Data Analysis, Genome Biology, 2018, 19:15, pp. 1-5.

Wolock et al., Scrublet: Computational Identification of Cell Doublets in Single-Cell Transcriptomic Data, Cell Systems, 2019, 8(4):281-291.

Wosen et al., Epithelial MHC Class II Expression and Its Role in Antigen Presentation in the Gastrointestinal and Respiratory Tracts, Frontiers in Immunology, 2018, vol. 9, Article 2144, pp. 1-14.

Xie et al., Naive Tumor-Specific CD4+ T Cells Differentiated In Vivo Eradicate Established Melanoma, Journal of Experimental Medicine, 2010, 207(3):651-667.

Zaretsky et al., Mutations Associated with Acquired Resistance to PD-1 Blockade in Melanoma, New England Journal of Medicine, 2016, 375(9):819-829.

Zhang et al., Lineage Tracking Reveals Dynamic Relationships of T Cells in Colorectal Cancer, Nature, 2018, 564:268-272.

Zheng et al., Landscape of Infiltrating T Cells in Liver Cancer Revealed by Single-Cell Sequencing, Cell, 2017, 169:1342-1356.

PCT International Search Report and Written Opinion, PCT/US2021/072529, May 13, 2022, 17 pages.

Anagnostou et al., Multimodal Genomic Features Predict Outcome of Immune Checkpoint Blockade in Non-Small-Cell Lung Cancer, Nature Cancer, 2020, 1(1):99-111.

Auslander et al., Robust Prediction of Response to Immune Checkpoint Blockade Therapy in Metastatic Melanoma, Nature Medicine, 2018, 24(10):1545-1549.

Axelrod et al., Biological Consequences of Major Histocompatibility Class-II Expression by Tumor Cells in Cancer, Clinical Cancer Research, 2019, 25(8):2392-2402.

Ayers et al., IFN-γ-Related mRNA Profile Predicts Clinical Response to PD-1 Blockade, Journal of Clinical Investigation, 2017, 127(8):2930-2940.

Beaubier et al., Clinical Validation of the Tempus xO Assay, Oncotarget, 2018, 9(40):25826-25832.

Beaubier et al., Clinical Validation of the Tempus xT Next-Generation Targeted Oncology Sequencing Assay, Oncotarget, 2019, 10(24):2384-2396.

Berrih et al., Interferon-gamma Modulates HLA Class II Antigen Expression on Cultured Human Thymic Epithelial Cells, Journal of Immunology, 1985, 135(2):1165-1171.

Boles et al., The Tumor Suppressor TSLC1/NECL-2 Triggers NK-cell and CD8+ T-cell Responses through the Cell-Surface Receptor CRTAM, Blood, 2005, 106(3):779-786.

Borst et al., CD4+ T Cell Help in Cancer Immunology and Immunotherapy, Nature Reviews Immunology, 2018, 18(10):635-647.

Bray et al., Near-Optimal Probabilistic RNA-seq Quantification, Nature Biotechnology, 2016, 34(5):525-527.

Castro et al., Elevated Neoantigen Levels in Tumors with Somatic Mutations in the HLA-A, HLA-B, HLA-C and B2M Genes, BMC Medical Genomics, 2019, 12(Suppl 6):107, 13 pages.

Chowell et al., Patient HLA Class I Genotype Influences Cancer Response to Checkpoint Blockade Immunotherapy, Science, 2018, 359(6375):582-587.

Cristescu et al., Pan-Tumor Genomic Biomarkers for PD-1 Checkpoint Blockade-Based Immunotherapy, Science, 2018, 362(6411):eaar3593, 27 pages.

Crosby et al., Immunohistochemistry Protocol for Parraffin-Embedded Tissue Sections—Adevertisment, JoVE, 2014, doi:10.3791/5064, 13 pages.

Damotte et al., The Tumor Inflammation Signature (TIS) is Associated with anti-PD-1 Treatment Benefit in the CERTIM Pan-Cancer Cohort, Journal of Translational Medicine, 2019, 17:357, 10 pages.

Darby et al., scHLAcount: Allele-Specific HLA Expression from Single-Cell Gene Expression Data, Bioinformatics, 2020, 36(12):3905-3906.

Duhen et al., Co-Expression of CD39 and CD103 Identifies Tumor-Reactive CD8 T Cells in Human Solid Tumors, Nature Communications, 2018, 9:2724, pp. 1-13.

Durante et al., Single-Cell Analysis Reveals New Evolutionary Complexity in Uveal Melanoma, Nature Communications, 2020, 11:496, pp. 1-10.

Franciszkiewicz et al., Intratumoral Induction of CD103 Triggers Tumor-Specific CTL Function and CCR5-Dependent T-cell Retention, Cancer Research, 2009, 69(15):6249-6255.

Garon et al., Five-Year Overall Survival for Patients with Advanced Non-Small-Cell Lung Cancer Treated with Pembrolizumab: Results from the Phase I KEYNOTE-001 Study, Journal of Clinical Oncology, 2019, 37(28):2518-2527.

Gettinger et al., Impaired HLA Class I Antigen Processing and Presentation as a Mechanism of Acquired Resistance to Immune Checkpoint Inhibitors in Lung Cancer, Cancer Discovery, 2017, 7(12):1420-1435.

Griffith et al., Characterizing the Feasibility and Performance of Real-World Tumor Progression End Points and Their Association with Overall Survival in a Large Advanced Non-Small-Cell Lung Cancer Data Set, JCO Clinical Cancer Informatics, 2019, 3:1-13.

Guo et al., Global Characterization of T Cells in Non-Small-Cell Lung Cancer by Single-Cell Sequencing, Nature Medicine, 2018, 24:978-985.

(56)        References Cited

OTHER PUBLICATIONS

He et al., MHC Class II Expression in Lung Cancer, Lung Cancer, 2017, 112:75-80.

Huang et al., A Single Dose of Neoadjuvant PD-1 Blockade Predicts Clinical Outcomes in Resectable Melanoma, Nature Medicine, 2019, 25(3):454-461.

Jiang et al., Signatures of T Cell Dysfunction and Exclusion Predict Cancer Immunotherapy Response, Nature Medicine, 2018, 24(10):1550-1558.

Kamma et al., Expression of MHC Class II Antigens in Human Lung Cancer Cells, Virchows Archiv B Cell Pathol, 1991, 60(6):407-412.

Litchfield et al., Meta-Analysis of Tumor- and T Cell-Intrinsic Mechanisms of Sensitization to Checkpoint Inhibition, Cell, 2021, 184(3):596-614.

Liu et al., Identification of FABP5 as an Immunometabolic Marker in Human Hepatocellular Carcinoma, Journal for Immunotherapy of Cancer, 2020, 8:e000501, pp. 1-12.

Martinez et al., Immunotherapy for the First-Line Treatment of Patients with Metastatic Non-Small Cell Lung Cancer, Clinical Cancer Research, 2019, 25(9):2691-2698.

McGranahan et al, Allele-Specific HLA Loss and Immune Escape in Lung Cancer Evolution, Cell, 2017, 171(6):1259-1271.

Middha et al., Majority of B2M-Mutant and -Deficient Colorectal Carcinomas Achieve Clinical Benefit From Immune Checkpoint Inhibitor Therapy and Are Microsatellite Instability-High, JCO Precision Oncology, 2019, 3:1-14.

Neuwelt et al., Cancer Cell-Intrinsic Expression of MHC II in Lung Cancer Cell Lines is Actively Restricted by MEK/ERK Signaling and Epigenetic Mechanisms, Journal for Immunotherapy of Cancer, 2020, 8(1):e000441, pp. 1-12.

Nieto et al., A Single-Cell Tumor Immune Atlas for Precision Oncology, Genome Research, 2021, 31(10):1913-1926.

Oh et al., Intratumoral CD4+ T Cells Mediate Anti-Tumor Cytotoxicity in Human Bladder Cancer, Cell, 2020, 181:1612-1625.

Orenbuch et al., arcasHLA: High-Resolution HLA Typing from RNAseq, Bioinformatics, 2020, 36(1):33-40.

Polanski et al., BBKNN: Fast Batch Alignment of Single Cell Transcriptomes, Bioinformatics, 2020, 36(3):964-965.

Polsterl, scikit-survival: A Library for Time-to-Event Analysis Built on Top of scikit-learn, Journal of Machine Learning Research, 2020, 21(212):1-6.

Prat et al., Immune-Related Gene Expression Profiling After PD-1 Blockade in Non-Small Cell Lung Carcinoma, Head and Neck Squamous Cell Carcinoma, and Melanoma, Cancer Research, 2017, 77(13):3540-3550.

Quezada et al., Tumor-Reactive CD4+ T Cells Develop Cytotoxic Activity and Eradicate Large Established Melanoma After Transfer Into Lymphopenic Hosts, Journal of Experimental Medicine, 2010, 207(3):637-650.

Rodig et al., MHC Proteins Confer Differential Sensitivity to CTLA-4 and PD-1 Blockade in Untreated Metastatic Melanoma, Science Translational Medicine, 2018, 10:eaar3342, pp. 1-13.

Roh et al., Integrated Molecular Analysis of Tumor Biopsies on Sequential CTLA-4 and PD-1 Blockade Reveals Markers of Response and Resistance, Science Translational Medicine, 2017, 9(379), 24 pages.

Rooney et al., Molecular and Genetic Properties of Tumors Associated with Local Immune Cytolytic Activity, Cell, 2015, 160(1-2):48-61.

Sade-Feldman et al., Resistance to Checkpoint Blockade Therapy Through Inactivation of Antigen Presentation, Nature Communications, 2017, 8:1136, pp. 1-11.

Shim et al., HLA-Corrected Tumor Mutation Burden and Homologous Recombination Deficiency for the Prediction of Response to PD-(L) 1 Blockade in Advanced Non-Small-Cell Lung Cancer Patients, Annals of Oncology, 2020, 31(7):902-911.

Singh et al., CD4+ Follicular Helper-Like T Cells are Key Players in Anti-Tumor Immunity, bioRxiv 2020.01.08.898346, 2020, 42 pages.

Sledzinska et al., Regulatory T Cells Restrain Interleukin-2-and Blimp-1-Dependent Acquisition of Cytotoxic Function by CD4+ T Cells, Immunity, 2020, 52(1):151-166.

Stoeckius et al., Large-Scale Simultaneous Measurement of Epitopes and Transcriptomes in Single Cells, Nature Methods, 2017, 14(9):865-868.

Sturm et al., Scirpy: A Scanpy Extension for Analyzing Single-cell T-cell Receptor-sequencing Data, Bioinformatics, 2020, 36(18):4817-4818.

Szolek et al., OptiType: Precision HLA Typing from Next-Generation Sequencing Data, Bioinformatics, 2014, 30(23):3310-3316.

European Patent Office, Extended Search Report, Application No. 21895899.9, Sep. 3, 2024, 10 pages.

* cited by examiner

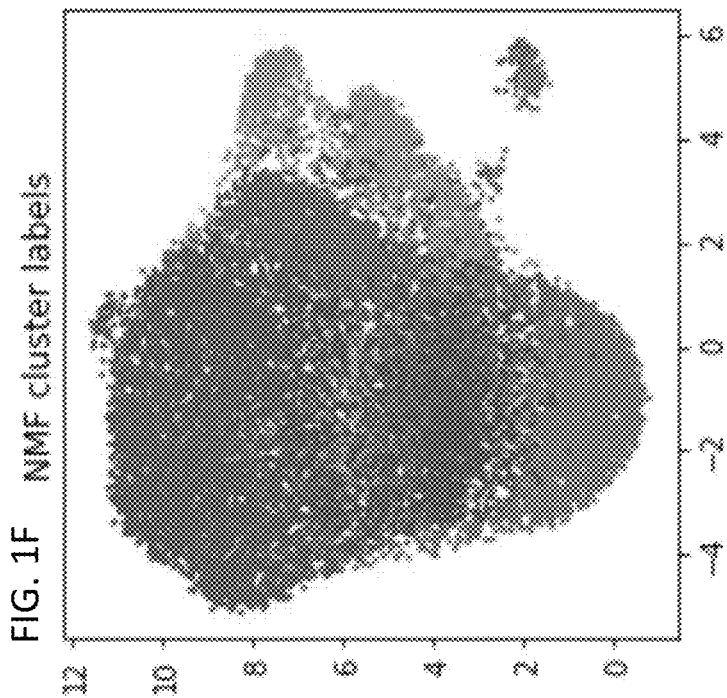
FIG. 1F NMF cluster labels

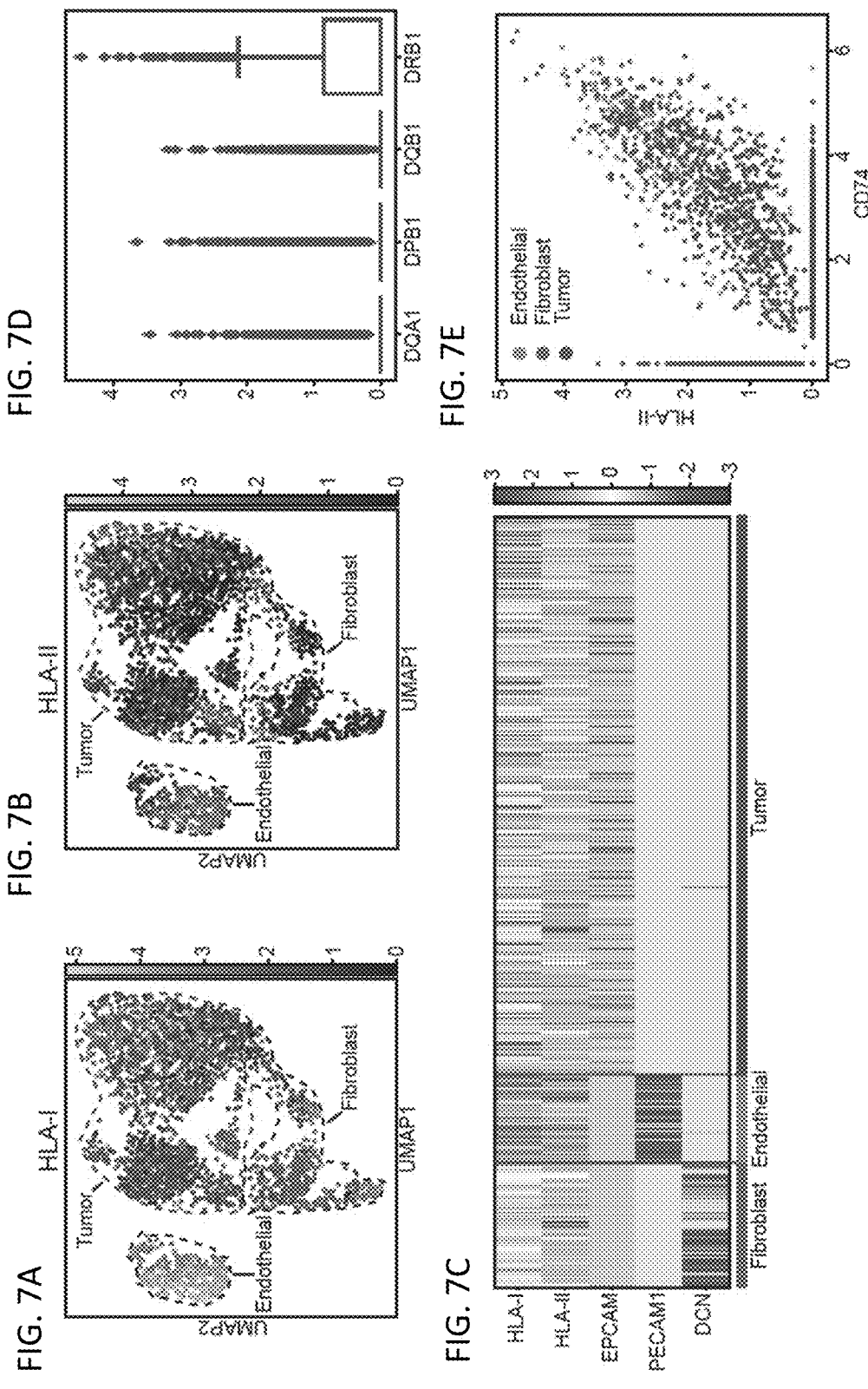

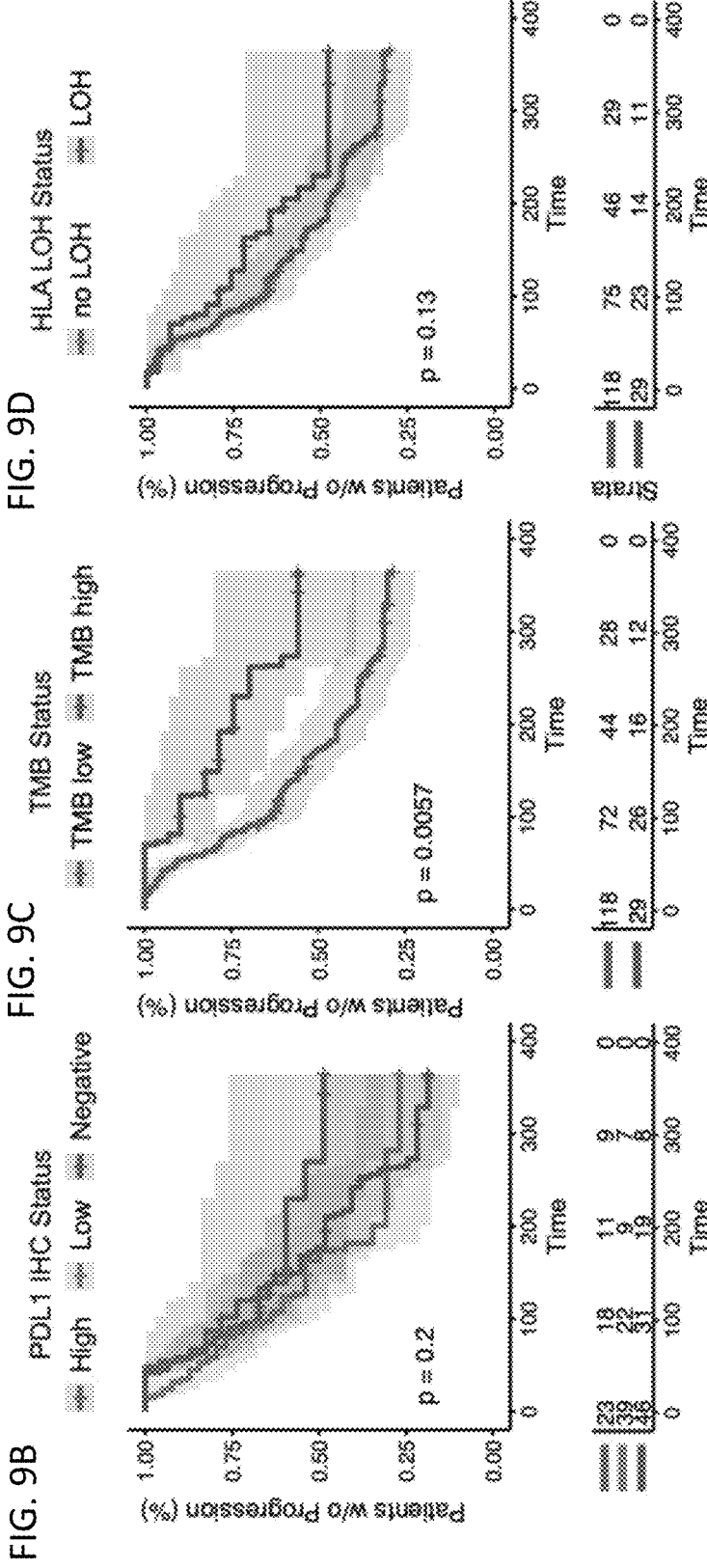

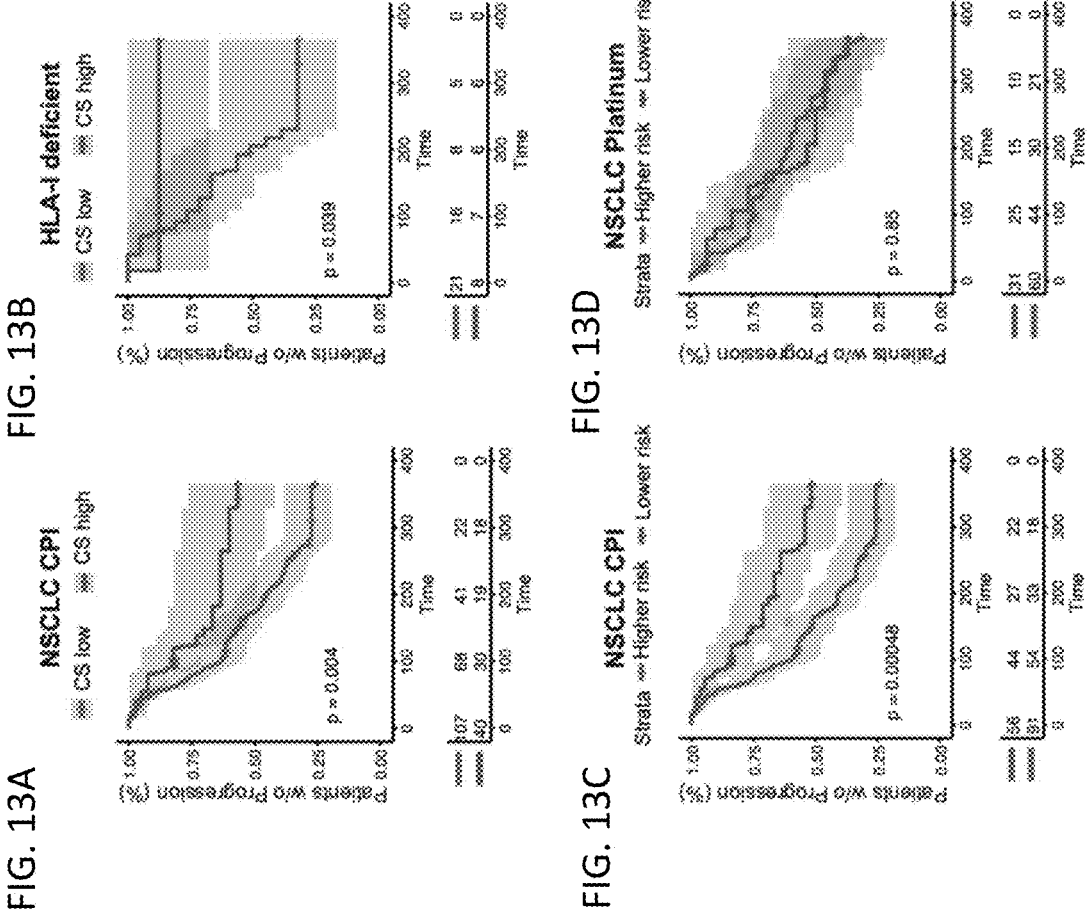

FIG. 17A

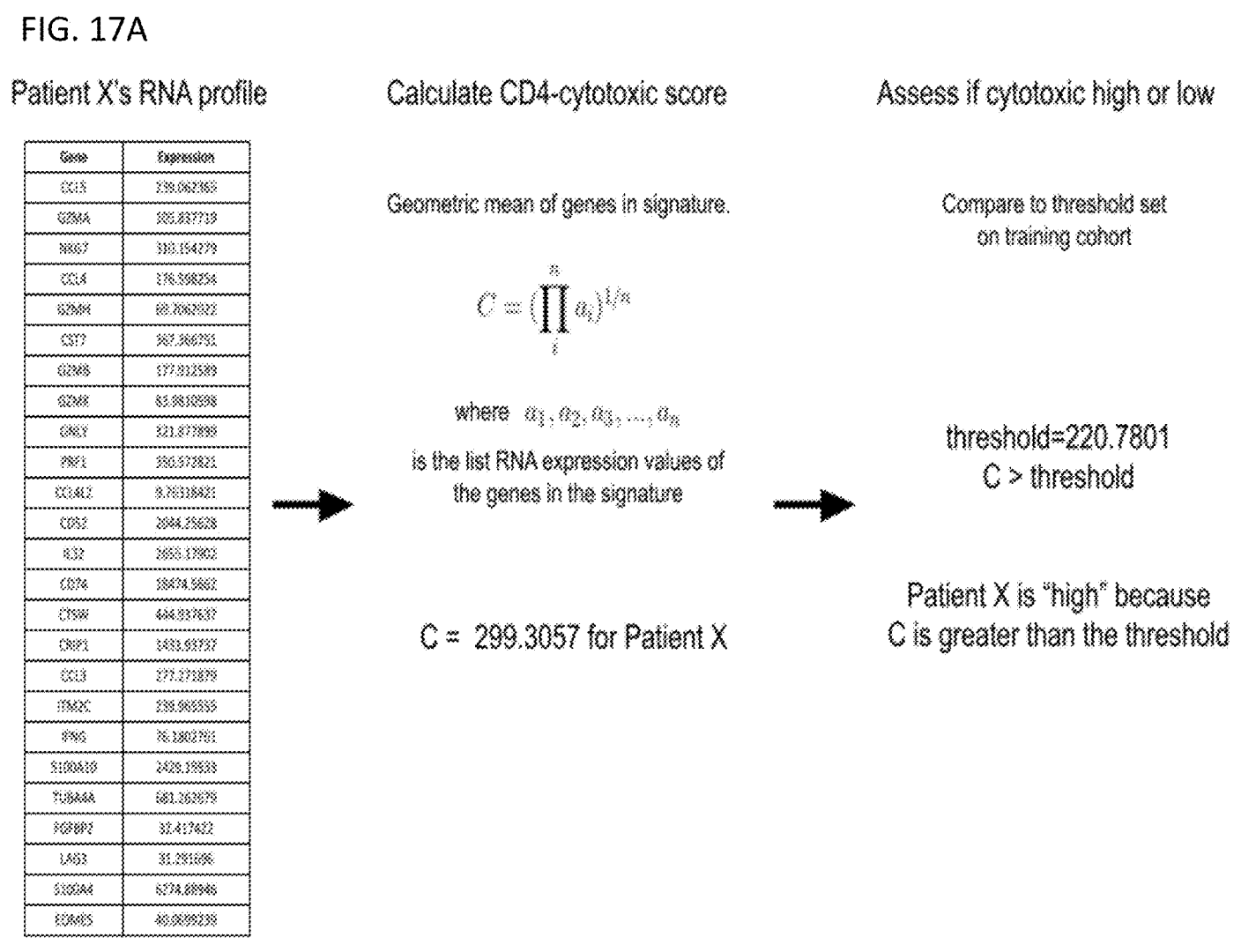

Patient X's RNA profile

| Gene | Expression |
|------|-----------|
| CCL5 | 236.0662362 |
| CD8A | 385.2637719 |
| NKG7 | 581.5654219 |
| CCL4 | 276.596854 |
| GZMA | 565.8962322 |
| CST7 | 562.386751 |
| GZMK | 63.8653638 |
| CD8B | 531.877898 |
| PRF1 | 856.370883 |
| CCL4L2 | 9.76318601 |
| CD3D | 2684.25628 |
| KLRD1 | 3863.17903 |
| CD3G | 3874.5882 |
| CTSW | 434.997637 |
| GNLY | 686.66797 |
| CCL3 | 277.273679 |
| PRKCB | 236.66565 |
| IFNG | 56.3802761 |
| SLC9A3R1 | 2498.50563 |
| TNFAIP3 | 563.365679 |
| KLRK1 | 52.497422 |
| LAG3 | 51.815696 |
| SLC36A4 | 627A.86946 |
| GZMH | 40.0099439 |

Calculate CD4-cytotoxic score

Geometric mean of genes in signature.

$$C = \left( \prod_i^n a_{ij} \right)^{1/n}$$

where $a_{i1}, a_{i2}, a_{i3}, \ldots, a_{in}$ is the list RNA expression values of
the genes in the signature C = 299.3057 for Patient X

Assess if cytotoxic high or low

Compare to threshold set
on training cohort threshold=220.7801
C > threshold

Patient X is "high" because
C is greater than the threshold

Distribution of Score in Training Set

FIG. 20

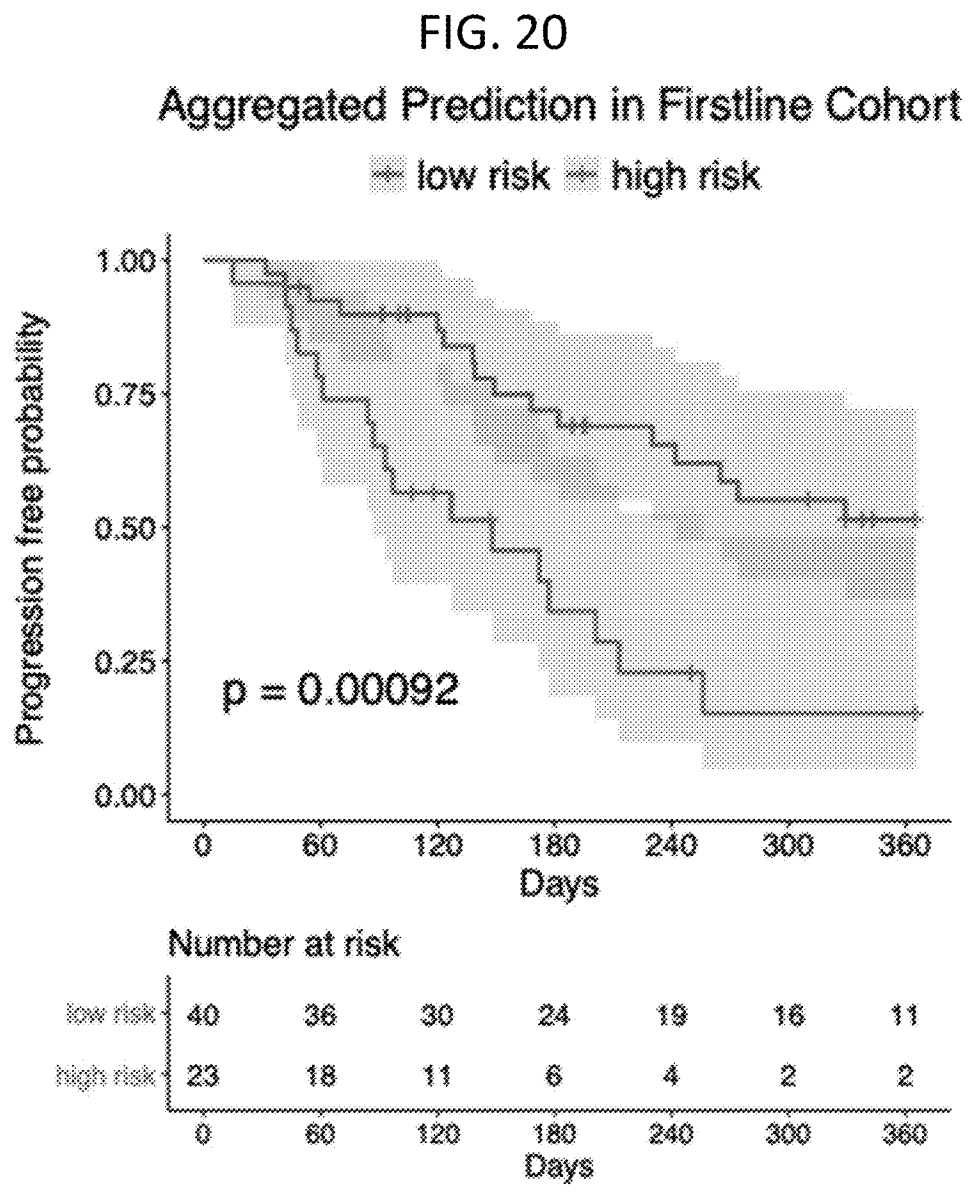

Aggregated Prediction in Firstline Cohort low risk — high risk p = 0.00092

Progression free probability 1.00   0.75   0.50   0.25   0.00

Days 0   60   120   180   240   300   360

Number at risk

| | 0 | 60 | 120 | 180 | 240 | 300 | 360 |
|---|---|---|---|---|---|---|---|
| low risk | 40 | 36 | 30 | 24 | 19 | 16 | 11 |
| high risk | 23 | 18 | 11 | 6 | 4 | 2 | 2 |

Days

FIG. 21 coxPH model HR over folds

FIG. 22

Model Prediction Stability

FIG. 24

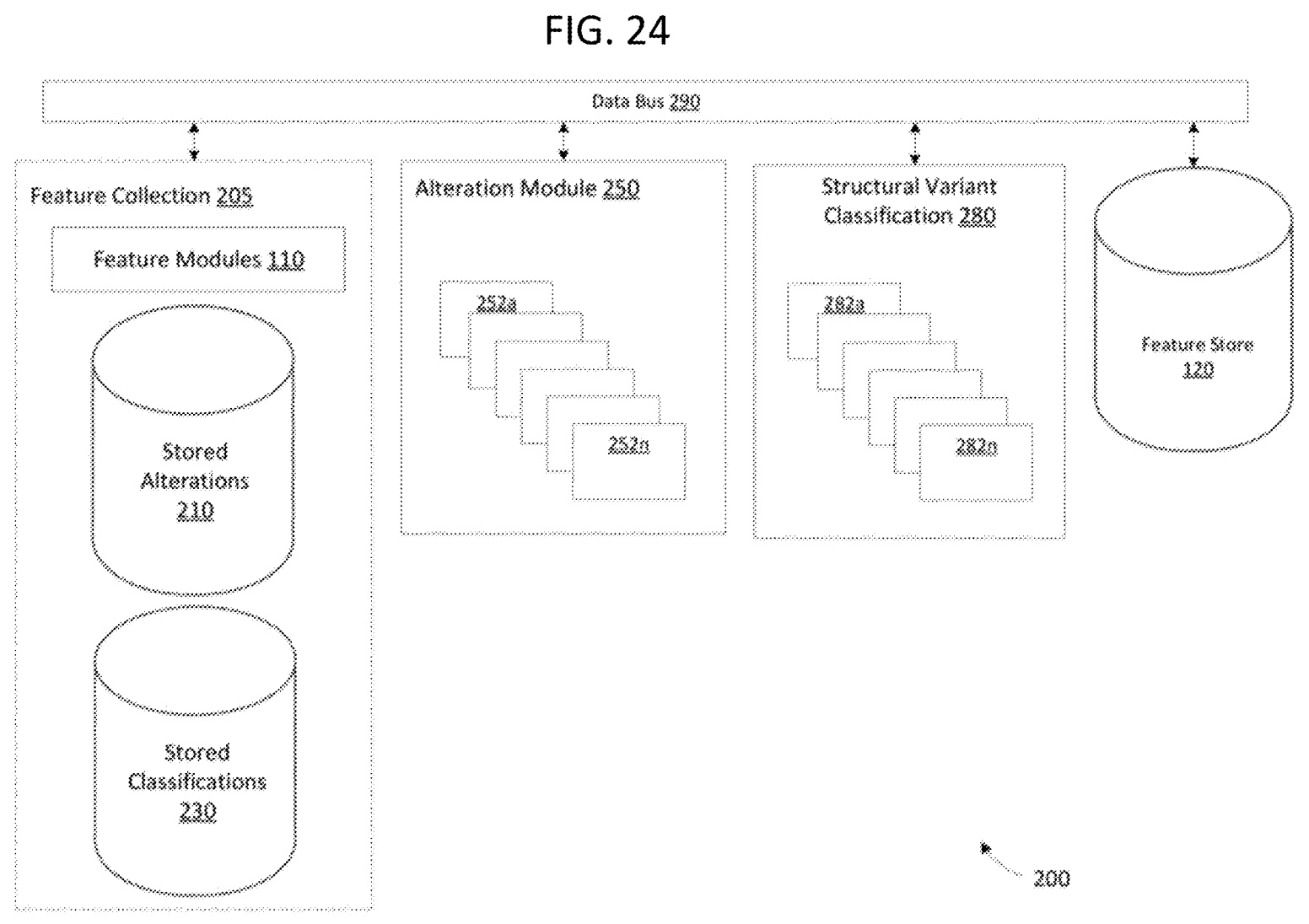

Data Bus 290

Feature Store 120

Structural Variant Classification 280

282a

282n

Alteration Module 250

252a

252n

Feature Collection 205

Feature Modules 110

Stored Alterations 210

Stored Classifications 230

200

DETERMINATION OF CYTOTOXIC GENE SIGNATURE AND ASSOCIATED SYSTEMS AND METHODS FOR RESPONSE PREDICTION AND TREATMENT

CROSS-REFERENCE TO RELATED APPLICATIONS

This application claims the benefit of priority under 35 U.S.C. § 119(e) of U.S. Provisional Application No. 63/115,760, filed Nov. 19, 2020, U.S. Provisional Application No. 63/165,004, filed Mar. 23, 2021, U.S. Provisional Application No. 63/176,100, filed Apr. 16, 2021, and U.S. Provisional Application No. 63/260,259, filed Aug. 13, 2021. The content of each of the above-listed applications is incorporated herein by reference in its entirety.

BACKGROUND

CD8+ T-cells kill tumor cells upon recognizing antigens presented on Human Leukocyte Antigen (HLA) class I molecules (HLA-I). HLA-I proteins are expressed on the surface of all nucleated cells and are vital for immune surveillance. When tumor-specific proteins (neoantigens) are presented on HLA molecules, CD8+ T cell recognition can drive immune responses against the tumor and lead to tumor destruction.

CD8+ T-cells express T-cell receptors (TCRs) that can recognize a specific antigen. An antigen is a molecule capable of stimulating an immune response. For example, the immune system can recognize antigens produced by pathogens and cancer cells. Antigens inside a tumor cell are bound to HLA-I, and brought to the surface of the cell, where they can be recognized by the CD8+ T-cell. If the TCR is specific for that antigen, it binds to both the antigen and to the complex of the class I MHC molecule, and the T cell destroys the tumor cell.

Mechanisms used by CD8+ cells to destroy tumor cells are known in the art. For example, CD8+ cells express molecules such as perforin, which perforates a target tumor cell, and granzymes, a family of serine protease that induce programmed cell death in the tumor cell.

Over time, CD8+ T-cells can become exhausted due to prolonged antigen stimulation and upregulate inhibitory checkpoint molecules. Checkpoint inhibitor therapies can rejuvenate an exhausted CD8+ T-cell population by blocking these inhibitory molecules so that the CD8+ T cells can continue to target tumor cells.

As described above, HLA-I expression is required for effective CD8+ T cell recognition. One common mechanism by which tumor cells evade the immune system is loss of heterozygosity in HLA genes (HLA-LOH) (4, see paragraph [0370]). A retrospective study has shown that patients with partial or complete loss of the HLA-I locus have worse overall survival when treated with immune checkpoint blockade regimens (5). However, some patients with defective class I antigen presentation still have durable responses to immune checkpoint blockade (ICB), suggesting that a non-class I restricted mechanism of anti-tumor immunity also exists.

CD4+ T cells interact with HLA class II molecules (HLA-II) rather than with HLA-I. While HLA-II is normally expressed only on professional antigen-presenting cells such as dendritic cells, mononuclear phagocytes, and B cells, expression on tumor cells has also been documented (12). Tumor expression of HLA-II allows CD4+ T cells to recognize and potentially kill tumor cells. Concordantly, a handful of studies have shown that CD4+ T cells can mediate direct killing of tumor cells (1,2,3), including one early study that showed that CD4+ T cells alone are sufficient to reject a tumor in a mouse model of melanoma (1).

Checkpoint inhibitor use has now become standard of care in several indications, including metastatic NSCLC. Currently, there are only two biomarkers being used in the clinic to prescribe immuno-oncology (IO) therapies (including checkpoint inhibitors): PD-L1 protein level (often measured by expensive, time-consuming immunohistochemical staining methods) and tumor mutational burden (TMB). However, each of these biomarkers has disadvantages. For example, PD-L1 level is not always predictive of patient response to IO, and TMB is only currently approved for prescribing IO therapy to patients on the last line of therapy. Thus, there is an unmet need for diagnostics, biomarkers, and/or tools that complement these methods and aid in clinical decision making, for example, to inform physician management of IO therapy courses (see Haslam and Prasad, JAMA Net Open 2018).

SUMMARY

Disclosed herein are systems, methods, and compositions for treating a subject diagnosed with, or suffering from cancer.

In one aspect of the current disclosure, methods for predicting response to checkpoint inhibitor in a subject suffering from cancer are provided. In some embodiments, the method comprises: at a computer system having one or more processors, and memory storing one or more programs for execution by the one or more processors: (A) obtaining, in electronic format, a plurality of sequence reads, wherein the plurality of sequence reads is obtained for a plurality of nucleic acid molecules from a sample of the cancer obtained from the subject; (B) determining, from the plurality of sequence reads, a plurality of data elements for the subject's cancer comprising: (i) a first set of nucleic acid sequence reads comprising RNA sequence features comprising expression levels of a plurality of at least 9 signature genes selected from Table 1, in the sample of the cancer obtained from the subject, wherein the plurality of signature genes comprises at least CCL5, granzyme A, NKG7, CCL4, granzyme B, granzyme H, granulysin, and perforin 1; (C) applying, to the plurality of data elements for the subject's cancer comprising the expression levels of the at least 9 signature genes, one or more models that are collectively trained to provide a respective one or more indications of whether the cancer will respond to checkpoint inhibitor therapy, thereby predicting whether the cancer will respond to checkpoint inhibitor; and (D) generating a clinical report comprising the one or more indications of whether the cancer will respond to checkpoint inhibitor therapy. In some embodiments, the method further comprises in step (B), determining (ii) a second set of nucleic acid sequence reads comprising DNA sequence features comprising a mutation status for one or more genes in the subject's cancer, and in step (C), applying the one or more collectively trained models to the mutation status of one or more genes in the subject's cancer. In some embodiments, the plurality of signature genes comprise the first 15 genes in Table 1. In some embodiments, the plurality of signature genes comprise NKG7, CCL5, GZMA, CCL4, CST7, GZMH, GZMB, GZMK, PRF1, GNLY, CCL4, CD74, IL32, CD52, CCL3, LAG3, CTSW, CTSC, CXCR6, ABI3, S100A4. In some embodiments, the training of the one or more models of step (C) comprises i) providing RNA-seq data, tumor mutational burden (TMB) data, and patient health information comprising time to progression data from a cohort of non-subject individuals who have been treated with checkpoint inhibitor; ii) calculating a gene signature comprising the arithmetic mean of log-transformed, normalized RNA counts for the at least 9 genes selected from Table 1 in the RNA-seq data from the cohort of non-subject individuals; iii) training the one or more models with the gene signatures of ii) and the TMB data as features to generate model score data which is predictive of time to progression; iv) setting a threshold value, wherein the threshold value maximizes the separation of the model score data of iii) into two risk categories (1) high risk and (2) low risk.6. The method of claim 1, wherein the cancer comprises non-small cell lung cancer, bladder cancer, colorectal cancer, or liver cancer. In some embodiments, the cancer comprises a non-small cell lung cancer. In some embodiments, one of the indications comprises a cytotoxic score In some embodiments, the first set of RNA features is obtained by whole transcriptome sequencing. In some embodiments, the one or more models is trained to compare expression levels of the signature genes with a control level, and to provide, as an indication of response to checkpoint inhibitor therapy, a cytotoxic score based on the comparison. In some embodiments, the control level is derived from healthy matched tissue, or matched tissue known to lack a cytotoxic gene signature. In some embodiments, the plurality of data elements further comprises an HLA class I gene status of the cancer sample. In some embodiments, the HLA class I gene status of the cancer sample indicates a loss of function mutation in at least one HLA class I gene. In some embodiments, the HLA class I gene status of the cancer sample indicates a loss of heterozygosity in at least one HLA class I gene. In some embodiments, the HLA class I gene status of the cancer sample indicates complete loss of at least one HLA class I gene. In some embodiments, the subject's cancer comprises non-small cell lung carcinoma. In some embodiments, the methods further comprise treating the subject with a checkpoint inhibitor therapy.

In another aspect of the current disclosure, methods of determining an immune-oncology (IO) Progression Risk for a subject diagnosed with cancer are provided. In some embodiments, the method comprises: at a computer system having one or more processors, and memory storing one or more programs for execution by the one or more processors: (A) obtaining, in electronic format, a plurality of sequence reads, wherein the plurality of sequence reads is obtained for a plurality of nucleic acid molecules from a sample of the cancer obtained from the subject; (B) determining, from the plurality of sequence reads, a plurality of data elements for the subject's cancer comprising: a first set of RNA sequence features comprising expression levels of plurality of at least 9 signature genes selected from Table 1, in the sample of the cancer obtained from the subject, wherein the plurality of signature genes comprises at least CCL5, granzyme A, NKG7, CCL4, granzyme B, granzyme H, granulysin, and perforin 1, a mutation status for one or more genes in the patient's cancer; (C) applying, to the plurality of data elements for the subject's cancer comprising the expression levels of the at least 9 signature genes and the tumor mutation burden, one or more models that are collectively trained to provide a respective one or more indications of IO Progression Risk, and (D) generating a clinical report comprising the one or more indications of IO Progression Risk. In some embodiments, at least one of the indications comprises a cytotoxic (CT) score. In some embodiments, at least one of the indications comprises a tumor mutation burden (TMB) for the subject's cancer wherein the TMB is determined based on an analysis of the mutation status for the one or more genes in the patient's cancer, and wherein the one or more genes is selected from ABCB1, ABCC3, ABL1, ABL2, FAM175A, ACTA2, ACVR1, ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf34, CALR, CARD11, CARM1, CASP8, CASR, CBFB, CBL, CBLB, CBLC, CBR3, CCDC6, CCND1, CCND2, CCND3, CCNE1, CD19, CD22, CD274, CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYNC2H1, EBF1, ECT2L, EGF, EGFR, EGLN1, EIF1AX, ELF3, TCEB1, C11orf30, ENG, EP300, EPCAM, EPHA2, EPHA7, EPHB1, EPHB2, EPOR, ERBB2, ERBB3, ERBB4, ERCC1, ERCC2, ERCC3, ERCC4, ERCC5, ERCC6, ERG, ERRFI1, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANCI, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOXP1, FOXQ1, FRS2, FUBP1, FUS, G6PD, GABRA6, GALNT12, GATA1, GATA2, GATA3, GATA4, GATA6, GEN1, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HIST1H1E, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDOL IFIT1, IFIT2, IFIT3, IFNAR1, IFNAR2, IFNGR1, IFNGR2, IFNL3, IKBKE, IKZF1, IL10RA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEF1, LMNA, LMO1, LRP1B, LYN, LZTR1, MAD2L2, MAF, MAFB, MAGI2, MALT1, MAP2K1, MAP2K2, MAP2K4, MAP3K1, MAP3K7, MAPK1, MAX, MC1R, MCL1, MDM2, MDM4, MED12, MEF2B, MEN1, MET, MGMT, MIB1, MITF, MKI67, MLH1, MLH3, MLLT3, MN1, MPL, MRE11A, MS4A1, MSH2, MSH3, MSH6, MTAP, MTHFD2, MTHFR, MTOR, MTRR, MUTYH, MYB, MYC, MYCL, MYCN, MYD88, MYH11, NBN, NCOR1, NCOR2, NF1, NF2, NFE2L2, NFKBIA, NHP2, NKX2-1, NOP10, NOTCH1, NOTCH2, NOTCH3, NOTCH4, NPM1, NQO1, NRAS, NRG1, NSD1, WHSC1, NT5C2, NTHL1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCD1LG2, PDGFRA, PDG-FRB, PDK1, PHF6, PHGDH, PHLPP1, PHLPP2, PHOX2B, PIAS4, PIK3C2B, PIK3CA, PIK3CB, PIK3CD, PIK3CG, PIK3R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2R1A, PPP2R2A, PPP6C, PRCC, PRDM1, PREX2, PRKAR1A, PRKDC, PARK2, PRSS1, PTCH1, PTCH2, PTEN, PTPN11, PTPN13, PTPN22, PTPRD, PTPRT, QKI, RAC1, RAD21, RAD50, RAD51, RAD51B, RAD51C, RAD51D, RAD54L, RAF1, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNX1T1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SMAD2, SMAD3, SMAD4, SMARCA1, SMARCA4, SMARCB1, SMARCE1, SMC1A, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STATE, STK11, SUFU, SUZ12, SYK, SYNE1, TAF1, TANC1, TAP1, TAP2, TARBP2, TBC1D12, TBL1XR1, TBX3, TCF3, TCF7L2, TCL1A, TERT, TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, C10orf54, WEE1, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, and ZRSR2. In some embodiments, at least one of the indications comprises an IO Progression Risk Score. In some embodiments, the IO Progression Risk Score reflects the probability of a progression event occurring in 3 months. In some embodiments, the IO Progression Risk Score reflects the probability of a progression event occurring in 6 months. In some embodiments, the subject's cancer is stage IV. In some embodiments, the subject's cancer is non-small cell lung carcinoma (NSCLC). In some embodiments, the subject's cancer is stage IV NSCLC, or non-stage IV NSCLC with a metastasis event. In some embodiments, the subject's cancer is stage IV, or is earlier than stage IV with a metastasis event and no prior treatment with immune-oncology (IO) therapy. In some embodiments, at least one of the models calculates a CT score, at least one of the models calculates a TMB, and at least one of the models calculates an IO Progression risk score. In some embodiments, the IO Progression Risk score is calculated based on the CT score and the TMB score. In some embodiments, the method further comprises treating the subject's cancer based on the generated report.

In some embodiments, the method comprises determining the presence or absence of a cytotoxic gene signature in a tumor sample from the subject, and optionally treating the subject based on the determination. In some embodiments, the subject has or is suspected of having a loss of heterozygosity in human leukocyte antigen (HLA) class I genes. In some embodiments, the subject is treated with one or more checkpoint inhibitors if a cytotoxic gene signature is identified. In some embodiments, the cancer is colorectal, uterine, stomach, lung, skin, head or neck, or non-small cell lung carcinoma.

In some embodiments, the method comprises determining an immuno-oncology (IO) Progression Risk for a patient sample. In some embodiments, determining IO Progression Risk comprises a predictive algorithm that analyzes the tumor mutational burden (TMB) and the cytotoxic gene signature score (CYT score), indicating, for example, the cytotoxicity of tumor infiltrating immune cells. In some embodiments, the subject has a cancer such as, but not limited to colorectal, uterine, stomach, lung, skin, head or neck, or non-small cell lung carcinoma.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-F. CD4+ T cell subtypes defined by non-negative matrix factorization (NMF). Uniform manifold approximation and projection (UMAP) plots of 16,008 CD4+ T cells from 10 non-small cell lung cancer (NSCLC) tumors. In A-E) each cell is labelled using the NMF weights for each topic (for example, transcriptional signature). In F) NMF cluster membership for each cell, determined by the topic (i.e. transcriptional signature) with the greatest weight, is identified by color.

FIG. 7A-E. A subpopulation of tumor cells express HLA-II in NSCLC, allowing for direct antigen presentation to CD4+ T cells. UMAP projections show the expression of A) HLA-I and B) HLA-II in the CD45– fraction. C) Heatmap shows the expression of HLA-I, HLA-II and key lineage markers. D) Boxplots show the log transformed expression of the individual HLA-II genes assessed ($p<0.0001$, Kruskal-Wallis). E) Expression of HLA-II and its' chaperone, CD74 (invariant chain) is highly correlated ($R=0.627$, $p<0.0001$, Pearson correlation).

FIG. 9A-D. Cohort clinical and genomic characteristics. A) Mutation plot showing the distribution of TMB and frequency of driver mutations. Each column represents a patient and are ordered by progression status at 3 months and TMB. Immunotherapy biomarker status and mutation type are denoted by color. Genes are sorted by frequency of mutation. B) Kaplan-Meier plots showing time to progression on ICB therapy, stratified by PDL1 status ($p=0.20$, log rank), C) TMB status ($HR=0.42$, $p=0.0057$, log rank), and D) HLA class I deficiency status (HLA LOH: $p=0.13$, $HR=0.56$, log rank).

FIG. 13A-E. Cytotoxic gene signature is associated with ICB response in NSCLC. A, Kaplan-Meier plots showing time to progression on ICB therapy, stratified by cytotoxic score (CS) status in the NSCLC IO cohort ($p=0.0045$, $HR=0.42$, Cox PH), B, HLA class I deficient cohort ($p=0.013$, $HR=0.16$, Cox PH), C, Kaplan-Meier plots showing time to progression on ICB therapy, stratified by multimodal score (MM) status in the NSCLC IO cohort ($HR=2.28$, $p=0.00048$, log rank), and D, NSCLC platinum cohort ($HR=1.27$, $p=0.85$, log rank). E, Correlation of TMB and CS in the NSCLC IO cohort ($R=0.08$, $p=0.35$, Pearson correlation).

FIG. 17A-B. A, Exemplary threshold calculation. B, Table showing the distribution of scores in the training set.

FIG. 20 illustrates results after assessing a coxPH model using binarized TMB & continuous CYT score against potential clinical confounders.

FIG. 21 illustrates the stability of the model performance over multiple shuffles of data (different folds of data). Test set size in each fold is on average 16. In this example, the small sample size leads to the large confidence intervals for the HR.

FIG. 22 illustrates the stability of the model prediction over multiple shuffles of data (different folds of data). The majority of patients were labeled consistently as high or low risk across shuffles.

FIG. 24 is a block diagram illustrating a system for performing selection, alteration, and calculation of additional features from the patient features, in accordance with some embodiments of the present disclosure.

DETAILED DESCRIPTION

Introduction

Figures 1A, 1B, 1C, 1D, 1E:
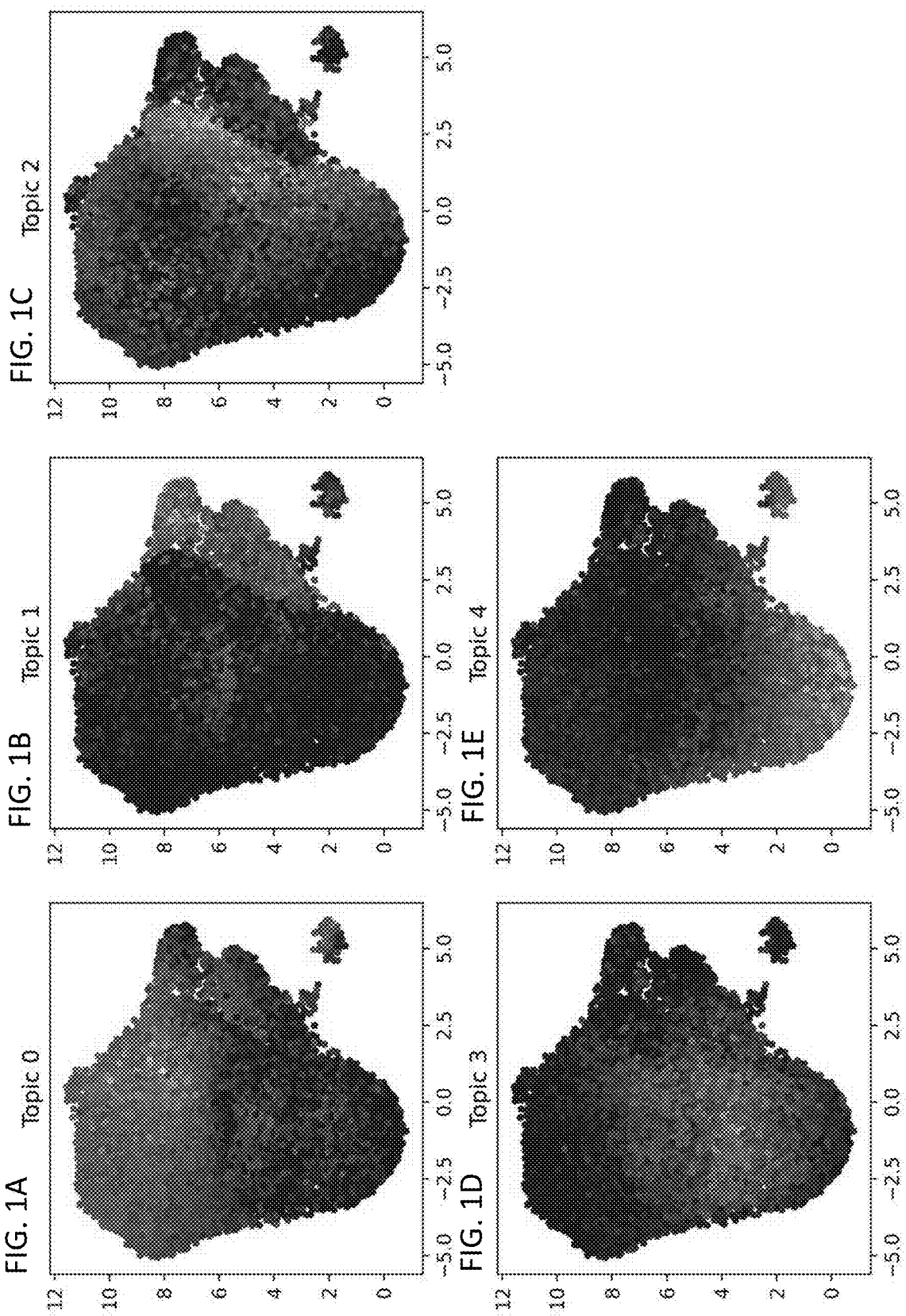

The systems, methods, and compositions described herein relate to the identification of a novel, cytotoxic gene signature (CYT) that when identified in a tumor sample, can be used to direct patient therapy, and in particular, checkpoint inhibitor therapy. Although the identification of expression of cytotoxic genes (e.g., genes associated with cytotoxic immune cells) in tumor samples is not new, the present disclosure provides for the detection of a novel and non-obvious set of genes to allow for more accurate and more specific identification of cytotoxic immune cells within a patient tumor sample. This enhanced accuracy and specificity provides both patients and physicians improved information regarding predicted or likely checkpoint inhibitor efficacy.

In addition to a cytotoxic gene signature or score derived therefrom, in various embodiments, the systems and methods include the use of next-generation sequencing of tumor biopsy samples to generate molecular-based progression risk scores that can help inform a physician's management of immune-oncology (IO) therapy decisions and duration. The tumor immune microenvironment (TIME) modulates tumor killing by immune cells and has prognostic value in determining the clinical course and survival of an individual patient. DNA and RNA sequencing can measure tumor and immune intrinsic mechanisms of sensitization to IO therapy in the TIME, including the tumor mutational burden of the cancer (TMB) and the cytotoxicity of tumor infiltrating immune cells (CYT). In various embodiments, additional molecular data and/or clinical data characteristics of the patient (for example, immune infiltration, T-cell IHC markers including CD3, other indicators of the presence of immune cells in the tumor, RNA gene expression signatures, other indicators of increased interferon gamma activity or increased immune activity/inflammation, HLA LOH, HLA expression, HLA mutations, immune resistance mutations (for example, mutations in IO resistance genes including B2M, JAK1, JAK2, IFNGR1, IFNGR2, TAP1, etc.), other indicators of loss of HLA, Neoantigens, TMB, MSI, other tumor cell mutation data) may further refine the prediction of the patient's likely risk of progression after receiving IO therapy.

Also disclosed are engines for predicting response to immunotherapy and for providing progression risk scores. Immune-Oncology (IO) Response Profile As used herein, the term IO Response Profile comprises a list of genes and their respective expression levels in a subject tumor sample, and is useful to determine, for example, whether a cancer will respond to an immune-oncology therapy, such as a checkpoint inhibitor. The genes that comprise an IO Response Profile include one or more of the genes from Table 1.

In some embodiments, an IO Response Profile is analyzed for the presence or absence of a cytotoxic gene signature (CYT). In some embodiments, the presence or absence of a cytotoxic gene signature is identified by evaluating the expression level of one or more genes shown in Table 1 (termed herein "IO response genes," or "signature genes") in a tumor sample from the subject and comparing the signature gene expression level to a control expression level or to a predetermined threshold level for the signature genes. The expression level of the IO profile genes is indicative of the presence or absence of cytotoxic immune cells, for example, cytotoxic CD4+ T cells, cytotoxic CD8+ T cells, cytotoxic natural killer (NK) T cells, etc. in the tumor sample. In some embodiments, an IO Response Profile is analyzed and a single value, termed a cytotoxic score (CS) is provided. The CS is compared to a threshold or control level, and the cytotoxicity of the gene signature is determined. As used herein, "CYT score" and CS are used interchangeably. In one example, a CS (or CYT score) above a threshold or control level indicates a cytotoxic gene profile. A CS below a threshold or control level indicates the absence of a cytotoxic gene profile. In some embodiments, a cytotoxic gene profile is an indicator of a likely favorable response to checkpoint inhibitor therapy.

In some embodiments, an IO Response Profile comprises expression data associated with the following genes of a subject's tumor sample: CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, and DUSP4. In some embodiments, the IO Response Profile comprises expression data associated with the following genes of a subject's tumor sample: CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, DUSP4, CTSC, CXCR6, ABI3, S100A4, and FGFBP2.

In some embodiments, an IO Response Profile is characterized by the expression of e.g., the first 2, 5, 10, 15, 20, 25, 30 or the first 50 genes listed in Table 1, where the genes are arranged in order from the greatest associated weight value to the least associated weight value. In some embodiments, expression of the first 25 genes of Table 1 comprises an IO Response Profile of a tumor sample. In some embodiments, the terms IO response profile is a gene signature.

In some embodiments, an IO Response Profile is determined by identification and quantitation of cells expressing granzyme A (GZMA), granzyme H (GZMH), granulysin (GNLY), and/or perforin 1 (PRF1) in a subject's tumor sample.

TABLE 1

| IO Response Profile Genes (Signature Genes) | |
|---|---|
| Gene | Weight |
| CCL5 | 0.11553707 |
| GZMA | 0.11119375 |
| NKG7 | 0.10792594 |
| CCL4 | 0.10607658 |
| GZMH | 0.09819277 |

TABLE 1-continued

| IO Response Profile Genes (Signature Genes) | |
| --- | --- |
| Gene | Weight |
| CST7 | 0.09637749 |
| GZMB | 0.09052262 |
| GZMK | 0.08087941 |
| GNLY | 0.07304029 |
| PRF1 | 0.0697381 |
| CCL4L2 | 0.06746927 |
| CD52 | 0.0671189 |
| IL32 | 0.06348354 |
| CD74 | 0.06177709 |
| CTSW | 0.06042883 |
| CRIP1 | 0.05988814 |
| CCL3 | 0.05630675 |
| ITM2C | 0.05581316 |
| IFNG | 0.05233069 |
| S100A10 | 0.05015405 |
| TUBA4A | 0.04922318 |
| FGFBP2 | 0.04810496 |
| LAG3 | 0.04724802 |
| S100A4 | 0.04609252 |
| EOMES | 0.04545036 |
| HOPX | 0.04443346 |
| DUSP4 | 0.04436067 |
| PLEK | 0.04343599 |
| S100A11 | 0.04326302 |
| ABI3 | 0.04315321 |
| KLRD1 | 0.04282515 |
| LGALS1 | 0.04281545 |
| CTSC | 0.04278671 |
| CRTAM | 0.04165706 |
| ZNF683 | 0.04127708 |
| DUSP2 | 0.03970615 |
| SRRT | 0.03917101 |
| CLEC2B | 0.03907536 |
| LDHA | 0.038759 |
| ENC1 | 0.03859638 |
| OASL | 0.03731479 |
| ZEB2 | 0.03720007 |
| HSPE1 | 0.03704164 |
| CXCR6 | 0.03624443 |
| GIMAP4 | 0.03505498 |
| PTMS | 0.03441307 |
| DNAJA1 | 0.03425662 |
| GIMAP7 | 0.03418167 |
| PDCD1 | 0.03324803 |
| TNFSF9 | 0.03300823 |
| ISG20 | 0.03253554 |
| CCL3L1 | 0.03244689 |
| PKM | 0.03164835 |
| CXCR3 | 0.03160576 |
| SLA | 0.03077559 |
| XCL2 | 0.03022319 |
| TBX21 | 0.02981124 |
| FASLG | 0.02965684 |
| RNF213 | 0.02941825 |
| SLAMF7 | 0.02896132 |
| CD70 | 0.02891628 |
| FABP5 | 0.02871164 |
| FCRL6 | 0.02843698 |
| ITM2A | 0.02792281 |
| SYTL3 | 0.02776929 |
| S1PR5 | 0.02763959 |
| RGS1 | 0.02762577 |
| TXNIP | 0.02746667 |
| LGALS3 | 0.02741297 |
| KLRG1 | 0.02715867 |
| TYROBP | 0.02707809 |
| RPS27L | 0.02704993 |
| H2AFZ | 0.02703339 |
| TRAT1 | 0.02688795 |
| ITGA1 | 0.0268685 |
| XCL1 | 0.02667611 |
| RGCC | 0.02655055 |
| CACYBP | 0.02653767 |
| LYST | 0.02621355 |
| GGA2 | 0.02590172 |
| ID2 | 0.02578471 |

TABLE 1-continued

| IO Response Profile Genes (Signature Genes) | |
| --- | --- |
| Gene | Weight |
| SAMSN1 | 0.02578401 |
| PTPN7 | 0.02543192 |
| MT2A | 0.02527319 |
| TGFB1 | 0.02501246 |
| HAVCR2 | 0.02491684 |
| ISG15 | 0.02412499 |
| GBPS | 0.02334112 |
| KRT86 | 0.02326803 |
| MAP3K8 | 0.02320523 |
| SYNE1 | 0.02314846 |
| SLC7A5 | 0.02304304 |
| ARHGAP30 | 0.02301441 |
| HSPH1 | 0.02300987 |
| CORO1B | 0.02258396 |
| KIAA1551 | 0.02231347 |
| PARP8 | 0.022299 |
| THEMIS | 0.02223858 |
| MYO1F | 0.02199791 |
| FKBP4 | 0.02191047 |

While some of the genes identified in Table 1 are known to be expressed by, or associated with cytotoxic CD8+ T cells, surprisingly and unexpectedly, the expression of the genes in Table 1 were identified in cytotoxic CD4+ T cells that had infiltrated tumor non-small cell lung carcinoma (NSCLC) samples. That is, the novel cytotoxic gene signature of the present disclosure was identified in tumor infiltrating cytotoxic CD4+ T cells. The present disclosure provides a correlation between the presence of the cytotoxic gene signature in a tumor sample, and responsiveness to one or more therapeutic agents such as checkpoint inhibitors. Not all 100 genes of Table 1 need be characterized to identify a cytotoxic gene signature in a sample. In some embodiments, the first 2, 5, 10, 20, 25, 27, 30, or 50 genes are selected for evaluation. Elevated expression levels of the first 2, 5, 10, 20, 25, 27, 30, or 50 genes selected from Table 1 as compared to a control or a threshold level is indicative of a cytotoxic gene signature in the tumor sample, and is indicative of a favorable response to checkpoint inhibitor therapy. In some embodiments, the RNA expression level of CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, and DUSP4 are characterized to determine a cytotoxic gene signature. In some embodiments, the RNA expression level of CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, DUSP4, CTSC, CXCR6, ABI3, S100A4, and FGFBP2 are characterized to determine a cytotoxic gene signature.

Expression levels of the selected genes from Table 1 may be determined by any of a number of methods, and may encompass either or both protein and RNA detection.

The presence or absence of a cytotoxic gene signature may be determined in any number of cancer types, and is not limited to NSCLC; the cancer may also be identified as having an altered human leukocyte antigen (HLA) phenotype, e.g., a loss of heterozygosity at the HLA locus. In addition, the subject's cancer treatment regimen, or lack thereof, prior to testing for a cytotoxic gene signature is not limiting. In various embodiments, there is no statistically significant difference between the distribution of CSs (for example, see FIG. 17B) when comparing primary tumor specimens to metastatic tumor specimens, when comparing specimens of different tissue types (for example, pleura, lymph node, lung, brain, liver, airway, missing data, other, etc.), when comparing two different RNA sequencing panels on the same group of specimens, when comparing biopsy procedure type (for example, surgical resection, none, core needle biopsy, biopsy, etc.), when comparing histology type (for example, adenocarcinoma, adenosquamous carcinoma, non-adenocarcinoma non-squamous carcinoma cell carcinoma, unknown, etc.), when comparing gender (male, female, etc.), or when comparing stage (for example, stage 1, 2, 3, or 4, none, or N/A). In some examples, CYT score is slightly decreased in Brain and Liver biopsies relative to all other biopsy tissue, which may be caused by Brain/Liver sample sizes being small. In some examples, CYT score correlates with tumor purity and estimated immune cell infiltration (based on histology or RNA sequencing data).

Figure 2:
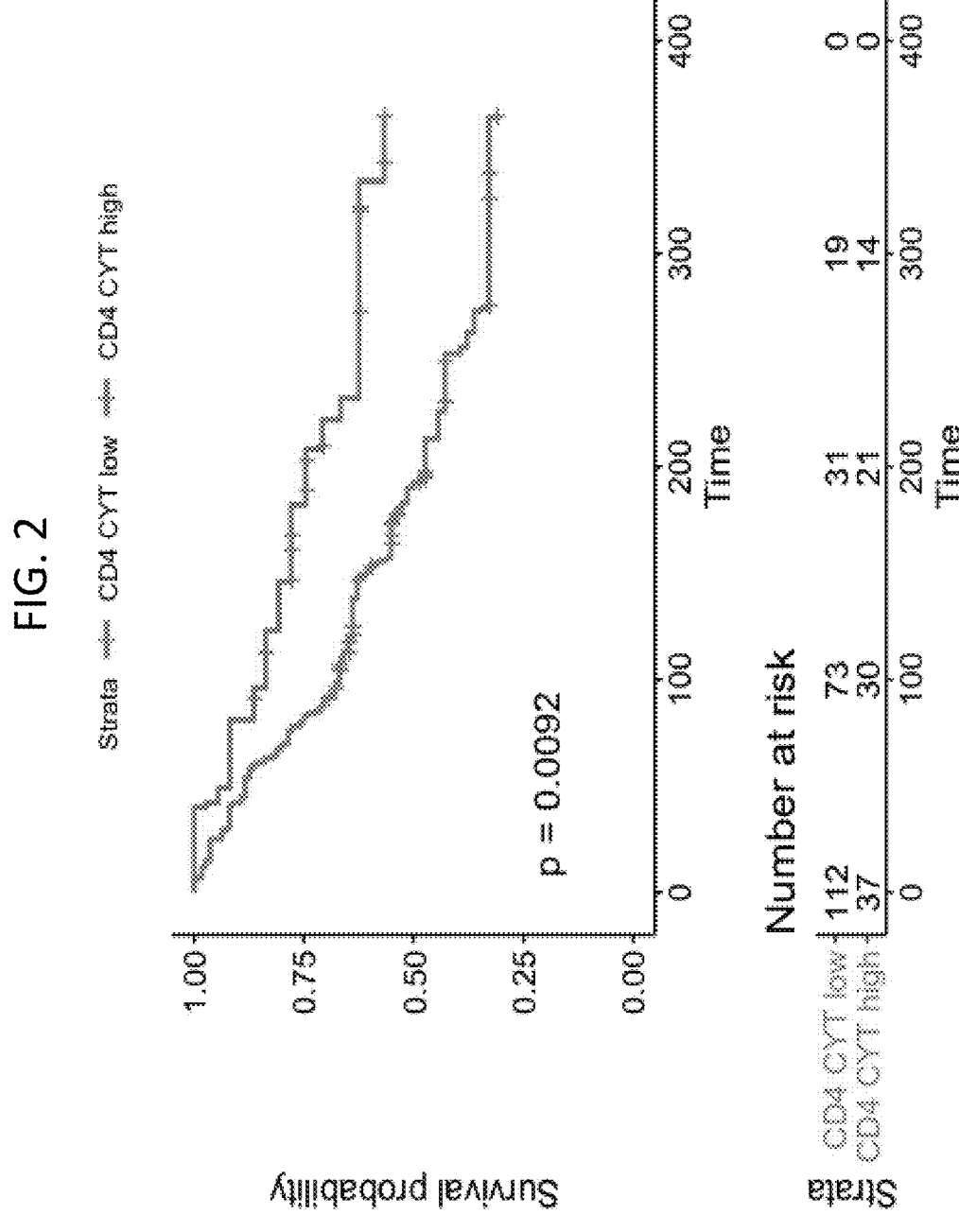
FIG. 2. A CD4+ T cell cytotoxic gene signature is associated with progression free survival in a cohort of NSCLC patients (n=154) treated with checkpoint inhibitor regimens. All patients had metastatic NSCLC. Patients were treated with a Food and Drug Administration (FDA) approved checkpoint inhibitor regimen and underwent Tempus genomic profiling as part of their clinical care. Patients were ranked based on their tumor's expression of the CD4+ T cell cytotoxic gene signature, as described in Example 1. Survival probability over time was higher for patients who had higher expression of the genes defining the CD4+ T cell cytotoxic gene signature (log rank test, p=0.0092).

CD4+ cytotoxic T cells are an underappreciated, potentially anti-tumor cytotoxic T cell population. Immune checkpoint blockade (ICB) is widely used to treat non-small cell lung cancer (NSCLC) patients and works by inhibiting the PD-1/PDL1 axis to reinvigorate exhausted T cells, allowing them to attack the tumor. While the effects of ICB are generally considered to come from CD8+ T cells, the inventors performed single cell RNAseq on tumor samples from 10 NSCLC patients to characterize a population of tumor infiltrating, clonally expanded CD4+ T cells that express a cytotoxic gene signature. Concordantly, a subpopulation of tumor cells with elevated HLA class II expression was identified in these patients, suggesting that direct CD4+ T cell mediated tumor killing may be a second avenue of anti-tumor immunity. Finally, it was shown that a CD4+ T cell cytotoxic gene signature is associated with progression free survival in a cohort of 154 NSCLC patients treated with ICB regimens, including those with loss of heterozygosity in the HLA class I locus (see FIGS. 2 and 3).

IO Progression Risk

As described above, the tumor immune microenvironment (TIME) modulates tumor killing by immune cells and has prognostic value in determining the clinical course and survival of an individual patient. The novel methods and systems disclosed herein are used to analyze DNA and RNA sequences to measure tumor and immune intrinsic mechanisms of sensitization to IO in the TIME, including the tumor mutational burden of the cancer (TMB) and the cytotoxicity of tumor infiltrating immune cells (e.g., by determining the presence or absence of a cytotoxic gene signature).

In some embodiments, the systems and methods disclosed herein comprise a predictive algorithm that analyzes tumor mutation burden (TMB) and CYT measurements associated with a patient specimen to generate a score reflecting probability of a progression event (progression risk, IO progression risk score, or progression risk score). An exemplary Progression Risk assessment and model is provided in Example 5.

The presence or absence of a cytotoxic gene signature (or CYT score, or CS), can be determined as described above.

In some embodiments, the TMB is determined by using a targeted panel DNA sequencing assay, employing Next Generation Sequencing (NGS) methods. In some embodiments, the targeted panel assay and/or TMB calculation method is as described in U.S. application Ser. No. 16/789, 288, published as US 2020/0258601, titled *Targeted-Panel Tumor Mutational Burden Calculation Systems and Methods*, incorporated herein by reference in its entirety, and Beaubier et al., Oncotarget. 2019 Mar. 22; 10(24): 2384-2396, herein incorporated by reference in its entirety.

In some embodiments, the targeted panel assay includes reagents (such as probes), software, instruments and procedures for sequencing a subject's tumor sample and matched or normal sample. In some embodiments the assay is designed to detect and identify somatic alterations. Such genetic information can be used to calculate TMB for that specimen (see for example, U.S. application Ser. No. 16/789,288, U.S. Pub. No. 2020/0258601), and can also be used by qualified healthcare professional to aid in the clinical management of previously diagnosed cancer patients with solid malignant neoplasms (see for example Beaubier, et al., 2019).

In some embodiments, the tumor sample comprises formalin-fixed, paraffin-embedded (FFPE) tumor specimens, tissue sections, surgical biopsy, skin biopsy, punch biopsy, prostate biopsy, bone biopsy, bone marrow biopsy, needle biopsy, CT-guided biopsy, ultrasound-guided biopsy, fine needle aspiration, aspiration biopsy, fresh tissue or blood samples. In some embodiments, matched normal samples include matched tumor-free tissue (for example, biopsy) or saliva or blood specimens. In some embodiments, the tumor sample comprises a somatic specimen. In some embodiments, the normal or tumor-free sample comprises a germline specimen.

In some embodiments, TMB is calculated as the number of non-synonymous somatic mutations (a mutation which results in a change in the amino acid sequence of the protein) divided by the amount of DNA sequenced (see Equation 1, below), using for example, the variant annotation output from a tumor-normal matched targeted sequencing panel for oncology patient specimens and the bioinformatics variant calling pipeline corresponding to the sequencing panel (see for example Beaubier, et al., 2019).

Equation 1

$$TMB = \frac{(\text{number of non-synonymous somatic mutations})}{(\text{megabases of DNA sequenced})}$$

In some embodiments, a TMB calculation includes synonymous mutations. In some embodiments, a TMB calculation does not include synonymous mutations.

Figure 18A:
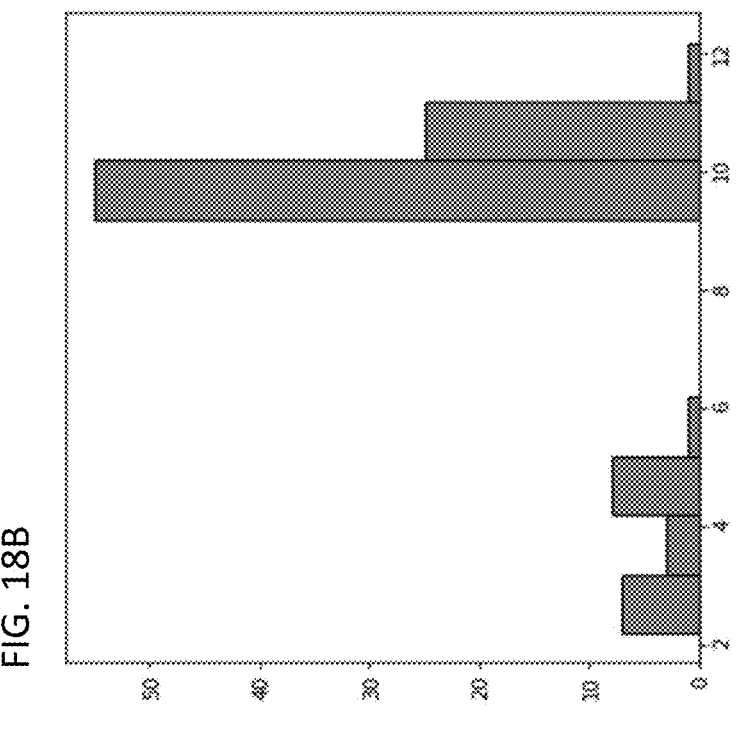
FIG. 18A-B. A is a plot showing the log rank statistic (y-axis) for each value of TMB (x-axis) used to split the cohort. For example, the x-axis shows the selected test TMB threshold value and the y-axis shows the log rank statistic for each test TMB threshold value selected. In various embodiments, a test TMB threshold value associated with a large log rank statistic value may be designated as the final, optimized TMB threshold value. y-axis: Log rank statistic; x-axis: TMB. B is a histogram showing the TMB threshold selected (x-axis) if the plot in A is repeated over 100 shuffles of the data. X-axis: TMB threshold selected; Y-axis # of folds (for example, a fold in machine learning can refer to a subset of training data).
Figure 18B:
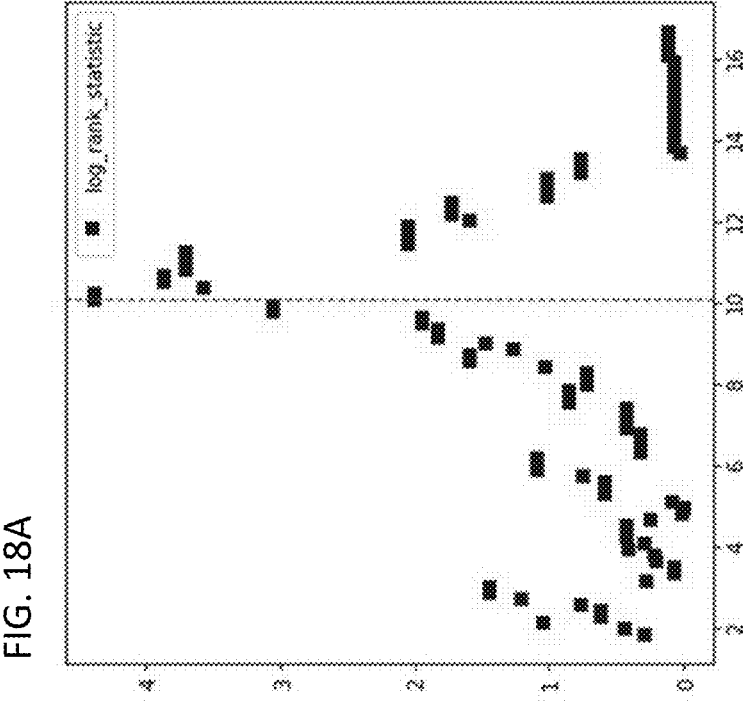

In some embodiments, following TMB and CYT score calculation, optimized thresholds are used to determine if a tumor has a TMB greater than the TMB threshold, or CYT score is greater than the CYT threshold, or both. Those results are then used to assign progression risk, using, for example, the ruleset outlined in Table 2, below. If the TMB score is below the TMB threshold, and the CYT score is below the CYT threshold, the IO Progression Risk test will determine "increased progression risk." In all other cases, "no increased progression risk detected" will be determined (Table 2). The optimized threshold for TMB and CYT, in some embodiments, is identified using a proprietary method in a real-world evidence (RWE) study cohort of metastatic NSCLC patients. Briefly, we used a real world cohort of 140 metastatic NSCLC patients to optimize thresholds for TMB and CYT. For each metric, we binarized the data at 100 potential threshold values generated based on the range of the metric. We then used the log rank test to assess each version of the binarized metric's association with time to progression. We identified a candidate threshold that maximized the log rank statistic. We then assessed the robustness of the threshold by randomly subsampling the cohort and repeating the threshold optimization procedure. In another example, the TMB threshold was optimized on a cohort of 220 NSCLC patients treated with IO therapy, where each patient was associated with DNA sequencing data. Optionally, the patients may be further associated with RNA sequencing data. See for example, FIG. 18.

In some embodiments, methods for predicting response to checkpoint inhibitor in a subject suffering from cancer are provided. In some embodiments, the method comprises: at a computer system having one or more processors, and memory storing one or more programs for execution by the one or more processors: (A) obtaining, in electronic format, a plurality of sequence reads, wherein the plurality of sequence reads is obtained for a plurality of nucleic acid molecules from a sample of the cancer obtained from the subject; (B) determining, from the plurality of sequence reads, a plurality of data elements for the subject's cancer comprising: (i) a first set of nucleic acid sequence reads comprising RNA sequence features comprising expression levels of a plurality of at least 9 signature genes selected from Table 1, in the sample of the cancer obtained from the subject, wherein the plurality of signature genes comprises at least CCL5, granzyme A, NKG7, CCL4, granzyme B, granzyme H, granulysin, and perforin 1; (C) applying, to the plurality of data elements for the subject's cancer comprising the expression levels of the at least 9 signature genes, one or more models that are collectively trained to provide a respective one or more indications of whether the cancer will respond to checkpoint inhibitor therapy, thereby predicting whether the cancer will respond to checkpoint inhibitor; and (D) generating a clinical report comprising the one or more indications of whether the cancer will respond to checkpoint inhibitor therapy.

In some embodiments, the method further comprises in step (B), determining (ii) a second set of nucleic acid sequence reads comprising DNA sequence features comprising a mutation status for one or more genes in the subject's cancer, and in step (C), applying the one or more collectively trained models to the mutation status of one or more genes in the subject's cancer. In some embodiments, the training of the one or more models of step (C) comprises i) providing RNA-seq data, tumor mutational burden (TMB) data, and patient health information comprising time to progression data from a cohort of non-subject individuals who have been treated with checkpoint inhibitor; ii) calculating a gene signature comprising the arithmetic mean of log-transformed, normalized RNA counts for the at least 9 genes selected from Table 1 in the RNA-seq data from the cohort of non-subject individuals; iii) training the one or more models with the gene signatures of ii) and the TMB data as features to generate model score data which is predictive of time to progression; iv) setting a threshold value, wherein the threshold value maximizes the separation of the model score data of iii) into two risk categories (1) high risk and (2) low risk.

In some embodiments, training of the one or more models comprises first establishing the association of each gene in the CYT score with time to progression in an IO training cohort using one or more models, e.g., a Cox proportional hazards model. In some embodiments, the CYT score comprises set of nucleic acid sequence reads comprising RNA sequence features comprising expression levels of a plurality of at least 9 signature genes selected from Table 1, in the sample of the cancer obtained from the subject, wherein the plurality of signature genes comprises at least CCL5, granzyme A, NKG7, CCL4, granzyme B, granzyme H, granulysin, and perforin 1. In some embodiments, genes with a hazard ratio less than 1, including by way of example, but not by way of limitation NKG7, CCL5, GZMA, CCL4, CST7, GZMH, GZMB, GZMK, PRF1, GNLY, CCL4L2, CD74, IL32, CD52, CCL3, LAG3, CTSW, CTSC, CXCR6, ABI3, S100A4 are selected for the final CYT gene signature. The CYT gene signature is, in some embodiments, calculated as the arithmetic mean of the log-transformed, normalized RNA counts for the selected genes. In some embodiments, the method further comprises in step (B), determining (ii) a second set of nucleic acid sequence reads comprising DNA sequence features comprising a mutation status for one or more genes in the subject's cancer, and in step (C), applying the one or more collectively trained models to the mutation status of one or more genes in the subject's cancer. In some embodiments, a model, e.g., a multivariate Cox proportional hazards model, is trained using a training cohort with the CYT gene signature and tumor mutational burden TMB status as features to predict time to progression. As used herein, time to progression (TTP), is defined as the time from CPI start to the first progression event, censored on the last known physician encounter. In some embodiments, the training cohort comprises RNA-seq data, tumor mutational burden (TMB) data, and patient health information comprising time to progression data from a cohort of non-subject individuals who have been treated with checkpoint inhibitor. As used herein, patient health information includes basic biometric and/or biographical data e.g., height, weight, age, gender, race, ethnicity, treatment history, disease history, time to progression, or, for example, other information relevant to evaluation of the success of checkpoint therapy, and the like. In some embodiments, a model, e.g., a multivariate Cox proportional hazards model, is trained using a cohort of subjects diagnosed with a cancer (e.g., NSCLC) with the CYT gene signature and TMB status as features to predict time to progression. In some embodiments, a threshold is set to divide model scores into risk categories, e.g., 2, 3, 4, or more categories. In some embodiments, the threshold is set to binarize the model scores into high risk and low risk by identifying the model score that maximizes the separation of the Kaplan-Meier curves for the two risk categories.

TABLE 2

Feature combination and risk assignment for the IO Progression Risk Test

| | TMB ≥ threshold | TMB < threshold |
|---|---|---|
| CYT > threshold | no increased progression risk detected | no increased progression risk detected |
| CYT < threshold | no increased progression risk detected | increased progression risk |

In some embodiments, the IO Progression Risk score reflects the probability of an event occurring in 3 months; in some embodiments, the IO Progression Risk score reflects the probability of a progression event occurring in 6 months. In some embodiments, the IO Progression Risk score reflects the probability of a progression event occurring in 3 months and 6 months. In some embodiments, a single model assigns patients into high and low risk populations. By way of example, using the Kaplan Meier methods, we can estimate what fraction in each population is likely to progress within 3 months and within 6 months.

For example, the clinician could opt for shorter intervals between imaging studies for a subject with an 'increased risk' result, or interpret radiographic changes on cross-sectional imaging with a higher pre-test probability for disease progression and prepare for testing such as CNS imaging and/or transitioning toward the next line of therapy. Accurately refining pre-test probability may inform clinical judgment and lead to better outcomes by identifying progression events sooner, limiting usage of ineffective and costly IO regimens, and improving patient quality of life by potentially transitioning to the next line of therapy before asymptomatic progression becomes symptomatic progression.

In some embodiments, an IO Progression Risk Test is used for patients diagnosed with non-small cell lung cancer (NSCLC) with a non-squamous histology subtype that will be prescribed IO therapy regimens. In some embodiments, patients must have stage IV disease or an earlier stage disease with a metastasis event, and have had no prior treatment with IO therapy regimens.

In some embodiments, the IO Progression Risk Test is used for Stage IV NSCLC patients or earlier stage NSCLC patients with a metastasis event, with a non-squamous histology subtype prior to first use of IO therapy.

In some embodiments, IO Progression Risk Test is used for patients having head and neck cancer or bladder cancer. In some embodiments, the IO Progression Risk Test is intended for use for patients having any cancer type.

In some embodiments, the IO Progression Risk test is a next-generation sequencing (NGS) based test that provides physicians with a progression risk assessment for metastatic NSCLC patients being treated with a checkpoint inhibitor (CPI) regimen based on profiling the tumor immune microenvironment.

In some embodiments, the IO Progression Risk test comprises a machine learning model that is simple, easily interpretable, stable across folds, and trained based on features having prior evidence of being associated with immunotherapy response. In some embodiments, a percentage of the training cohort patients (for example, 5%, 10%, 15%, 20%, 25%, etc.) have immune checkpoint inhibitor (ICI) resistance mutations (B2M, JAK1, JAK2, IFNGR1, IFNGR2, TAP1) but these mutations may not be factored into an assessment of IO Progression Risk. In an alternative embodiment, mutation status of any of these genes may be used as another feature in a machine learning model trained to predict IO progression risk, for example, for patients having melanoma or NSCLC.

Applications and Advantages of the IO Progression Risk Test

While the majority of metastatic NSCLC patients are being treated with checkpoint inhibitor (CPI) agents in the first line as part of the standard of care, there are few tools for assessing a patients' risk for progression prior to the start of treatment. As currently practiced, there is substantial variation in acceptable surveillance regimens for NSCLC patients during IO treatment, with routine follow-ups consisting of CT scans scheduled every three to six months with the purpose of detecting recurrent tumors. However, such routine scheduled follow-ups can delay diagnosis and treatment if recurrence occurs between planned visits. Furthermore, the standard of care on-treatment radiologic assessments of response can be more challenging to interpret for this patient population due to the risk of pseudo-progression, which is a transient enlargement of the tumor from elevated immune infiltration rather than a true increase in tumor burden. With the IO Progression Risk test, a physician will have additional information on a patient's risk of progression when deciding the cadence of on-treatment radiologic assessments and when interpreting inconclusive radiology results. The IO Progression Risk test would support physicians in identifying the optimal scan intervals for their patients.

Metastatic NSCLC patients have a substantial symptom burden and physicians seek to balance using aggressive treatment for reducing tumor burden with management of patient quality of life. The IO Progression Risk test aids physicians in identifying patients at higher risk for disease progression on CPI. These high risk patients can then be prioritized for more frequent radiologic scans to facilitate earlier detection of their disease progression, allowing physicians to begin considering alternative therapies or the transition to palliative care sooner. This improved patient management may lead to improved clinical care.

Lung cancer, which includes NSCLC, remains the leading cause of cancer related deaths in the United States, despite significant advances in the treatment landscape with the advent of CPI. The five-year survival rate for metastatic NSCLC remains low, at only 0-10% and the vast majority of patients will experience disease progression during CPI treatment. Currently, there are limited options for the treatment management of metastatic NSCLC patients on CPI regimens. Physicians primarily rely on radiologic response assessments to identify disease progression, but there are no national guidelines for the frequency of scans. In addition, inconclusive results from those scans, such as those from patients experiencing pseudo-progression, can further complicate treatment decision making. The IO Progression Risk test supports physician decision making in both the scheduling of radiologic assessments and the interpretation of those results. Earlier identification of true progression events can lead to improved patient management.

In various embodiments, the systems and methods serve as another tool in a physician's toolbox in considering and managing care by describing the immune phenotype of the tumor, how sensitive the tumor-immune microenvironment may be to treatment with immune checkpoint (for example, "Immune hot" or "Immune cold").

In various embodiments, the systems and methods might inform the choice of immune checkpoint regimen when multiple options exist for specific patient subsets (for example, if PD-L1 IHC>50%).

The sooner disease progression on CPI can be identified, the earlier physicians can begin considering alternative treatment regimens that may be more effective or the transition to palliative care to optimize patient comfort.

Definitions

To aid in understanding the invention, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

As used herein, the term "subject" may be used interchangeably with the term "patient" or "individual" and may include an "animal" and in particular a mammal. Mammalian subjects may include humans and other primates, domestic animals, farm animals, and companion animals such as dogs, cats, guinea pigs, rabbits, rats, mice, horses, cattle, cows, and the like.

In some embodiments, the subject has been diagnosed with cancer. In some embodiments, the subject has an altered human leukocyte antigen (HLA) phenotype in a population of cells of the tumor. As used herein, the term "altered HLA phenotype" refers to a phenotype in which the expression of at least one HLA gene is altered relative to wild-type HLA gene expression. The "HLA complex" is the major histocompatibility complex (MHC) in humans, and it comprises a group of related cell-surface proteins that regulate the immune system.

In some embodiments, the altered phenotype comprises a mutation in at least one HLA class I gene. The HLA complex is located at 6p21.3 on chromosome 6, and downregulation or loss of HLA class I expression in tumor cells is a known mechanism of cancer immune evasion. Loss of heterozygosity (LOH) is the most common mechanism of HLA haplotype absence in a malignant tumor, and the frequency of LOH-6p21 has been reported in many cancer types. Furthermore, LOH has been implicated in carcinogenesis and its presence is a useful prognostic marker in many malignant tumors. Thus, one mechanism of immune escape for tumors is loss of heterozygosity in HLA genes (HLA-LOH), which reduces the total number of neoantigens available for presentation to T cells.

As used herein a "subject sample" or a "biological sample" from the subject refers to a sample taken from the subject, such as, but not limited to a tissue sample (e.g., fat, muscle, skin, neurological, tumor, etc.) or fluid sample (e.g., saliva, blood, serum, plasma, urine, stool, cerebrospinal fluid, etc.), and or cells or sub-cellular structures. In some embodiments, a subject sample comprise a tumor sample, such as a biopsy. Such a sample may be fresh, frozen, or formalin fixed paraffin embedded (FFPE).

As used herein, the term "CD8+ T cells" refers to a subpopulation of HLA class I-restricted T lymphocytes that express the co-receptor protein CD8. CD8+ T cells recognize peptides presented by HLA Class I molecules, found on all nucleated cells. CD8+ T cells include cytotoxic T cells, which are important for killing cancerous, virally infected cells, and cells that are damaged in other ways, and CD8-positive suppressor T cells, which restrain certain types of immune response.

As used herein, the term "CD4+ T cells" refers to a subpopulation of HLA class II-restricted T lymphocytes that express the co-receptor protein CD4. CD4+ T cells are also referred to as "T helper cells" because they "help" the activity of other immune cells by releasing cytokines, small protein mediators that alter the behavior of target cells that express receptors for those cytokines. Studies have shown that a subset of CD4+ T cells with a cytotoxic gene profile can mediate direct killing of tumor cells (1,2,3). Specifically, these CD4+ T cells express proteins, such as perforin (a pore-forming protein) and granzymes (a family of serine proteases), which are commonly associated with CD8+ T cells. T cells use a combination of perforin and granzymes to induce apoptosis in virus-infected or transformed cells.

As used herein, the terms "cytotoxic gene signature" with reference to a tumor sample refers to a IO Response Profile that is correlated with presence of cytotoxic immune cells, for example, cytotoxic CD4+ T cells, cytotoxic CD8+ T cells, cytotoxic natural killer (NK) T cells, etc. In some embodiments, the presence or absence of a cytotoxic gene signature is determined by evaluating the expression level of one or more genes shown in Table 1 (termed herein "IO response genes," or "signature genes") in a tumor sample from the subject and comparing the level to a control expression level or to a predetermined threshold level for the signature genes, and the presence or absence of a cytotoxic gene signature is identified.

As used herein a cytotoxic signature score (CYT score) or cytotoxic score (CS) are used interchangeably and refer to a value representative of an IO Response Profile. In some embodiments, a CYT score or CS above a threshold or control value indicates a cytotoxic gene profile, and a CYT score or CS below a threshold or control value indicates the absence of a cytotoxic gene profile.

As noted previously, an IO Response Profile is characterized by the expression level of at least a subset of the genes listed in Table 1 in a tumor sample from the subject. In some embodiments, an IO Response Profile is characterized by the expression of e.g., the first 2, 5, 10, 15, 20, 25, 30 or the first 50 genes listed in Table 1. In some embodiments, an IO response profile is determined by identification of cells expressing granzyme A (GZMA), granzyme H (GZMH), granulysin (GNLY), and/or perforin 1 (PRF1). In some embodiments, expression of the first 25 genes of Table 1 is comprises an IO Response Profile in a tumor sample.

In some embodiments, the control level or the predetermined threshold value is derived from healthy matched tissue, or matched tissue known to lack a cytotoxic gene signature. By "matched tissue" is meant the same tissue type, e.g., lung tissue control if the tumor is lung cancer, liver tissue control if the tumor is liver cancer, etc. By way of example but not by way of limitation, in some embodiments, a control level or threshold level is derived from whole transcriptome expression score data from a tissue matched, non-tumor sample. If the subject's signature gene expression level is greater than the control or threshold, the subject's tumor is indicated as having a cytotoxic gene signature.

In some embodiments, the control level or the predetermined threshold value is derived from tumor-infiltrating CD4+ T-cells, e.g., by evaluating a cohort of matched tumor samples. By way of example but not by way of limitation, in some embodiments, a control level or threshold level is determined from expression scores derived from single cell sequencing of the tumor-infiltrating CD4+ T-cells of the cohort samples. Thus, in some embodiments, if the subject's expression score is equal to or higher than the control scores, the subject's tumor is indicated as having a cytotoxic gene signature.

In some embodiments, the predetermined threshold comprises a geometric mean calculated from the expression scores of the signature genes in the CD4+ T-cells of the cohort samples. Thus, in some embodiments, a geometric mean is calculated from the expression score data of the signature genes in the patient's sample and compared to the geometric mean of the threshold geometric mean. If the subject's geometric mean is higher than the threshold geometric mean, the subject's tumor is identified as having a cytotoxic gene signature.

In some embodiments, "control" IO Response Profiles are derived by comparing the level of signature gene expression in several tumor samples of the same type as the subject's tumor, from a cohort of different subjects. In some embodiments, the cohort of subjects have been treated with one or more checkpoint inhibitors and have been classified as having a favorable outcome, or an unfavorable outcome. The signature gene expression level of cohort subjects showing no or negligible response to the therapeutic agent (unfavorable outcome) will be considered "low" and indicative of resistance (or non-responsiveness) to a therapeutic drug. Conversely, the signature gene expression level of cohort subjects showing a positive response to the therapeutic agent (favorable outcome) will be considered "elevated" and indicative of susceptibility (or responsiveness) to a therapeutic drug. In some embodiments, a control gene signature comprises a continuum of expression levels, that are correlated with therapeutic response, e.g., to a checkpoint inhibitor. In some embodiments, the cohort of subjects have been determined to have HLA-LOH.

In some embodiments, the subject's signature gene expression levels are compared within the cohort(s) and correlated with response to the one or more therapeutic agents, (e.g., one or more checkpoint inhibitors).

In some embodiments, the level of signature gene expression in a tumor sample is correlated with checkpoint inhibitor used (or no chemotherapy) and overall survival in a continuous fashion. In some embodiments, every unit increase in the level of signature gene expression is correlated to a corresponding increase in survival of patients treated with a checkpoint inhibitor. Therefore, in some embodiments, an incremental trend in baseline level of signature gene expression is predictive of response to checkpoint inhibitor in a continuous fashion.

In some embodiments, a given patient tumor sample will comprise zero, low, medium, or high expression levels (e.g., RNA or protein) of a subset of the genes in Table 1. In some embodiments, the level of expression of the signature genes is directly correlated with the level of cytotoxic immune cells in the tumor sample. In some embodiments, the higher the expression level of the selected signature genes (e.g., the first 20, 25, 27 genes of Table 1), the more likely it is the patient will respond well to a checkpoint inhibitor therapy, especially if the subject has been identified as having HLA-LOH. That is, subjects with tumors expressing high levels of signature genes (e.g., the first 25 genes listed in Table 1) are most likely to respond favorably to a checkpoint inhibitor therapy, whereas subjects with a negligible expression levels of signature genes are unlikely to respond favorably. Patients with low or medium levels of signature genes may also respond favorably, now or eventually because, without wishing to be bound by theory, the cytotoxic immune cell population within the tumor may expand. Mature T cells become activated by recognizing a processed foreign antigen presented by a self-WIC molecule and begin dividing rapidly in response. This proliferation of T cells is called clonal expansion and is necessary to mount a strong immune response. While an initial response to checkpoint inhibitor may appear to be insufficient, the response may increase with increased immune cell stimulation.

Thus, in some embodiments, by determining a subject's level of expression of signature genes of an IO Response Profile (e.g., the first 20, 25, 27 genes of Table 1) and comparing the expression level to a control, threshold, or baseline level, a determination can be made regarding the tumor's resistance or susceptibility to one or more chemotherapeutic drugs, or to a class of chemotherapeutic drugs (e.g., checkpoint inhibitors). This information can then be used, combined with clinical data (such as sex, age, height, weight, prior medical history, prior and current treatments or therapies, molecular/genetic data, tumor type, tumor stage, etc.) to assist physicians in more accurately directing treatment. Additionally or alternatively, this information can combined with a TMB score to derive an IO Progression Risk. In some embodiments, control, threshold, or baseline levels may be determined from tumor tissue or matched wild-type tissue from the same subject, different subjects, or from cohort of subjects. In some embodiments, the control, baseline, or threshold level is 0 or negligible detection by any of the methods described herein.

Methods

A variety of techniques may be used to determine whether a tumor sample comprises a cytotoxic gene signature, including single cell RNA sequencing (see, e.g., Example 1), whole-transcriptome RNA sequencing (see, e.g., Example 3), and immunohistochemistry (IHC) staining (see, e.g., Example 2). Other methods may also be used to identify a cytotoxic gene signature in a tumor sample, for example, the polymerase chain reaction (e.g., reverse-transcription polymerase chain reaction), Western blotting, Northern blotting, cell sorting of tissue samples to identify immune cells such as CD4+ T cells and evaluating the sorted cells for expression of signature genes, etc.

In some embodiments, single cell RNA sequencing is used. In some embodiments, the presence or absence of a cytotoxic gene signature is assessed by comparing the CD4+ T cell transcriptional program of a tumor sample to the cytotoxic gene signature described in Table 1 (e.g., to a subset of the genes of Table 1). In some embodiments, CD4+ T cell cytotoxicity is assessed by identifying the top 2 genes, the top 5 genes, the top 10 genes, the top 20 genes, the top 30 genes, the top 40 genes, the top 50 genes, the top 60 genes, the top 70 genes, the top 80 genes, the top 90 genes, the top 100 genes, or the top genes using a threshold cutoff of an integer between 2 and 100 inclusive. Exemplary genes and their weights with respect to CD4+ cytotoxicity are listed in Table 1 and are described further in Example 1 below. In some examples, the CD4+ T cell cytotoxic gene signature comprises PRF1, GZMA, GZMH, and GNLY.

Additionally or alternatively, methods to identify the presence or absence of a cytotoxic gene signature in a tumor sample from a subject may include methods to identify the proteins expressed by one or more genes of Table 1. Such methods include, but are not limited to: immunoassays assays, such as ELISA and Western blotting; chromatographic methods; and protein mass spectrometry assays. Antibodies that bind to specific proteins are well-known in the art and some are commercially available, as are ELISA kits.

Additionally or alternatively, methods to identify the presence or absence of a cytotoxic gene signature in a tumor sample may include methods of evaluating a subject's tumor RNA levels, e.g., identifying one or more RNA sequences expressed from one or more of the genes listed in Table 1. Methods to detect RNA are well known in the art, and numerous kits and options are commercially available. By way of example but not by way of limitation, methods include reverse transcription and polymerase chain reaction, (RT-PCR), and methods employing direct oligonucleotide probe hybridization to a particular RNA e.g., Northern blotting.

In some embodiments, the presence or absence of a cytotoxic gene signature may be determined in the course of sequencing the nucleic acids (e.g., whole transcriptome RNA sequencing) from a patient's tumor sample. For example, by comparing the expression profile of selected signature genes from Table 1 present in a patient's tumor sample to a reference profile of non-cytotoxic cells (see, e.g., Table 1), one can quickly and easily determine whether a the patient's tumor has been infiltrated by cytotoxic immune cells, such as CD4+ T cells. The presence of these cells is associated with better outcomes for patients treated with immunotherapy, e.g., immune checkpoint blockade. Thus, a physician can use this information to prescribe suitable therapy for the patient. Accordingly, the tumor-infiltrating immune cell population of various cancers may be analyzed in order to determine whether they present a cytotoxic gene signature. Depending on the signature, one or more therapeutic options for a patient are provided.

As discussed above, the present disclosure also relates to calculating an IO Progression Risk, which is determined by evaluating the CYT score and TMB scores, compared to their respective threshold values. The systems and methods disclosed herein comprise a predictive algorithm that analyze TMB and CYT measurements associated with a patient specimen to generate a score reflecting probability of a progression event occurring in 3 months and a score reflecting probability of a progression event occurring in 6 months. This score is converted to categories based on a predefined operating point (for example, a user defined threshold) and results are reported to physicians as either 'increased progression risk' or 'no increased progression risk detected' to help the clinician interpret patient symptoms and cross-sectional imaging for monitoring of IO treated patients.

Exemplary methods to determine CYT scores are discussed above.

TMB (TMB score) may be determined by methods known in the art, or for example, as described in U.S. application Ser. No. 16/789,288 and published as U.S. Pub. No. 2020/0258601 titled Targeted-Panel Tumor Mutational Burden Calculation Systems And Methods and filed Feb. 12, 2020, herein incorporated by reference in its entirety. In some embodiments, TMB is calculated from mutations identified in a subject's DNA. In some embodiments, TMB is calculated from mutations identified in a subject's RNA. In some embodiments, TMB is calculated from mutations identified in a subject's DNA and RNA.

In some embodiments, a panel of genes is sequenced to determine TMB. In some embodiments, the panel includes 100-1000 genes. In some embodiments, the panel includes about 200, 300, 400, 500, 600, 700, 800, or about 900 gene. In some embodiments, the panel comprises at least about 650 genes. In some embodiments, the panel comprises one or more genes selected from the group consisting of ABCB1, ABCC3, ABL1, ABL2, FAM175A, ACTA2, ACVR1, ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf34, CALR, CARD11, CARM1, CASP8, CASR, CBFB, CBL, CBLB, CBLC, CBR3, CCDC6, CCND1, CCND2, CCND3, CCNE1, CD19, CD22, CD274, CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYNC2H1, EBF1, ECT2L, EGF, EGFR, EGLN1, EIF1AX, ELF3, TCEB1, C11orf30, ENG, EP300, EPCAM, EPHA2, EPHA7, EPHB1, EPHB2, EPOR, ERBB2, ERBB3, ERBB4, ERCC1, ERCC2, ERCC3, ERCC4, ERCC5, ERCC6, ERG, ERRFI1, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANCI, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOXP1, FOXQ1, FRS2, FUBP1, FUS, G6PD, GABRA6, GALNT12, GATA1, GATA2, GATA3, GATA4, GATA6, GEN1, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HIST1H1E, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDO1, IFIT1, IFIT2, IFIT3, IFNAR1, IFNAR2, IFNGR1, IFNGR2, IFNL3, IKBKE, IKZF1, IL10RA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEF1, LMNA, LMO1, LRP1B, LYN, LZTR1, MAD2L2, MAF, MAFB, MAGI2, MALT1, MAP2K1, MAP2K2, MAP2K4, MAP3K1, MAP3K7, MAPK1, MAX, MC1R, MCL1, MDM2, MDM4, MED12, MEF2B, MEN1, MET, MGMT, MIB1, MITF, MKI67, MLH1, MLH3, MLLT3, MN1, MPL, MRE11A, MS4A1, MSH2, MSH3, MSH6, MTAP, MTHFD2, MTHFR, MTOR, MTRR, MUTYH, MYB, MYC, MYCL, MYCN, MYD88, MYH11, NBN, NCOR1, NCOR2, NF1, NF2, NFE2L2, NFKBIA, NHP2, NKX2-1, NOP10, NOTCH1, NOTCH2, NOTCH3, NOTCH4, NPM1, NQO1, NRAS, NRG1, NSD1, WHSC1, NT5C2, NTHL1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCD1LG2, PDGFRA, PDG-FRB, PDK1, PHF6, PHGDH, PHLPP1, PHLPP2, PHOX2B, PIAS4, PIK3C2B, PIK3CA, PIK3CB, PIK3CD, PIK3CG, PIK3R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2R1A, PPP2R2A, PPP6C, PRCC, PRDM1, PREX2, PRKAR1A, PRKDC, PARK2, PRSS1, PTCH1, PTCH2, PTEN, PTPN11, PTPN13, PTPN22, PTPRD, PTPRT, QKI, RAC1, RAD21, RAD50, RAD51, RAD51B, RAD51C, RAD51D, RAD54L, RAF1, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNX1T1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SMAD2, SMAD3, SMAD4, SMARCA1, SMARCA4, SMARCB1, SMARCE1, SMC1A, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STATE, STK11, SUFU, SUZ12, SYK, SYNE1, TAF1, TANC1, TAP1, TAP2, TARBP2, TBC1D12, TBL1XR1, TBX3, TCF3, TCF7L2, TCL1A, TERT, TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, C10orf54, WEE1, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, and ZRSR2. In some embodiments, a panel comprises each of the above-listed genes. In some embodiments, a panel consists of each of the above genes.

In some embodiments, TMB is calculated as the number of non-synonymous somatic mutations identified in the panel divided by the amount of DNA sequenced, using, for example, the variant annotation output from a tumor-normal matched targeted sequencing panel for oncology patient specimens and the bioinformatics variant calling pipeline corresponding to the sequencing panel (see, for example Beaubier et al., (2019) (Equation 1, below). Somatic variants are defined as non-synonymous if the variant results in change to the amino acid sequence of the protein.

$$TMB = \frac{(\text{number of non-synonymous somatic mutations})}{(\text{megabases of DNA sequenced})}$$

Equation 1

Thus, in some embodiments, TMB is calculated as the integer number of non-synonymous somatic mutations divided by the number of megabases of genomic DNA (e.g., using, for example, the variant annotation output from a tumor-normal matched targeted sequencing panel for oncology patient specimens and the bioinformatics variant calling pipeline corresponding to the sequencing panel). In some embodiments, the TMB calculation does not include synonymous mutations. In some embodiments, the TMB calculation does include synonymous mutations. In some embodiments, the variant annotation output is from a tumor only targeted sequencing panel for oncology patient specimens and the bioinformatics variant calling pipeline corresponding to the sequencing panel.

Once TMB and CYT scores are obtained, the scores are compared to predetermined threshold levels, and an IO Progression Risk can be identified, for example, as shown in Table 2, above.

By way of example only and not by way of limitation, a TMB score can be determined as follows: (1) using NGS methods, sequencing the patient's germline specimen (such as a saliva or blood specimen) to identify sequences of nucleotides in the germline specimen using the targeted-panel to generate germline sequencing results; (2) sequencing the patient's somatic specimen (such as a tumor sample) to identify sequences of nucleotides in the somatic specimen using the targeted-panel to generate somatic sequencing results; (3) quality control (QC) testing on the germ line sequencing results to generate a germline QC score and on the somatic sequencing results to generate a somatic QC score; (4) optionally, generating at least one clinical report, wherein the clinical report comprises a tumor mutational burden (TMB) score associated with the patient, wherein the TMB score is based at least in part on the identified sequences of nucleotides in the germline specimen and identified sequences of nucleotides in the somatic specimen, and wherein the TMB score is calculated from: (i) mutations in the germ line sequencing results and a panel size of the targeted panel when the germline QC score is above a passing threshold and the somatic QC score is below a passing threshold; (ii) mutations in the somatic sequencing results and the panel size of the targeted-panel when the somatic QC score is above the passing threshold and the germline QC score is below the passing threshold; and (iii) mutations in the somatic sequencing results, mutations in the germline sequencing results, and the panel size of the targeted-panel when the somatic QC score is above the passing threshold and the germline QC score is above the passing threshold.

Cancers

A cytotoxic gene signature and IO Progression Risk may be tested for and identified in any number of tumor types. Thus, the methods, systems, and compositions described herein are not limited to the tumor types exemplified herein (e.g., bladder cancer, non-small cell lung cancer, colorectal cancer, and liver cancer). Any solid tumor may be tested for a cytotoxic gene signature, which indicates the presence of infiltrating immune cells, including cytotoxic CD4+ T-cells, and for IO Progression Risk. For example, the tumor-infiltrating immune cell population of any solid tumor cancer may be analyzed in order to determine whether cytotoxic gene signature is present in the sample and to determine the TMB. Once both CYT and TMB are compared to a threshold CYT and TMB value, an IO Progression Risk can be determined. One or more therapeutic options for a patient may be determined based on the presence of absence of cytotoxic immune cells in the tumor sample and/or the relative level of these cells in the tumor sample, as correlated to the level of expression of the selected cytotoxic signature genes, and/or based on the IO Progression Risk.

In some embodiments, the subject is suffering from cancer and has or is suspected of having a loss of heterozygosity in a HLA gene (HLA-LOH). When HLA-LOH occurs in the class I HLA locus in the tumor, CD8+ T cells are no longer able to recognize and kill tumor cells. Studies have shown that this is a common mechanism of immune escape and is associated with worse outcomes for patients treated with immunotherapy, e.g., immune checkpoint blockade (4,5). Surprisingly, however, some patients with HLA-LOH do respond to immunotherapy as measured by progression free survival. Here, the inventors demonstrate that a cytotoxic gene signature is a strong indicator of favorable response to immune checkpoint blockade therapy in patients with HLA-LOH. HLA-LOH may be identified by performing genomic profiling (e.g., using single cell RNA sequencing, or whole-transcriptome RNA sequencing) on a tumor sample collected from the patient. In some embodiments, the same genomic profiling assay may be used both to determine whether a patient has a HLA-LOH and to assess the cytotoxicity of any immune cells that have infiltrated the tumor.

A patient may have an HLA-LOH affecting any HLA class I protein. By way of example only, but not by way of limitation, the patient may have a loss of function mutation in beta-2-microglobulin (B2M), a gene that encodes the beta chain of MHC class I molecules. B2M mutations have been identified in multiple cancer types, including colorectal, uterine, stomach, lung, skin and head and neck cancer (13). A B2M mutation may suggest that a patient is deficient in HLA-I antigen presentation. However, if a cytotoxic gene signature is identified in the patient's tumor, the patient may still be an appropriate candidate for immunotherapy (i.e., checkpoint inhibitor therapy).

As used herein, "stage 0 cancer" refers to a situation in which there is no cancer, but abnormal cells are present, with the potential to become cancerous.

As used herein, "stage I cancer" refers to a small tumor localized to a single site. Stage 1 cancer is also termed "early stage cancer."

As used herein, the term "stage II cancer" refers to a cancer that is larger (has grown) but has not spread to other tissues or organs.

As used herein, the term "stage III cancer" refers to a cancer that is larger (has grown) and that may have spread to other tissues, organs and/or lymph nodes.

As used herein, the term "stage IV cancer" refers to a cancer that has spread from where it started to other parts of the body, and is also termed "metastatic cancer" or "advanced cancer."

Engine for Predicting Response to Immunotherapy and/or IO Progression Risk

In some examples, an engine for predicting a response to immunotherapy may be utilized in accord with patient management. Such an engine may be trained on one or more features associated with a CD4+ T-cell cytotoxic gene signature. Exemplary non-limiting features are described below. In various embodiments, an engine may be retrained, for example, after training data quality control has been performed, different and/or additional training data have been selected, or training data have been otherwise updated or changed.

In some embodiments, computer systems are provided, wherein the computer systems comprise one or more processors, and memory storing one or more programs for execution by the one or more processors. In some embodiments, one or more models are also provided in the computer system. In some embodiments, the one or more models are individually or collectively trained to provide output data (for example, a binary output, or a continuous output), wherein the output data is derived from input data to which the one or more models are applied. The output data may be used to determine whether a patient is likely to respond to IO therapy (including checkpoint inhibitor) or likely to experience a progression event within a specified amount of time of starting to receive IO therapy. By way of example, input data may comprise, in electronic form, nucleic acid data, such as sequence reads, and features derived from the nucleic acid data. Input data may also comprise clinical information, genetic information, treatment information, treatment outcome information, tumor-specific information (origin, cancer type, size, description, growth rate, etc.), and the like. Input data may comprise HLA class I gene status, and/or tumor mutation burden information. Additional exemplary features that may be input into the system are described below.

Cytotoxic immune cell IHC feature: A binary feature describing the presence or absence of a cytotoxic gene signature or a continuous feature describing the percentage of cytotoxic immune cells of all immune cells can be generated based on the IHC scoring. In some embodiments, the cytotoxic cell comprises CD4+ T cells.

Tumor HLA-I and/or HLA-II expression IHC feature: A binary feature describing the presence or absence of HLA-1 and/or HLA-II expressing tumor cells or a continuous feature describing the percentage of HLA-1 and/or HLA-II expressing tumor cells of all tumor cells can be generated based on the IHC scoring.

Cytotoxic immune cell bulk RNAseq feature: A continuous feature representing the amount of cytotoxic immune cells (e.g., CD4+ T cells) in the sequencing sample can be generated as described, for example, in FIG. 1. Binarized versions of this feature can be generated by thresholding the continuous features, based on characteristics of the distribution like mean or median, associations with clinical or other genomic features, or by other methods.

The cytotoxic CD4 features can be used alone or combined with clinical and/or genomic (DNA), transcriptomic (RNA), or other molecular features to create a feature set for model training. Examples of features may include TMB (continuous and/or binary), driver vs. passenger status of a variant, HLA LOH, immune repertoire sequencing (for example, TCR and/or BCR sequencing), single-cell data (for example, single-cell DNA and/or RNA sequencing, FACS, single-cell surface protein analysis, single-cell TCR profiling, etc. see FIG. 4A), Resistance gene mutation status, Pathway mutation status, Co-mutation status, Somatic signatures, CD274 (PDL1) expression, Other checkpoint gene expression, Published IO RNA gene signatures, including CYT index, (Rooney, M. S., Shukla, S. A., Wu, C. J., Getz, G. & Hacohen, N. Molecular and Genetic Properties of Tumors Associated with Local Immune Cytolytic Activity. Cell 160, 48-61 (2015)), GEP score (Ayers, M. et al. IFN-γ-related mRNA profile predicts clinical response to PD-1 blockade. J Clin Invest 127, 2930-2940 (2017).), IMPRES (Auslander, N. et al. Robust prediction of response to immune checkpoint blockade therapy in metastatic melanoma. Nat Med 24, 1545-1549 (2018).), Roh score (Roh, W. et al. Integrated molecular analysis of tumor biopsies on sequential CTLA-4 and PD-1 blockade reveals markers of response and resistance. Sci Transl Med 9, eaah3560 (2017)), NRS score (Huang, A. C. et al. A single dose of neoadjuvant PD-1 blockade predicts clinical outcomes in resectable melanoma. Nat Med 25, 454-461 (2019)). Differentially expressed genes determined by comparing expression levels of progressors and non-progressors at 6 months (or other time periods), Pathway expression, WGCNA gene modules, HLA expression.

In one embodiment, each training RNA data set (for example, each set of RNA data may be associated with a unique RNA sequencing run performed on RNA isolated from a unique specimen and/or cDNA associated with that isolated RNA) used to train the IO Progression Risk model may be associated with a continuous TMB score (for example, number of mutations per sequenced megabase). In another embodiment, each training RNA data set may be associated with a binary TMB score (for example, 1 if TMB is above the TMB threshold and 0 if TMB is below the TMB threshold). In various embodiments, the TMB scores associated with any two training RNA data sets Classification models, such as regularized logistic regression or support vector machines (SVM), can be used to predict progression within a particular time interval after the initiation of an immunotherapy regimen.

Survival models, such as Cox Proportional-Hazards and survival SVMs, can be used to predict the progression free survival, overall survival or time to progression after the initiation of an immunotherapy regimen.

Figure 19:
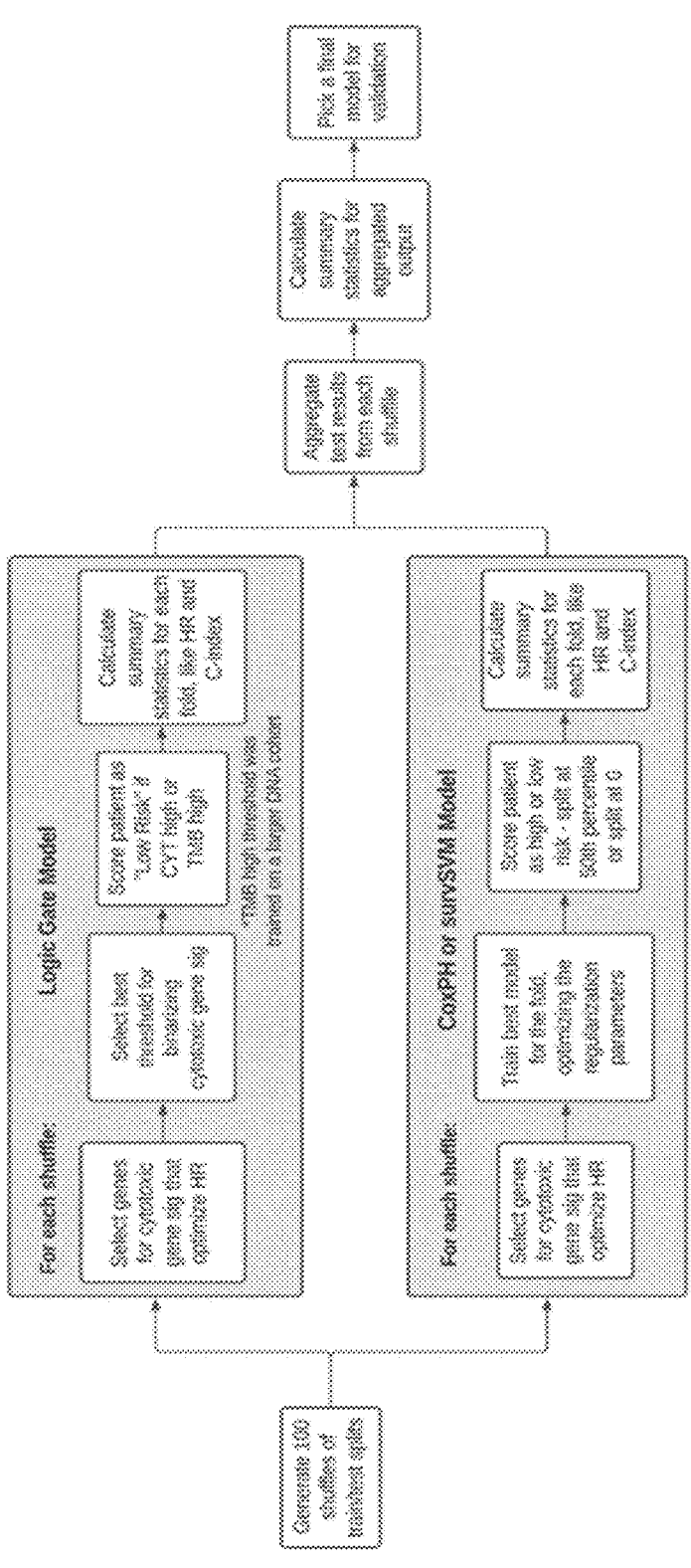
FIG. 19 illustrates one example approach for training an IO Progression Risk prediction model.

In some embodiments, the systems and methods include an IO Progression Risk predictor that uses outputs generated from two laboratory developed tests (LDTs): a targeted panel DNA sequencing assay (for example, targeting approximately 650 genes) and a whole exome capture RNA sequencing (RNA-seq) assay. The output of the DNA sequencing assay is used to calculate tumor mutational burden (TMB) (see U.S. application Ser. No. 16/789,288 published as U.S. Pub. No. 2020/0258601) and the output of the RNA-seq assay is used to calculate cytotoxicity of tumor infiltrating immune cells (CYT). (See, for example, Example 5; FIG. 19).

Methods of Treatment

The present invention also provides methods for treating cancer. The methods utilize as assessment of the cytotoxicity of the tumor-infiltrating immune cells to predict whether the patient will respond favorably or unfavorably to a checkpoint inhibitor therapy. If the patient's tumor sample comprises a significant number of cytotoxic immune cells (as determined by identifying a cytotoxic gene signature, a CYT score or CS above threshold or above control levels), the patient is deemed likely to respond favorably to a checkpoint inhibitor therapy, whereas if the patient's tumor sample comprises a low number of cytotoxic immune cells (as determined by identifying a low expression cytotoxic gene signature), the patient is deemed likely to respond unfavorably to a checkpoint inhibitor therapy.

Accordingly, determining the susceptibility of a subject's tumor tissue to a chemotherapeutic agent such as a checkpoint inhibitor allows for more effective treatment, resulting in increased survival time, tumor regression, or complete or partial remission, for subjects suffering from various forms of cancer.

A used herein, a "favorable response" or "favorable outcome" refers to a response to therapy that includes reducing, alleviating, inhibiting or preventing one or more cancer symptoms, reducing, inhibiting or preventing the growth of cancer cells, reducing, inhibiting or preventing metastasis of the cancer cells or invasiveness of the cancer cells or metastasis, or reducing, alleviating, inhibiting or preventing one or more symptoms of the cancer or metastasis thereof, longer progression free survival time, or increasing the survival time of the patient, as compared to an appropriate control. By contrast, an "unfavorable response" or "unfavorable outcome" is any response that does not result in any of the above-mentioned effects.

As used herein, the term or "immuno-oncology treatment" or "IO treatment" is used to refer to a cancer treatment that stimulates the patient's immune system to destroy cancer cells. An exemplary IO therapy comprises checkpoint inhibitors.

In some embodiments, subjects with cancer and at risk of or diagnosed with HLA-LOH may be candidates for one or more checkpoint inhibitor therapies. As used herein, the term "checkpoint inhibitor" refers to molecules that totally or partially reduce, inhibit, interfere with or modulate one or more checkpoint proteins. Checkpoint proteins and their ligands are expressed by certain types of immune cells (e.g., T cells, macrophages) as well as by some cancer cells. Checkpoint proteins serve to keep immune responses in check. However, they also inhibit the activation of T cells, thereby preventing them from responding to or killing cancer cells. Immune checkpoint activation can also limit the duration and intensity of T cell responses. Checkpoint inhibitor therapies commonly work by binding to a checkpoint protein and blocking its ability to interact with T cells. When checkpoint proteins are blocked, their suppressive effect on the immune system is released, allowing T cells to respond to tumor antigens and kill cancer cells. In the clinic, checkpoint inhibitors, such as anti-PD1 antibodies and anti-CTLA-4 antibodies, have shown a great deal of promise in treating certain cancers.

Common checkpoint inhibitor protein targets include, for example, cytotoxic T-lymphocyte-associated protein 4 (CTLA4; also known as CD152), programmed cell death 1 (PD-1), PD-1 ligand 1 (PD-L1), lymphocyte activation gene-3 (LAG-3), 4-1BB (also known as CD137), B7-H3, OX40, and T-cell immunoglobulin and mucin domain-3 (TIM3). Checkpoint inhibitors are commonly antibodies or derivatives of antibodies. Checkpoint blockade may include immune reactivation. The immune oncology (IO) response models built using the cytotoxic CD4+ features can potentially be applied to any checkpoint inhibitor regimen that is used to treat solid tumors. Suitable regimens include those that utilize checkpoint inhibitors such as pembrolizumab, nivolumab, ipilimumab, atezolizumab, cemiplimab, durvalumab, and avelumab. A checkpoint inhibitor therapy can be administered with another checkpoint inhibitor therapy, or may be administered with another cancer therapy (e.g., radiation, surgery, other chemotherapeutics, etc.). Exemplary checkpoint inhibitor combination therapies include but are not limited to the ipilimumab and nivolumab regimen.

In some embodiments, the checkpoint inhibitor is administered as part of a combination therapy. Suitable combination therapies include, for example, pembrolizumab, paclitaxel, and carboplatin; pembrolizumab, nab-paclitaxel, and carboplatin; pembrolizumab, pemetrexed, and carboplatin; atezolizumab, bevacizumab, paclitaxel, and carboplatin; or ipilimumab and nivolumab.

The checkpoint inhibitors used with the present invention should be administered in a therapeutically effective amount. The terms "effective amount" or "therapeutically effective amount" refer to an amount sufficient to effect beneficial or desirable biological or clinical results. That result can be reducing, alleviating, inhibiting or preventing one or more symptoms of a disease or condition, reducing, inhibiting or preventing the growth of cancer cells, reducing, inhibiting or preventing metastasis of the cancer cells or invasiveness of the cancer cells or metastasis, or reducing, alleviating, inhibiting or preventing one or more symptoms of the cancer or metastasis thereof, or any other desired alteration of a biological system. In some embodiments, the effective amount is an amount suitable to provide the desired effect, e.g., anti-tumor response. An anti-tumor response may be demonstrated, for example, by a decrease in tumor size or an increase in immune cell activation (e.g., CD8+ or CD4+ T cell activation).

Methods for determining an effective means of administration and dosage are well known to those of skill in the art and will vary with the formulation used for therapy, the purpose of the therapy, the target cell being treated, and the subject being treated. Single or multiple administrations can be carried out with the dose level and pattern being selected by the treating physician. For example, the checkpoint inhibitor pembrolizumab is typically administered in 200 mg doses every 3 weeks or 400 mg doses every 6 weeks for the treatment of NSCLC. Similarly, when pembrolizumab is administered in combination with paclitaxel and carboplatin it is typically administered in 200 mg doses every 3 weeks or 400 mg doses every 6 weeks.

As described above, therapeutic compositions disclosed herein include checkpoint inhibitors. Such compositions can be formulated and/or administered in dosages and by techniques well known to those skilled in the medical arts taking into consideration such factors as the age, sex, weight, tumor type and stage, condition of the particular patient, and the route of administration.

The compositions may include pharmaceutical solutions comprising carriers, diluents, excipients, preservatives, and surfactants, as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

In some embodiments, compositions are formulated for systemic delivery, such as oral or parenteral delivery. In some embodiments, minimally invasive microneedles and/ or iontophoresis may be used to administer the composition. In some embodiments, compositions are formulated for site-specific administration, such as by injection into a specific tissue or organ, topical administration (e.g., by patch applied to the target tissue or target organ).

The therapeutic composition may include, in addition to checkpoint inhibitor, one or more additional active agents. By way of example, the one or more active agents may include an additional chemotherapeutic drug, an antibiotic, anti-inflammatory agent, a steroid, or a non-steroidal anti-inflammatory drug.

In some embodiments, in addition to one or more therapeutic formulations, a subject is also administered an additional cancer treatment, such as surgery, radiation, immunotherapy, stem cell therapy, and hormone therapy.

In some embodiments, a subject tumor sample with a cytotoxic gene signature expression level higher than a control or a baseline level is treated with one or more checkpoint inhibitors. In some embodiments, the treatment reduces, alleviates, prevents, or otherwise lessens the symptoms of the tumor more quickly or effectively than a subject suffering from the same or similar cancer, but with a tumor cytotoxic gene signature level at or below the control or threshold level. In some embodiments, the baseline level is 0 or negligible detection.

In some embodiments, improvements in the condition of the subject's cancer status and overall health is observed more quickly than if no treatment is provided for the same or similar condition or disease.

In some embodiments, the therapeutic composition comprises a bispecific antibody that targets immune cells, such as cytotoxic CD4+ T cells, to tumors. A bispecific antibody is an artificial protein that can simultaneously bind to two different antigens. For example, the bispecific antibody may have a first domain that binds to a cytotoxic CD4+ T cell-specific cell surface marker and a second domain that binds to a tumor-specific antigen, thereby bring the T cells into close proximity with the tumor. Exemplary, non-limiting cytotoxic CD4+ T cell markers include CD4, granzymes, and perforin, and exemplary, non-limiting tumor specific antigens include CEA, EpCAM, HER2 and EGFR.

With respect to the IO Progression Risk, in some embodiments, a score reflecting probability of a progression event occurring in 3 months and a score reflecting probability of a progression event occurring in 6 months may be provided. This score can then be converted to categories based on a predefined operating point (for example, a user defined threshold) and results are reported to physicians as either 'increased progression risk' or 'no increased progression risk detected.'

Such information will help the clinician interpret patient symptoms, for example, with cross-sectional imaging for monitoring of IO treated patients. In one possible scenario, the clinician could opt for shorter intervals between imaging studies for 'increased risk' subjects, or interpret radiographic changes on cross-sectional imaging with a higher pre-test probability for disease progression and prepare for testing such as CNS imaging and/or transitioning toward the next line of therapy. Accurately refining pre-test probability may inform clinical judgment and lead to better outcomes by identifying progression events sooner, limiting usage of ineffective and costly IO regimens, and improving patient quality of life by potentially transitioning to the next line of therapy before asymptomatic progression becomes symptomatic progression.

Figure 23:
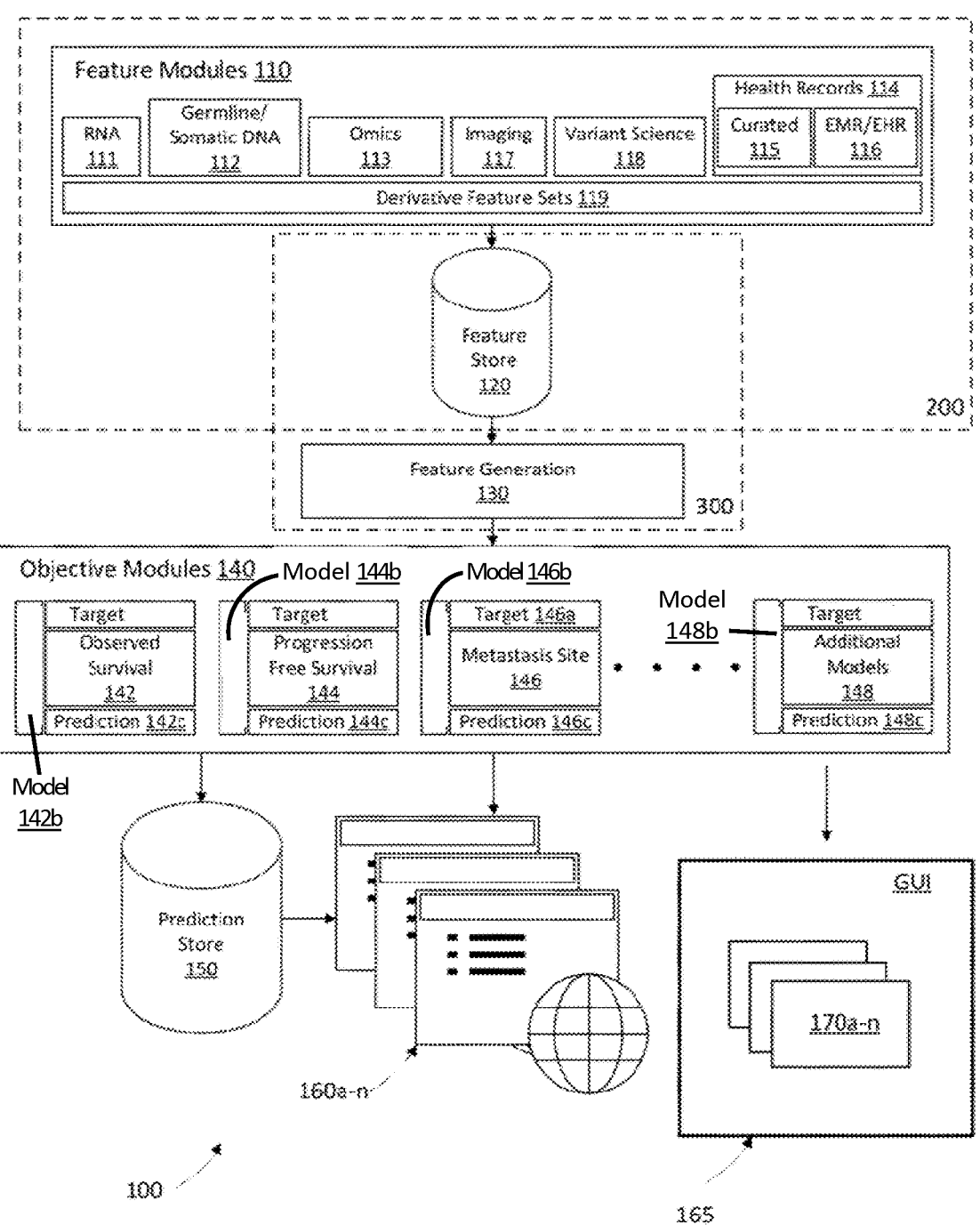
FIG. 23 is a block diagram illustrating a system for generating predictions of an objective from a plurality of patient features, in accordance with some embodiments of the present disclosure.

FIG. 23 illustrates an embodiment of a computer-implemented system 100 for generating and modeling predictions of patient objectives. Predictions may be generated from patient information represented by feature modules 110 implemented by the system architecture 100. The system 100 can be a content server (also referred to as a prediction engine), which is hardware or a combination of both hardware and software. A user, such as a health care provider or patient, is given remote access through the GUI to view, update, and analyze information about a patient's medical condition using the user's own local device (e.g., a personal computer or wireless handheld device). A user can interact with the system to instruct it to generate electronic records, update the electronic records, and perform other actions. The content server is configured to receive various information in different formats and it converts the information into the standardized format that is suitable for processing by modules operation on or in conjunction with the content server. Thus, information acquired from patients' electronic medical records (EMR), unstructured text, genetic sequencing, imaging, and various other information can be converted into features that are used for training a plurality of machine-learning models.

The information acquired, processed, and generated by the content server 100 is stored on one or more of the network-based storage devices. The user can interact with the content server to access the information stored in the network-based storage devices, and the content server can receive user-supplied information, apply the one or more models stored in the network-based storage to the information, and to provide, in an electronic form, results of the model application to the user on a graphical user interface of the user device. The electronic information is transmitted in a standardized format over the computer network to the users that have access to the information. In this way, the users can readily adapt their medical diagnostic and treatment strategy in accordance with the system's predictions which can be automatically generated. Moreover, the system generates recommendations to users regarding patient diagnosis and treatment.

In some embodiments, the described systems and methods are implemented as part of a digital and laboratory health care platform. The platform may automatically generate a molecular report as part of a targeted medical care precision medicine treatment. In some embodiments, the system in accordance with embodiments of the present disclosure operates on one or more micro-services, which can be micro-services of an order management system. In some embodiments, the system is implemented in conjunction with one or more micro-services of a cell-type profiling service.

The feature modules 110 may store a collection of features, or status characteristics, generated for some or all patients whose information is present in the system 100. These features may be used to generate and model predictions using the system 100. While feature scope across all patients is informationally dense, a patient's feature set may be sparsely populated across the entirety of the collective feature scope of all features across all patients. For example, the feature scope across all patients may expand into the tens of thousands of features, while a patient's unique feature set may include a subset of hundreds or thousands of the collective feature scope based upon the records available for that patient.

A plurality of features present in the feature modules 110 may include a diverse set of fields available within patient health records 114. Clinical information may be based upon fields which have been entered into an electronic medical record (EMR) or an electronic health record (EHR) 116, which can be done automatically or manually, e.g., by a physician, nurse, or other medical professional or representative. Other clinical information may be curated information (115) obtained from other sources, such as, for example, genetic sequencing reports (e.g., from molecular fields). Sequencing may include next-generation sequencing (NGS) and may be long-read, short-read, or other forms of sequencing a patient's somatic and/or normal genome. A comprehensive collection of features (status characteristics) in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, as shown in FIG. 23, a subset of features may comprise molecular data features, such as features derived from an RNA feature module 111 or a DNA feature module 112 sequencing.

As further shown in FIG. 23, another subset of features, imaging features from imaging feature module 117, may comprise features identified through review of a specimen by pathologist, such as, e.g., a review of stained H&E or IHC slides. As another example, a subset of features may comprise derivative features obtained from the analysis of the individual and combined results of such feature sets. Features derived from DNA and RNA sequencing may include genetic variants from variant science module 118, which can be identified in a sequenced sample. Further analysis of the genetic variants present in variant science module 118 may include steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology-related features.

Features derived from structured, curated, and/or electronic medical or health records 114 may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated with any of the above.

As shown in FIG. 23, the features 113 may be derived from information from additional medical- or research-based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features 117 derived from imaging data may further include reports associated with a stained slide, size of tumor, tumor size differentials over time including treatments during the period of change, as well as machine learning approaches for classifying PDL1 status, HLA status, or other characteristics from imaging data. Other features may include additional derivative features sets 119 derived using other machine learning approaches based at least in part on combinations of any new features and/or those listed above. For example, imaging results may need to be combined with MSI calculations derived from RNA expressions to determine additional further imaging features. As another example, a machine-learning model may generate a likelihood that a patient's cancer will metastasize to a particular organ or a patient's future probability of metastasis to yet another organ in the body. Additional derivative feature sets are discussed in more detail below with respect to FIG. 24. Other features that may be extracted from medical information may also be used. There are many thousands of features, and the above-described types of features are merely representative and should not be construed as a complete listing of features.

In addition to the above features and enumerated modules, the feature modules 110 may further include one or more of the modules that are described below and that can be included within respective modules of the Feature modules 110, as a sub-module or as a standalone module.

Continuing with FIG. 23, a germline/somatic DNA feature module 112 may comprise a feature collection associated with the DNA-derived information of a patient and/or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module 111 may comprise a feature collection associated with the RNA-derived information of a patient, such as transcriptome information. These features may include, for example, raw sequencing results, transcriptome expressions, genes, mutations, variant calls, and variant characterizations. Features may also include normalized sequencing results, such as those normalized by TMP.

The feature modules 110 can comprise various other modules. For example, a metadata module (not shown) may comprise a feature collection associated with the human genome, protein structures and their effects, such as changes in energy stability based on a protein structure.

A clinical module (not shown) may comprise a feature collection associated with information derived from clinical records of a patient, which can include records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module, such as, e.g., the imaging module 117, may comprise a feature collection associated with information derived from imaging records of a patient. Imaging records may include H&E slides, IHC slides, radiology images, and other medical imaging information, as well as related information from pathology and radiology reports, which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA, or any of the biomarkers listed in Table 1; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as, e.g., an epigenome module from Omics module 113, may comprise a feature collection associated with information derived from DNA modifications which are not changes to the DNA sequence and regulate the gene expression. These modifications can be a result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as, e.g., a microbiome module from Omics module 113, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as, e.g., a proteome module from Omics module 113, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) (not shown) may also be included in Omics module 113, such as a feature collection (which is a collection of status characteristics) associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous digital image sequence, or a video, can be interpreted as the capture of a single image evolving through time of mutations revealing patient insights.

In some embodiments, a robust collection of features may include all of the features disclosed above. However, predictions based on the available features may include models which are optimized and trained from a selection of fewer features than in an exhaustive feature set. Such a constrained feature set may include, in some embodiments, from tens to hundreds of features. For example, a prediction may include predicting the likelihood a patient's tumor may metastasize to the brain. A model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

The feature store 120 may enhance a patient's feature set through the application of machine learning and/or an artificial intelligence engine and analytics by selecting from any features, alterations, or calculated output derived from the patient's features or alterations to those features. One method for enhancing a patient's feature set may include dimensionality reduction, such as collapsing a feature set from tens of thousands of features to a handful of features. Performing dimensionality reduction without losing information may be approached in an unsupervised manner or a supervised manner. Unsupervised methods may include RNA Variational Auto-encoders, Singular Value Decomposition (SVD), PCA, KernelPCA, SparsePCA, DictionaryLearning, Isomap, Nonnegative Matrix Factorization (NMF), Uniform Manifold Approximation and Projection (UMAP), Feature agglomeration, Patient correlation clustering, KMeans, Gaussian Mixture, or Spherical KMeans. Performing dimensionality reduction in a supervised manner may include Linear Discriminant Analysis, Neighborhood Component Analysis, MLP transfer learning, or tree based supervised embedding.

In one embodiment, a grid search may be performed across a variety of encoding, such as the supervised and unsupervised approaches above, where each encoding is evaluated across a variety of hypertuning parameters to identify the encoding and hyperparameter set which generates the highest dimensionality reduction while retaining or improving accuracy.

In one embodiment, a grid search may identify a dimensionality reduction implemented with tree-based supervised embedding on RNA TPM feature sets for all patients. RNA TPM feature sets may be fit to a forest of decision trees, Such as a forest of decision trees generated from hyperparameters of minimum samples per leaf using a minimum number of 2, 4, 8, 16, 24, 100, or other selected number, a maximum feature set using a percentage of the features which should be used in each tree, the number of trees to be used in the forest, and the number of clusters which may be identified from the reduced dimensionality dataset. Each tree in the forest may randomly select up to the threshold percentage of features and with each selected feature identify the largest split between patients who have metastasis and do not have metastasis. When the feature set includes RNA TPM features, a random selection of genes may include identifying which genes are the most divisive of the random set of selected features, starting the branching from the most divisive gene and successively iterating down the gene list until either the minimum samples per leaf are not met or the maximum features are met. The leaf nodes for each tree include patients who meet the criteria at each branch and are correlated based upon their likelihood to metastasize. Patient membership of each leaf may be evaluated using one-hot KMeans cluster membership counts or a distance of each patient to each of the KMeans centroids/clusters.

In an example, the leaves of each tree are compared to identify which leaves include the same branches or equivalent branches, such as branches that result in the same patients because the genes, while different, are equivalent to each other. Equivalency may be determined when information related to the expression level of a gene may be correlated with, or predicted from, the expression level data associated with one or more other genes. When a gene may be correlated with, or predicted from, one or more other genes, the one or more other genes are defined as proxy genes. The terms proxy genes and equivalent genes may be used interchangeably herein. Identifying the number of same branches, or equivalent branches, for each leaf allows generation of membership for each leaf as it occurs within the individual trees of the forest. Similarly, when KMeans clusters are generated from the collection of leaves, a distance for each patient may be calculated for each patient. An array may be generated having the normalized inverse of each distance for each patient to each KMeans centroid. The array, at this point, may be stored as a reduced dimensionality feature set of RNA TMP features for the set of patients, and the features of reduced dimensionality may be used in any of the predictive methods described herein. In other words, the methods for identifying a prediction of a target/objective pair may be performed having the array of distances for each patient as an input into the artificial intelligence engine described below; including, for example, performing logistic regression to generate a predictive model for a target/objective pair.

The feature store 120 may generate new features from the original features found in feature module 110 or may identify and store insights or analysis derived using the features. The selections of features may be based upon an alteration or calculation to be generated, and may include the calculation of single or multiple nucleotide polymorphisms, insertion or deletions of the genome, a tumor mutational burden, a microsatellite instability, a copy number variation, a fusion, or other such calculations. In an example, an output of an alteration module which may inform future alterations or calculations may include, for example, a finding that a subset of patients categorized as favorable for receiving IO therapy, respond extremely well to the therapy and are found to have one or more CYT scores or a TMB significantly different than other patients also in this category. Therefore, features which may be utilized in such an alteration detection include an evaluation of the subjects genomic profile with respect to Table 1 gene expression and TMB effectors. A model which focuses on enrichment may isolate such variants. Other variants may be isolated with respect to other illness, diseases, or diagnosis through an enrichment alteration module. The feature store selection, alteration, and calculations is discussed below in more detail with respect to FIG. 24.

The feature generation 130 may process features from the feature store 120 by selecting or receiving features from the feature store 120. The features may be selected based on a patient by patient basis, a target/objective by patient basis, or a target/objective by all patient basis, or a target/objective by cohort basis. In the patient by patient basis, features which occur a specified patient's timeline of medical history may be processed. In the target/objective by patient basis, features which occur in a specified patient's timeline which inform an identified target/objective prediction may be processed. In some examples, a model may be selected which optimizes the prediction based upon the features available to the prediction engine at the time of processing/generating a prediction for the patient or a prediction for all of the patients.

Machine learning algorithms (MLAs) include supervised algorithms (such as algorithms where the features/classifications in the dataset are annotated) using linear regression, logistic regression, decision trees, classification and regression trees, Naïve Bayes, nearest neighbor clustering; unsupervised algorithms (such as algorithms where no features/classification in the dataset are annotated) using Apriori, means clustering, principal component analysis, random forest, adaptive boosting; and semi-supervised algorithms (such as algorithms where an incomplete number of features/classifications in the dataset are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training dataset includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise.

Training may include providing optimized datasets as a matrix of feature vectors for each patient, labeling these traits as they occur in patient records as supervisory signals, and training the MLA to predict an objective/target pairing. Artificial NNs are powerful computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art.

In other MLAs, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the dataset. A single instance of the above models, or two or more such instances in combination, may constitute a model for the purposes of models 142*b*, 144*b*, 146*b*, and 148*b*.

Models may also be duplicated for particular datasets which may be provided independently for each objective module 142, 144, 146, and 148. For example, the metastasis site objective module 146 may receive a DNA feature set, an RNA feature set, a combined RNA and DNA feature set, and observational feature set, or a complete dataset comprising all features for each patient. As another example, the metastasis site objective module 146 may receive imaging features extracted from various digital images acquired from analysis of a patient's sample. A model 146 *b* may be generated for each of the potential feature sets or targets 146 *a*. Each module 142, 144, 146, and 148 may be further associated with Predictions 142 *c*, 144 *c*, 146 *c*, and 148 *c*. A prediction may be a binary representation, such as a "Yes—Target predicted to occur" or "No—Target not predicted to occur." Predictions may be a likelihood representation such as "target predicted to occur with 83% probability/likelihood." Predictions may be performed on patient datasets having known outcomes to identify insights and trends which are unexpected. For example, a cohort of patients may be generated for patients with a common cancer diagnosis who have either remained progression free for five years after diagnosis, have progressed within five years after diagnosis, or who have passed away within five years of diagnosis. A prediction model may be associated with an objective for progression free survival (PFS) and a target of PFS within 2 years. The PFS model may identify every event in each patient's history and generate a prediction of whether the patient will be progression free within 2 years of that event. The cohort of patients may generate, for each event in a patient's medical file, the probability that the patient will remain progression free within the next two years, three years, four years, five years, or more and compare that prediction with whether the patient actually was progression free within two years, etc. of the event.

For example, a prediction that a patient may be progression free with a 74% likelihood but in fact progresses within two years may inform the prediction model that intervening events before the progression are worth reviewing or prompt further review of the patient record that lead to the prediction to identify characteristics which may further inform a prediction. An actual occurrence of a target is weighted to 1 and the non-occurrence of the event is weighted to 0, such that an event which is likely to occur but does not may be represented by the difference (0-0.73), an event which is not likely to occur but does may be represented by the difference (0.22-1), to provide a substantial difference in values in comparison to events which are closely predicted (0-0.12 or 1-0.89) having a minimal difference. For determining a prediction, each module 142, 144, 146, and 148 may be associated with a unique set of prior features, forward features, or a combination of prior features and forward features which may be received from feature generation 130.

Prediction store 150 may receive predictions for targets/objectives generated from objective modules 140 and store them for use in the system 100. Predictions may be stored in a structured format for retrieval by a user interface such as, for example, a webform-based interactive user interface which, in some embodiments, may include webforms 160 *a-n*. Webforms may support GUIs that can be displayed by a computer to a user of the computer system for performing a plurality of analytical functions, including initiating or viewing the instant predictions from objective modules 140 or initiating or adjusting the cohort of patients from which the objective modules 140 may perform analytics from. Electronic reports 170 *a-n* may be generated and provided to the user via the graphical user interface (GUI) 165. It should be appreciated that the GUI 165 may be presented on a user device which is connected to the content server/prediction engine 100 via a network.

The reports 170 can be provided to the user as part of a network-based patient management system that collects, converts and consolidates patient information from various physicians and health-care providers (including labs) into a standardized format, stores it in network-based storage devices, and generates messages comprising electronic reports once the reports are generated in accordance with embodiments of the present disclosure. In this way, a user (e.g., a physician, oncologist, or any other health care provider, or a patient, receives computer-generated predictions related to a likelihood of a patient's tumor metastasizing, a predicted location of the metastasis, and/or an associated timeline.

In some embodiments, the electronic report may include a recommendation to a physician to treat the patient using a treatment that correlates with a magnitude of a determined degree of risk of the metastasis, a recommendation to a physician to de-escalate when the patient is low risk to reduce adverse events, save cost and improve health response, or a recommendation to a physician to elect a treatment which provides adjustments to the typical monitoring such as scanning, imaging, blood testing. Additionally or alternatively, the electronic report may include a recommendation for accelerated screening of the patient, a recommendation for consideration of additional monitoring. In some embodiments, an electronic report indicating that a patient may experience metastasis to one or more predicted organs results in researchers planning a clinical trial by predicting which groups of patients are most likely to respond to therapy that targets metastases or recurrences in general or metastases to specific organ sites. In some embodiments, a clinical trial may be performed by selecting patients who are predicted to be more likely or less likely to develop metastases or recurrences in general or metastases to specific organ site, using systems and methods in accordance with the present disclosure.

FIG. 24 illustrates the generation of additional derivative feature sets 119 of FIG. 23 and the feature store 120 using alteration modules. A feature collection 205 may comprise the modules of feature modules 110, stored alterations 210 from the alteration module 250 and stored classifications 230 from the structural variant classification 280. An alteration module 250 may be one or more microservices, servers, scripts, or other executable algorithms 252 *a-n* which generate alteration features associated with de-identified patient features from the feature collection. Exemplary alterations modules may include one or more of the following alterations as a collection of alteration modules 252 *a-n*. An SNP (single-nucleotide polymorphism) module may identify a substitution of a single nucleotide that occurs at a specific position in the genome, where each variation is present to some appreciable degree within a population (e.g., >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in susceptibility to a wide range of diseases (e.g., sickle-cell anemia, β-thalassemia and cystic fibrosis result from SNPs).

The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome. An InDels module may identify an insertion or deletion of bases in the genome of an organism classified among small genetic variations. While usually measuring from 1 to 10,000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint," each individual has microsatellites of a set length. The most common microsatellite in humans is a dinucleotide repeat of the nucleotides C and A, which occurs tens of thousands of times across the genome. Microsatellites are also known as simple sequence repeats (SSRs). A TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. It provides a quantitative measure that can be used to better inform treatment decisions, such as selection of targeted or immunotherapies or enrollment in clinical trials. A CNV (copy number variation) module may identify deviations from the normal genome and any subsequent implications from analyzing genes, variants, alleles, or sequences of nucleotides. CNV are the phenomenon in which structural variations may occur in sections of nucleotides, or base pairs, that include repetitions, deletions, or inversions.

A Fusions module may identify hybrid genes formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

In some embodiments, an IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. For example, in some embodiments, the predictions may include PD-L1 prediction from H&E and/or RNA.

A Therapies module may identify differences in cancer cells (or other cells near them) that help them grow and thrive and drugs that "target" these differences. Treatment with these drugs is called targeted therapy. For example, many targeted drugs go after the cancer cells' inner "programming" that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes. Others boost the way your body fights the cancer cells. This can affect where these drugs work and what side effects they cause.

In some embodiments, matching targeted therapies may include identifying the therapy targets in the patients and satisfying any other inclusion or exclusion criteria. A VUS (variant of unknown significance) module may identify variants which are called but cannot be classified as pathogenic or benign at the time of calling. VUS may be catalogued from publications regarding a VUS to identify if they may be classified as benign or pathogenic. A Trial module may identify and test hypotheses for treating cancers having specific characteristics by matching features of a patient to clinical trials. These trials have inclusion and exclusion criteria that must be matched to enroll which may be ingested and structured from publications, trial reports, or other documentation.

An Amplifications module may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another.

An Isoforms module may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as the number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms.

A Pathways module may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations. A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant classification 280 may evaluate features from feature collection 205, alterations from alteration module 250, and other classifications from within itself from one or more classification modules 282 *a-n*. Structural variant classification 280 may provide classifications to stored classifications 230 for storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules 282 *a-n*. A classifier for clinical trials may include evaluation of variants identified from the alteration module 250 which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, tumor mutational burden, indels, SNP, MINP, fusions, and other alterations which may be classified based upon the results of the alteration modules 252 *a-n*.

Each of the feature collection 205, alteration module 250, structural variant 280 and feature store 120 may be communicatively coupled to data bus 290 to transfer data between each module for processing and/or storage. In another embodiment, each of the feature collection 205, alteration module 250, structural variant 280 and feature store 120 may be communicatively coupled to each other for independent communication without sharing data bus 290.

Various features may be generated and/or derived for a patient. For example, in some embodiments, the features can be related to RNA TPM (transcripts per million) count features. The feature space may comprise expression levels of the RNA for some or all of the coding genes in the sample. The expression is assayed by counting the number of RNA molecules (transcripts) that are present on a per gene basis. To standardize these counts across different experimental and technical conditions, the counts per gene can be corrected by a normalization factor. This factor standardizes the expression data to represent the number of RNA molecules that would be associated with a single gene in a pool of one million molecules, creating a TPM count.

In some embodiments, an input feature in a TPM space is a normalized count with a lower bound of 0, where the value represents the abundance of the transcript. Transcripts over the whole exome (nearly 19K genes) can be considered. For example, in some embodiments, the genes comprise at least one gene from Table 1.

Figure 25:
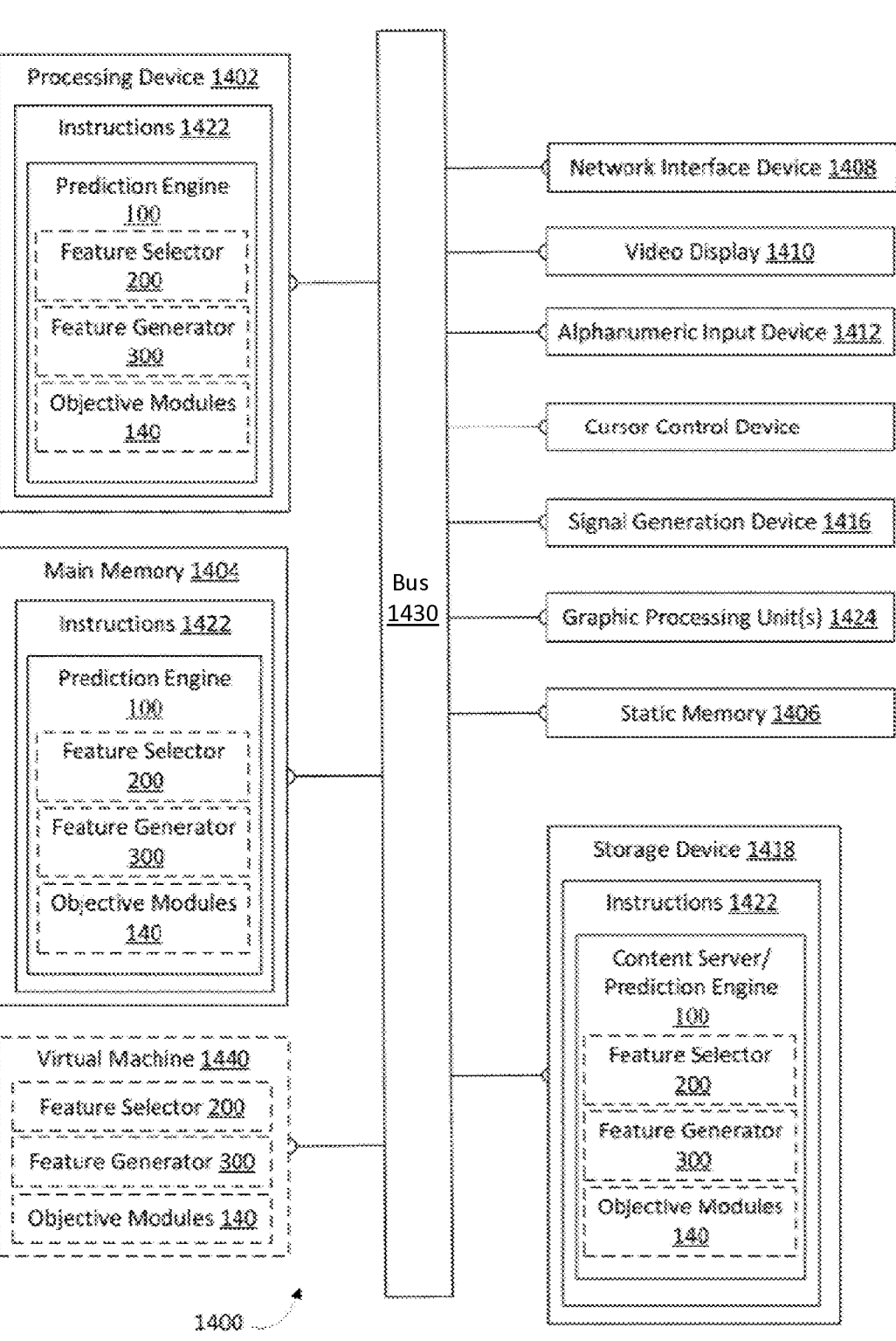
FIG. 25 is a block diagram of an example of a system in which some embodiments of the invention can be implemented.

FIG. 25 is an illustration of an example machine of a computer system 1400 within which a set of instructions, for causing the machine to perform any one or more of the methodologies discussed herein, may be executed. In some implementations, the machine may be connected (such as networked) to other machines in a LAN, an intranet, an extranet, and/or the Internet.

The machine may operate in the capacity of a server or a client machine in client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1400 includes a processing device 1402, a main memory 1404 (such as read-only memory (ROM), flash memory, dynamic random access memory (DRAM) such as synchronous DRAM (SDRAM) or DRAM, etc.), a static memory 1406 (such as flash memory, static random access memory (SRAM), etc.), and a data storage device 1418, which communicate with each other via a bus 1430.

Processing device 1402 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. The processing device 1402 is configured to execute instructions 1422 for performing the operations and steps discussed herein.

The computer system 1400 may further include a network interface device 1408 for connecting to the LAN, intranet, internet, and/or the extranet. The computer system 1400 also may include a video display unit 1410 (such as a liquid crystal display (LCD) or a cathode ray tube (CRT)), an alphanumeric input device 1412 (such as a keyboard), a cursor control device (such as, e.g., a mouse, joystick, or another control device, including a combination device), a signal generation device 1416 (such as, e.g., a speaker), and a graphic processing unit 1424 (such as, e.g., a graphics card).

The data storage device 1418 may be a machine-readable storage medium 1428 (also known as a computer-readable medium) on which is stored one or more sets of instructions or software 1422 embodying any one or more of the methodologies or functions described herein. The instructions 1422 may also reside, completely or at least partially, within the main memory 1404 and/or within the processing device 1402 during execution thereof by the computer system 1400, the main memory 1404 and the processing device 1402 also constituting machine-readable storage media.

In one implementation, the instructions 1422 include instructions for a prediction engine (such as the prediction engine 100 of FIGS. 23-24) and/or a software library containing methods that function as a prediction engine. The instructions 1422 may further include instructions for a feature selector 200 and generator 300 and objective modules 140. While the machine-readable storage medium 1428 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine-readable storage medium as a transitory storage medium or transitory machine-readable storage medium.

In another implementation, a virtual machine 1440 may include a module for executing instructions for a feature selector 200 and generator 300 and objective modules 140. In computing, a virtual machine (VM) is an emulation of a computer system. Virtual machines are based on computer architectures and provide functionality of a physical computer. Their implementations may involve specialized hardware, software, or a combination of hardware and software.

Figure 26:
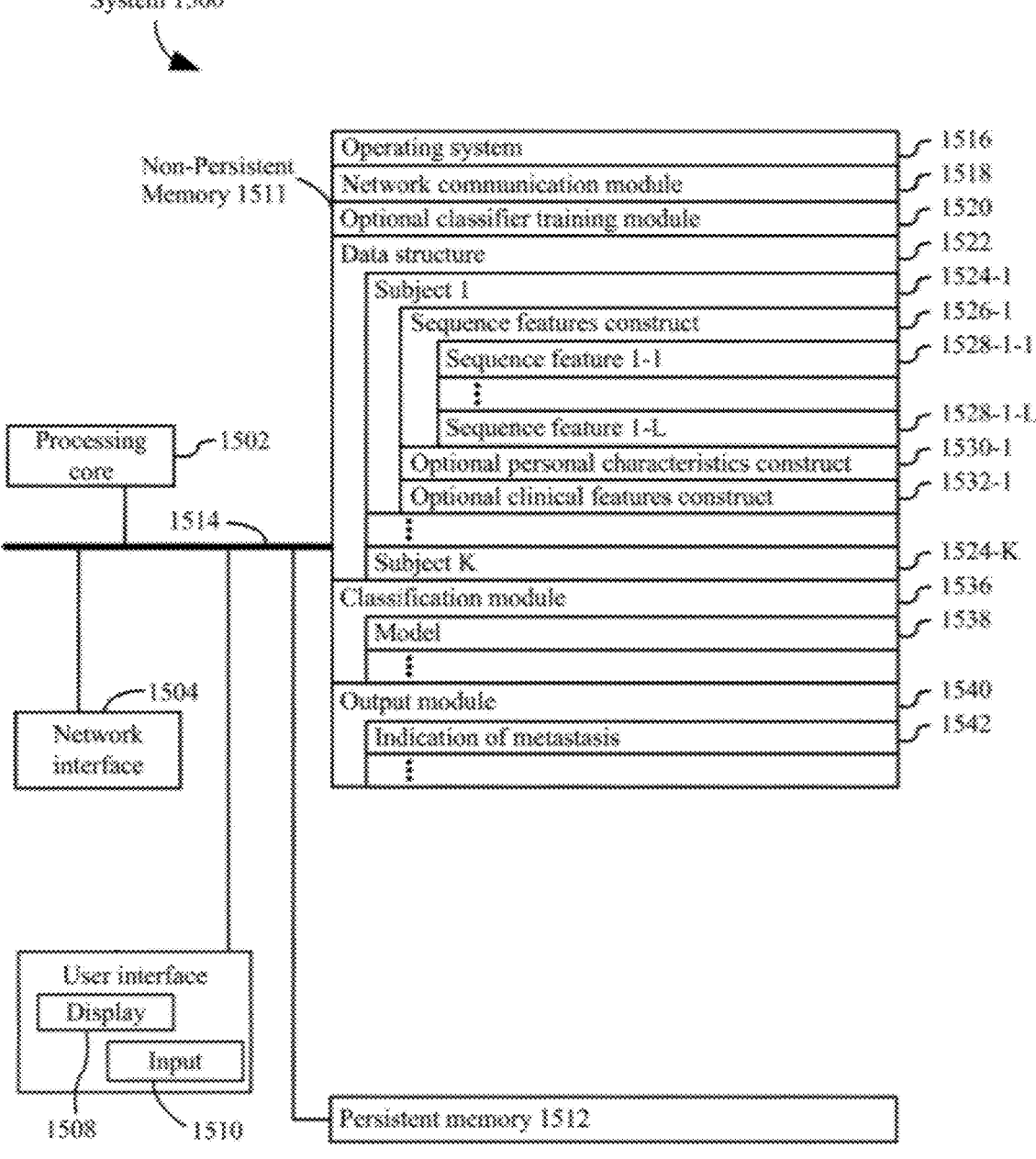
FIG. 26 illustrates a block diagram of an example computing device, in accordance with some embodiments of the present disclosure.

Now that an overview of some aspects of the present disclosure have been provided, details of an exemplary system are described in conjunction with FIG. 26. FIG. 26 is a block diagram illustrating a system 1500 in accordance with some implementations.

The system 1500 in some implementations includes one or more processing units CPU(s) 1502 (also referred to as processors), one or more network interfaces 104, a user interface 106 including (optionally) a display 1508 and an input system 1510, a non-persistent memory 1511, a persistent memory 1512, and one or more communication buses 1514 for interconnecting these components. The one or more communication buses 1514 optionally include circuitry (sometimes called a chipset) that interconnects and controls communications between system components. The non-persistent memory 1511 typically includes high-speed random access memory, such as DRAM, SRAM, DDR RAM, ROM, EEPROM, flash memory, whereas the persistent memory 1512 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 1512 optionally includes one or more storage devices remotely located from the CPU(s) 1502. The persistent memory 1512, and the non-volatile memory device(s) within the non-persistent memory 1512, comprise non-transitory computer readable storage medium.

In some implementations, as illustrated in FIG. 26, the non-persistent memory 1511 or alternatively the non-transitory computer readable storage medium stores the following programs, modules and data structures, or a subset thereof, sometimes in conjunction with the persistent memory 1512:

an optional operating system 1516, which includes procedures for handling various basic system services and for performing hardware dependent tasks;

an optional network communication module (or instructions) 1518 for connecting the system 1500 with other devices and/or a communication network 1504;

an optional classifier training module 1520 for training one or more models (e.g., predictive and/or classification models) to provide one or more indications of whether the subject is likely to respond favorably to IO therapy, e.g., longer time to progression;

a data structure 1522 comprising a plurality of data elements for a cancer of a subject 1524 (e.g., optionally, a plurality of subjects 1524-1, . . . , 1524-K), the data structure 1522 comprising:

a sequence features data construct 1526 (e.g., 1526-1) comprising a first set of sequence features 1528 (e.g., 1528-1-1, . . . , 1528-1-L) (e.g., relative abundance values for the expression of a plurality of genes (e.g., at least one of the genes from Table 1) in a biopsy of the cancer obtained from the subject);

optionally, a personal characteristics data construct 1530 (e.g., 1530-1) comprising one or more personal characteristics about the subject (e.g., age, gender, and/or race); and optionally, a clinical features data construct 1532 (e.g., 1532-1) comprising one or more clinical features related to the diagnosis or treatment of the cancer in the subject and/or one or more temporal elements associated with the one or more clinical features;

a classification module 1536 comprising one or more models 1538 (e.g., optionally, a set of models) that are trained to provide one or more indications of whether the subject will respond favorably to the IO treatment, e.g., checkpoint inhibitor; and an output module 1540 comprising one or more indications 1542 of the subject will respond favorably to the IO treatment, e.g., checkpoint inhibitor.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 1511 optionally stores a subset of the modules and data structures identified above. Furthermore, in some embodiments, the memory stores additional modules and data structures not described above. In some embodiments, one or more of the above identified elements is stored in a computer system, other than that of system 1500, that is addressable by system 1500 so that system 1500 may retrieve all or a portion of such data when needed.

Although FIG. 26 depicts a "system 1500," the figure is intended more as a functional description of the various features that may be present in computer systems than as a structural schematic of the implementations described herein. In practice, and as recognized by those of ordinary skill in the art, items shown separately could be combined and some items could be separated. Moreover, although FIG. 15 depicts certain data and modules in non-persistent memory 1511, some or all of these data and modules instead may be stored in persistent memory 1512 or in more than one memory. For example, in some embodiments, at least data structure 1522 is stored in a remote storage device which can be a part of a cloud-based infrastructure. In some embodiments, at least data structure 1522 is stored on a cloud-based infrastructure. In some embodiments, data structure 1522, the classifier training module 1520, the classification module 1536, and/or the output module 1540 can also be stored in the remote storage device(s). In some embodiments, any of the features of the system 1500 can be used in conjunction with any of the features of any one or more of system 100, system 200, system 300, system 400, system 500, and/or system 1400, as depicted in FIGS. 23-25, and/or any combinations thereof as will be apparent to one skilled in the art. For instance, data structure 1522 can comprise any of the example features listed in systems 400 and 500 or can further be associated with any one or more of feature collection 205, feature module 110, feature store 120, feature selector 200, and feature generator 300.

ILLUSTRATIVE EMBODIMENTS

The following embodiments are illustrative and are not intended to limit the scope of the claimed subject matter.

1. A method for identifying a cytotoxic gene signature in a tumor sample from a subject, the method comprising: a) detecting the expression level of five or more signature genes listed in Table 1 in the tumor sample, wherein detecting comprises one or more of: i) immunohistochemical staining (IHC); ii) single-cell RNA sequencing; and iii) whole transcriptome RNA sequencing; b) comparing the detected expression level to a control level or a predetermined threshold level; and c) optionally, treating the subject with a checkpoint inhibitor.

2. The method of embodiment 1, wherein the signature genes comprise at least the first 5 genes, at least the first 10 genes, at least the first 20 genes, at least the first 25 genes, at least the first 30 genes, at least the first 35 genes, at least the first 40 genes, or at least the first 50 genes of Table 1.

3. The method of embodiment 1, wherein the five or more signature genes comprise the first 10 genes or the first 25 genes of Table 1.

4. The method of any of the previous embodiments, wherein three of the five or more signature genes comprise granzyme B, granzyme K, and perforin.

5. The method of any of the previous embodiments, wherein four of the five or more signature genes comprise granzyme A, granzyme H, granulysin, and perforin 1.

6. The method of any of the previous embodiments, wherein the control level or the predetermined threshold value is derived from healthy matched tissue, or matched tissue know to lack a cytotoxic gene signature.

7. The method of any of the previous embodiments, wherein the control level or threshold level is derived from whole transcriptome expression score data from a tissue matched, non-tumor sample, and detection comprises whole transcriptome sequencing.

8. The method of any of the previous embodiments, wherein the subject's whole transcriptome sequencing provides expression score data, and at least the expression score data of the subject's signature genes are compared to the expression score data of the signature genes of the control; wherein if the subject's expression score data are higher than the control expression score data for each of the five or more signature genes, the subject's tumor is identified as having a cytotoxic gene signature.

9. The method of any of the previous embodiments, wherein the control level comprises protein expression values derived from IHC imaging of the at least 5 signature genes; wherein the detection method comprise IHC and provides protein expression value data; wherein if the subject's protein expression value data are greater than the control protein expression value data, the subject's tumor is identified as having a cytotoxic gene signature.

10. The method of any of the previous embodiments, wherein the control level or the predetermined threshold value is derived from tumor-infiltrating CD4+ T-cells from a cohort of matched tumor samples.

11. The method of any of the previous embodiments, wherein the control level or threshold level is derived from expression scores derived from single cell sequencing of the tumor-infiltrating CD4+ T-cells of the cohort samples.

12. The method of any of the previous embodiments, wherein the predetermined threshold comprises a geometric mean calculated from the expression scores of the signature genes in the CD4+ T-cells of the cohort samples.

13. The method of any of the previous embodiments, wherein the detection method comprises whole transcriptome sequencing that yields expression score data for at least the signature genes, wherein a geometric mean is calculated from the expression score data of the signature genes and compared to the geometric mean of the threshold geometric mean; wherein if the subject's geometric mean is higher than the threshold geometric mean, the subject's tumor is identified as having a cytotoxic gene signature.

14. The method of any of the previous embodiments, wherein the detection method comprises single cell RNA sequencing that yields expression score data, wherein the subject's tumor expression score data for at least the signature genes is compared to the control expression score data for the signature genes; wherein if the subject's expression score data is equal to or greater than the control expression score data, the subject's tumor is identified as having a cytotoxic gene signature.

15. The method of any one of the preceding embodiments, wherein the subject is diagnosed with or suspected of having an altered human leukocyte antigen (HLA) phenotype in a population of tumor cells due to a mutation in at least one HLA class I gene.

16. The method embodiment 15, wherein the population of the subject's tumor cells have a loss of function mutation in at least one HLA class I gene.

17. The method of embodiment 15, wherein the population of the subject's tumor cells have a loss of heterozygosity in at least one HLA class I gene.

18. The method of embodiment 15, wherein the population of the subject's tumor cells have a complete loss of at least one HLA class I gene.

19. The method of any one of the preceding embodiments, wherein the tumor comprises one or more of a non-small cell lung cancer, bladder cancer, colorectal cancer, and liver cancer.

20. The method of any one of the preceding embodiments, wherein the tumor comprises a non-small cell lung cancer.

21. The method of any one of the preceding embodiments, comprising treating the subject with one or more checkpoint inhibitors.

22. The method of embodiment 21, wherein the one or more checkpoint inhibitors are selected from the group consisting of pembrolizumab, nivolumab, ipilimumab, atezolizumab, cemiplimab, durvalumab, and avelumab.

23. The method of embodiment 21 or 22, comprising treating the patient with at least one additional immunomodulatory molecule and/or at least one additional cancer therapeutic.

24. The method of embodiment 23, wherein the at least one additional immunomodulatory molecule and/or at least one additional cancer therapeutic comprises one or more of a T-cell immunoglobulin and mucin domain-3 antibody (TIM3), radiation, surgery, and chemotherapy.

25. The method of any of the preceding embodiments, wherein the cancer sample comprises a solid tumor biopsy from a cancer patient.

26. A method for treating a subject that has been diagnosed with cancer, the method comprising:

a) detecting the expression level of five or more signature genes listed in Table 1 in the tumor sample, wherein detecting comprises one or more of: i) immunohistochemical staining (IHC); ii) single-cell RNA sequencing; and iii) whole transcriptome RNA sequencing; b) comparing the detected expression level to a control level or a predetermined threshold level to identify a cytotoxic gene signature; and c) treating the subject with one or more checkpoint inhibitors if a cytotoxic gene signature is identified.

27. A method of predicting a response to a checkpoint inhibitor therapy in a subject diagnosed with cancer, the method comprising: a) detecting the expression level of five or more signature genes listed in Table 1 in the tumor sample, wherein detecting comprises one or more of: i) immunohistochemical staining (IHC); ii) single-cell RNA sequencing; and iii) whole transcriptome RNA sequencing; b) comparing the detected expression level to a control level or a predetermined threshold level to identify a cytotoxic gene signature; wherein the presence of a cytotoxic gene signature predicts a favorable response to one or more checkpoint inhibitors; wherein the absence of a cytotoxic gene signature predicts an unfavorable response to one or more checkpoint inhibitors; c) optionally, treating the subject with one or more checkpoint inhibitors if a cytotoxic gene signature is identified.

28. A method for identifying a cancer that is susceptible to treatment with a checkpoint inhibitor, the method comprising: a) detecting the expression level of five or more signature genes listed in Table 1 in the tumor sample, wherein detecting comprises one or more of: i) immunohistochemical staining (IHC); ii) single-cell RNA sequencing; and iii) whole transcriptome RNA sequencing; b) comparing the detected expression level to a control level or a predetermined threshold level to identify a cytotoxic gene signature; wherein the presence of a cytotoxic gene signature identifies a cancer that is susceptible to checkpoint inhibitors; wherein the absence of a cytotoxic gene signature identifies a cancer that is not susceptible to checkpoint inhibitors; and c) optionally, treating the subject with one or more checkpoint inhibitors if a cytotoxic gene profile is identified.

29. The method of any one of embodiments 26-28, wherein the signature genes comprise at least the first 5 genes, at least the first 10 genes, at least the first 20 genes, at least the first 25 genes, at least the first 30 genes, at least the first 35 genes, at least the first 40 genes, or at least the first 50 genes of Table 1.

30. The method of any one of embodiments 26-28, wherein the five or more signature genes comprise the first 10 genes or the first 25 genes of Table 1.

31. The method of any one of embodiments 26-28, wherein three of the five or more signature genes comprise granzyme B, granzyme K, and perforin.

32. The method of any one of embodiments 26-28, wherein four of the five or more signature genes comprise granzyme A, granzyme H, granulysin, and perforin 1.

33. The method of any one of embodiments 26-28, wherein the control level or the predetermined threshold value is derived from healthy matched tissue, or matched tissue know to lack a cytotoxic gene signature.

34. The method of embodiment 33, wherein the control level or threshold level is derived from whole transcriptome expression score data from a tissue matched, non-tumor sample, and detection comprises whole transcriptome sequencing.

35. The method of embodiment 34, wherein the subject's whole transcriptome sequencing provides expression score data, and at least the expression score data of the subject's signature genes are compared to the expression score data of the signature genes of the control; wherein if the subject's expression score data are higher than the control expression score data for each of the five or more signature genes, the subject's tumor is identified as having a cytotoxic gene signature.

36. The method of embodiment 34, wherein the control level comprises protein expression values derived from IHC imaging of the at least 5 signature genes; wherein the detection method comprise IHC and provides protein expression value data; wherein if the subject's protein expression value data are greater than the control protein expression value data, the subject's tumor is identified as having a cytotoxic gene signature.

37. The method of any one of embodiments 26-28, wherein the control level or the predetermined threshold value is derived from tumor-infiltrating CD4+ T-cells from a cohort of matched tumor samples.

38. The method of embodiment 37, wherein the control level or threshold level is derived from expression scores derived from single cell sequencing of the tumor-infiltrating CD4+ T-cells of the cohort samples.

39. The method of embodiment 38, wherein the predetermined threshold comprises a geometric mean calculated from the expression scores of the signature genes in the CD4+ T-cells of the cohort samples.

40. The method of embodiment 39, wherein the detection method comprises whole transcriptome sequencing that yields expression score data for at least the signature genes, wherein a geometric mean is calculated from the expression score data of the signature genes and compared to the geometric mean of the threshold geometric mean; wherein if the subject's geometric mean is higher than the threshold geometric mean, the subject's tumor is identified as having a cytotoxic gene signature.

41. The method of embodiment 38, wherein the detection method comprises single cell RNA sequencing that yields expression score data, wherein the subject's tumor expression score data for at least the signature genes is compared to the control expression score data for the signature genes; wherein if the subject's expression score data is equal to or greater than the control expression score data, the subject's tumor is identified as having a cytotoxic gene signature.

42. The method of any one of embodiments 26-41, wherein the subject is diagnosed with or suspected of having an altered human leukocyte antigen (HLA) phenotype in a population of tumor cells due to a mutation in at least one HLA class I gene.

43. The method embodiment 42, wherein the population of the subject's tumor cells have a loss of function mutation in at least one HLA class I gene.

44. The method of embodiment 42, wherein the population of the subject's tumor cells have a loss of heterozygosity in at least one HLA class I gene.

45. The method of embodiment 42, wherein the population of the subject's tumor cells have a complete loss of at least one HLA class I gene.

46. The method of any one of embodiments 26-45, wherein the tumor comprises one or more of a non-small cell lung cancer, bladder cancer, colorectal cancer, and liver cancer.

47. The method of any one of embodiments 26-46, wherein the tumor comprises a non-small cell lung cancer.

48. The method of any one of the preceding embodiments, comprising treating the subject with one or more checkpoint inhibitors.

49. The method of embodiment 48, wherein the one or more checkpoint inhibitors are selected from the group consisting of pembrolizumab, nivolumab, ipilimumab, atezolizumab, cemiplimab, durvalumab, and avelumab.

50. The method of embodiment 48 or 49, comprising treating the patient with at least one additional immunomodulatory molecule and/or at least one additional cancer therapeutic.

51. The method of embodiment 50, wherein the at least one additional immunomodulatory molecule and/or at least one additional cancer therapeutic comprises one or more of a T-cell immunoglobulin and mucin domain-3 antibody (TIM3), radiation, surgery, and chemotherapy.

52. The method of any one of embodiments 26-51, wherein the cancer sample comprises a solid tumor biopsy from a cancer patient.

53. A method for determining an immune-oncology (IO) Progression Risk for a subject diagnosed with cancer, comprising: in a tumor sample from a subject: a) determining a cytotoxic T-cell expression score (CYT) in the tumor sample; b) determining a tumor mutation burden (TMB) score in the tumor sample; wherein if the CYT score is below a CYT threshold level and the TMB score is below a TMB score threshold level, determining that the subject has in increased IO Progression Risk.

54. The method of embodiment 53, wherein the CYT score is determined according to claim 1.

55. The method of embodiment 53, wherein determining the TMB score comprises: a) sequencing the DNA of the tumor sample and identifying the number of non-synonymous somatic mutations in the tumor sample; b) calculating the TMB score by dividing the number non-synonymous somatic mutations of part (a) by the total number of megabases of genomic sequenced.

56. The method of any one of embodiments 53-55, wherein the CYT threshold comprises the use of a real world cohort comprising at least 100 subjects, wherein the cohort subjects have the same cancer as the subject.

57. The method of any one of embodiments 53-56, wherein the TMB threshold comprises the use of a real world cohort comprising at least 100 subjects, wherein the cohort subjects have the same cancer as the subject.

58. The method of any one of the previous embodiments, wherein the subject's cancer is non-small cell lung cancer (NSCLC).

59. The method of embodiment 58, wherein the subject's cancer is a non-squamous histology subtype.

60. The method of embodiment 59, wherein the subject has stage IV cancer.

61. The method of any one of embodiment 58-60, wherein the subject has had no prior immune-oncology therapy.

62. The method of any one of embodiments 53-57, wherein the subject's cancer is comprises head and neck cancer.

63. The method of any one of embodiments 53-57, wherein the subject's cancer is comprises bladder cancer.

64. The method of any one of embodiments 53-63, wherein the subject has an increased IO Progression Risk, the method further comprising one or more of the following: a) providing a schedule for tumor imaging in alignment with tumor progression; b) interpreting increased tumor size or suspect imaging results as tumor progression and not pseudo-progression; c) administering a new therapy regimen, including one or more of immunotherapy, chemotherapy, surgery, and palliative care.

65. The method of any one of embodiments 53-63, wherein the wherein the subject has no increased IO Progression Risk, the method further comprising: treating the subject with one or more checkpoint inhibitors.

66. The method of embodiment 65, wherein the one or more checkpoint inhibitors are selected from the group consisting of pembrolizumab, nivolumab, ipilimumab, atezolizumab, cemiplimab, durvalumab, and avelumab.

67. The method of embodiment 65 or 66, comprising treating the patient with at least one additional immunomodulatory molecule and/or at least one additional cancer therapeutic.

68. The method of embodiment 67, wherein the at least one additional immunomodulatory molecule and/or at least one additional cancer therapeutic comprises one or more of a T-cell immunoglobulin and mucin domain-3 antibody (TIM3), radiation, surgery, and chemotherapy.

69. The method of any of embodiments 53-68, wherein the cancer sample comprises a solid tumor biopsy from a cancer patient.

70. A method for treating a subject that has been diagnosed with cancer, the method comprising: a) detecting the expression level of five or more signature genes listed in Table 1 in the tumor sample, wherein detecting comprises one or more of: i) immunohistochemical staining (IHC); ii) single-cell RNA sequencing; and iii) whole transcriptome RNA sequencing; b) comparing the detected expression level to a control level or a predetermined threshold level to identify a cytotoxic gene signature; c) determining the tumor mutation burden (TMB) in the tumor sample; d) comparing the determined TMB to a predetermined threshold level to determine a TMB score; e) calculating an IO Risk Progression based on (b) and (d); f) treating the subject with one or more checkpoint inhibitors when the calculation in (e) shows no increased IO Progression Risk.

71. A method of predicting a response to a checkpoint inhibitor therapy in a subject diagnosed with cancer, the method comprising: a) detecting the expression level of five or more signature genes listed in Table 1 in the tumor sample, wherein detecting comprises one or more of: i) immunohistochemical staining (IHC); ii) single-cell RNA sequencing; and iii) whole transcriptome RNA sequencing; b) comparing the detected expression level to a control level or a predetermined threshold level to identify a cytotoxic gene signature; c) determining the tumor mutation burden (TMB) in the tumor sample; d) comparing the determined TMB to a predetermined threshold level to determine a TMB score; e) calculating an IO Risk Progression based on (b) and (d); wherein no increased IO Progression Risk predicts a favorable response to checkpoint inhibitors; wherein increased IO Progression Risk predicts an unfavorable response to checkpoint inhibitors; and f) optionally treating the subject with one or more checkpoint inhibitors when the calculation in (e) shows no increased IO Progression Risk.

72. A method for identifying a cancer that is susceptible to treatment with a checkpoint inhibitor, the method comprising: a) detecting the expression level of five or more signature genes listed in Table 1 in the tumor sample, wherein detecting comprises one or more of: i) immunohistochemical staining (IHC); ii) single-cell RNA sequencing; and iii) whole transcriptome RNA sequencing; b) comparing the detected expression level to a control level or a predetermined threshold level to identify a cytotoxic gene signature; c) determining the tumor mutation burden (TMB) in the tumor sample; d) comparing the determined TMB to a predetermined threshold level to determine a TMB score; e) calculating an IO Risk Progression based on (b) and (d); wherein no increased IO Progression Risk identifies a cancer that is susceptible to checkpoint inhibitors; wherein increased IO Progression Risk identifies a cancer that is not susceptible to checkpoint inhibitors; and f) optionally treating the subject with one or more checkpoint inhibitors when the calculation in (e) shows no increased IO Progression Risk.

73. The method of any one of embodiments 70-72, comprising treating the subject with one or more checkpoint inhibitors selected from the group consisting of pembrolizumab, nivolumab, ipilimumab, atezolizumab, cemiplimab, durvalumab, and avelumab.

74. The method of embodiment 73, comprising treating the patient with at least one additional immunomodulatory molecule and/or at least one additional cancer therapeutic.

75. The method of embodiment 74, wherein the at least one additional immunomodulatory molecule and/or at least one additional cancer therapeutic comprises one or more of a T-cell immunoglobulin and mucin domain-3 antibody (TIM3), radiation, surgery, and chemotherapy.

76. The method of any one of embodiments 70-75, wherein the cancer sample comprises a solid tumor biopsy from a cancer patient.

77. The method of any one of embodiments 1-76, wherein the signature genes comprise or consist of CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, and DUSP4.

78. The method of any one of embodiments 1-76, wherein the signature genes comprise or consist of CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, DUSP4, CTSC, CXCR6, ABI3, S100A4, and FGFBP2.

79. The method of any one of embodiments 53-78, wherein determining TMB comprises a targeted panel, the panel comprising one or more genes selected from ABCB1, ABCC3, ABL1, ABL2, FAM175A, ACTA2, ACVR1, ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf34, CALR, CARD11, CARM1, CASP8, CASR, CBFB, CBL, CBLB, CBLC, CBR3, CCDC6, CCND1, CCND2, CCND3, CCNE1, CD19, CD22, CD274, CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYNC2H1, EBF1, ECT2L, EGF, EGFR, EGLN1, EIF1AX, ELF3, TCEB1, C11orf30, ENG, EP300, EPCAM, EPHA2, EPHA7, EPHB1, EPHB2, EPOR, ERBB2, ERBB3, ERBB4, ERCC1, ERCC2, ERCC3, ERCC4, ERCC5, ERCC6, ERG, ERRFI1, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANCI, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOXP1, FOXQ1, FRS2, FUBP1, FUS, G6PD, GABRA6, GALNT12, GATA1, GATA2, GATA3, GATA4, GATA6, GEN1, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HIST1H1E, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDO1, IFIT1, IFIT2, IFIT3, IFNAR1, IFNAR2, IFNGR1, IFNGR2, IFNL3, IKBKE, IKZF1, IL10RA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEF1, LMNA, LMO1, LRP1B, LYN, LZTR1, MAD2L2, MAF, MAFB, MAGI2, MALT1, MAP2K1, MAP2K2, MAP2K4, MAP3K1, MAP3K7, MAPK1, MAX, MC1R, MCL1, MDM2, MDM4, MED12, MEF2B, MEN1, MET, MGMT, MIB1, MITF, MKI67, MLH1, MLH3, MLLT3, MN1, MPL, MRE11A, MS4A1, MSH2, MSH3, MSH6, MTAP, MTHFD2, MTHFR, MTOR, MTRR, MUTYH, MYB, MYC, MYCL, MYCN, MYD88, MYH11, NBN, NCOR1, NCOR2, NF1, NF2, NFE2L2, NFKBIA, NHP2, NKX2-1, NOP10, NOTCH1, NOTCH2, NOTCH3, NOTCH4, NPM1, NQO1, NRAS, NRG1, NSD1, WHSC1, NT5C2, NTHL1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCD1LG2, PDG-FRA, PDGFRB, PDK1, PHF6, PHGDH, PHLPP1, PHLPP2, PHOX2B, PIAS4, PIK3C2B, PIK3CA, PIK3CB, PIK3CD, PIK3CG, PIK3R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2R1A, PPP2R2A, PPP6C, PRCC, PRDM1, PREX2, PRKAR1A, PRKDC, PARK2, PRSS1, PTCH1, PTCH2, PTEN, PTPN11, PTPN13, PTPN22, PTPRD, PTPRT, QKI, RAC1, RAD21, RAD50, RAD51, RAD51B, RAD51C, RAD51D, RAD54L, RAF1, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNX1T1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SMAD2, SMAD3, SMAD4, SMARCA1, SMARCA4, SMARCB1, SMARCE1, SMC1A, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STATE, STK11, SUFU, SUZ12, SYK, SYNE1, TAF1, TANC1, TAP1, TAP2, TARBP2, TBC1D12, TBL1XR1, TBX3, TCF3, TCF7L2, TCL1A, TERT, TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, C10orf54, WEE1, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, and ZRSR2.

80. The method of embodiment 79, wherein the panel comprise each of the listed genes.

81. The method of embodiment 80, wherein the panel consists of each the listed genes.

EXAMPLES

The following Examples are illustrative and are not intended to limit the scope of the claimed subject matter.

Example 1. Determining Cytotoxic CD4 Gene Profile Using Single Cell Sequencing

Ten specimens were evaluated with single cell RNA sequencing (scRNAseq) to identify tumor infiltrating immune cell population, characterize their transcriptional profile (see FIG. 1), and identify the gene signature of CD4+ T-cells. In this example, single cell RNA sequencing (scRNA-seq) for cancer samples (lung tumor samples), was performed using 10× Genomics Single Cell 5' platform, version 2 (P/N 1000020, 10× Genomics). The cancer samples were obtained as previously frozen dissociated tumor cells (DTCs) (Discovery Life Sciences, Huntsville, AL). DTCs were thawed and washed with FACS buffer (PBS, 0.04% BSA). The cells were incubated with FITC-conjugated anti-Human-CD45 antibody (Cat #304006, BioLegend), and DAPI. A cocktail of ~30 CITE-seq antibodies specific to immunology surface markers (BioLegend, San Diego, CA) were used to provide immunological classification information. Human TruStain FcX™ (Fc Receptor Blocking Solution (Cat #422301, BioLegend) was used to block the Fc receptor. Samples were stained with designated antibodies for 30 minutes at 4° C. and washed twice with FACS buffer. Samples may be sorted using SH800S cells sorter (Sony Biotechnology). Live cells were gated on DAPI− cells, sorted as CD45+ and CD45− populations and collected in RPMI. The sorted CD45+ and CD45− cells were pelleted and resuspended to recover a target of 3000 cells after 10× droplet formation. Cellular suspensions were barcoded using a Chromium Single Cell Controller instrument (10× Genomics) and 10× Genomics Chromium Single Cell A Chip Kit (P/N 120236, 10× Genomics) to generate single-cell Gel Beads-in-Emulsion (GEMs) for reverse transcription. Single-cell RNA-Seq libraries were prepared using the Chromium Single Cell 5' Library and Gel Bead Kit (P/N 1000020, 10× Genomics) as per manufacturer's instructions. For each tumor sample, four libraries were generated: CD45− Exom library, CD45+ Exom library, CD45+ TCR library, and CD45+ CITE-seq library.

The following steps were carried out for 5' gene expression library construction: (1) fragmentation, end repair and A-tailing; (2) post fragmentation, end repair and A-tailing double sided size selection with SPRIselect; (3) adaptor ligation; (4) post ligation cleanup with SPRIselect (Cat #B23318, Beckman Coulter); (5) sample index PCR and cleanup. For the enriched library construction (T-Cell Receptor libraries), the following were performed: (1) fragmentation, end repair and A-tailing; (2) adaptor ligation; (3) post ligation cleanup using SPRIselect; (4) sample index PCR and cleanup.

The barcoded sequencing libraries were quantified by Qubit dsDNA HS Assay Kit (Cat #Q32854, Thermo Fisher Scientific, Waltham, MA). The quality of sequencing libraries was checked using Labchip GX Touch Nucleic Acid Analyzer (P/N CLS138162, PerkinElmer, Waltham, MA). 1 flow cell (Ref 20022408, Illumina, Inc., San Diego, CA) with proportion (1 CITE:1 TCR:5 CD45+ EXOM:5 CD45− EXOM) were used for each tumor sample. The libraries were sequenced using the Illumina NextSeq 550 system.

In some embodiments, a plurality of RNA features were identified through the analysis of sequencing files. For example, raw sequencing files were processed through the CellRanger pipeline (version 3.1.0) and then analyzed using scanpy (version 1.6) and scirpy (version 0.4). A filtering step was employed next. For example, the filtering step removed from downstream analysis one or more of the following: cells with detectable gene expression in less than a lower threshold number of genes; cells with detectable gene expression in greater than a threshold percentage of mitochondrial genes; or cells with detectable gene expression in greater than an upper threshold number of genes. In one example, cells with detectable gene expression in less than 200 genes, greater than 25% mitochondrial genes or greater than 2500 genes were removed from downstream analyses, as were any genes expressed in less than 3 cells. Scrublet, which is referenced at Wolock, S. L., Lopez, R. & Klein, A. M. Scrublet: Computational Identification of Cell Doublets in Single-Cell Transcriptomic Data. Cell Systems 8, 281-291.e9 (2019), may be used for doublet detection and removal. Gene expression values were normalized to 10,000 counts per cell and log transformed. Protein expression values were normalized using the centered log-ratio normalization.

The CD4+ T-cell population signature was then identified as follows.

The data was filtered on the CD4+ T cell population, based on protein expression of CD45, CD3, CD4, CD8 and CD20. Batch correction was performed on the gene expression data using BBKNN (10), filtered on highly variable genes, and scaled to unit variance.

Non-negative matrix factorization (NMF) was used to identify subpopulations within the CD4+ T cells. The CD4+ T cell gene expression matrix, M, is factorized into two matrices, W and H so that M≈WH. Each column of W can be interpreted as different transcriptional programs and H contains the weights of each transcriptional program that make up the total gene expression for each cell. {M is genes by cells; set some number K=5 to create 5 sub-types; break into two matrices.} First matrix, W, includes those topics by cell so you can determine how each topic contributes to the total transcriptional makeup of the cell. The second matrix, H, is genes by sub-types and that shows how each gene is weighted by topic. In some embodiments, the number of cells is more than 1,000, more than 10,000, more than 100,000, etc. The number of genes in M is a subset of all transcriptomic genes as described above. The listing of genes may vary depending on the nature of the cells being sequenced, the total composition of the sample (e.g. purified t-cells vs. t-cells and tumor), sequencing depth; etc. The genes that contribute the most to a topic can be ranked, and cut-off rank at a pre-determined threshold can also be established. In one example, the threshold is 25 genes. In other examples, the threshold can be between 2 genes and 100 genes.

Table 1 below shows the relative weight of 100 different genes in cytotoxic CD4+ T cells. As described above, a gene profile (IO Response Profile) may be defined by a subset of the genes in Table 1, e.g., a cut-off may be established with the first 2 gene, the first 5 genes, the first 10 genes, the first 20 genes, the first 25 genes, the first 30 genes, or the first 50 genes in such a weighted listing. In some embodiments, the cutoff is the first 25 genes. In some embodiments, the genes selected for evaluation to identify a cytotoxic CD4+ gene signature may include PRF1, GZMA, GZHM, and GNLY. In some embodiments, the genes selected for evaluation to identify a cytotxic CD4+ gene signature include CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, and DUSP4. In some embodiments, the genes selected for evaluation to identify a cytotoxic CD4+ gene signature include CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, DUSP4, CTSC, CXCR6, ABI3, S100A4, and FGFBP2.

TABLE 1

| Gene | Weight |
|------|--------|
| CCL5 | 0.11553707 |
| GZMA | 0.11119375 |
| NKG7 | 0.10792594 |
| CCL4 | 0.10607658 |
| GZMH | 0.09819277 |
| CST7 | 0.09637749 |
| GZMB | 0.09052262 |
| GZMK | 0.08087941 |
| GNLY | 0.07304029 |

TABLE 1-continued

| Gene | Weight |
| --- | --- |
| PRF1 | 0.0697381 |
| CCL4L2 | 0.06746927 |
| CD52 | 0.0671189 |
| IL32 | 0.06348354 |
| CD74 | 0.06177709 |
| CTSW | 0.06042883 |
| CRIP1 | 0.05988814 |
| CCL3 | 0.05630675 |
| ITM2C | 0.05581316 |
| IFNG | 0.05233069 |
| S100A10 | 0.05015405 |
| TUBA4A | 0.04922318 |
| FGFBP2 | 0.04810496 |
| LAG3 | 0.04724802 |
| S100A4 | 0.04609252 |
| EOMES | 0.04545036 |
| HOPX | 0.04443346 |
| DUSP4 | 0.04436067 |
| PLEK | 0.04343599 |
| S100A11 | 0.04326302 |
| ABI3 | 0.04315321 |
| KLRD1 | 0.04282515 |
| LGALS1 | 0.04281545 |
| CTSC | 0.04278671 |
| CRTAM | 0.04165706 |
| ZNF683 | 0.04127708 |
| DUSP2 | 0.03970615 |
| SRRT | 0.03917101 |
| CLEC2B | 0.03907536 |
| LDHA | 0.038759 |
| ENC1 | 0.03859638 |
| OASL | 0.03731479 |
| ZEB2 | 0.03720007 |
| HSPE1 | 0.03704164 |
| CXCR6 | 0.03624443 |
| GIMAP4 | 0.03505498 |
| PTMS | 0.03441307 |
| DNAJA1 | 0.03425662 |
| GIMAP7 | 0.03418167 |
| PDCD1 | 0.03324803 |
| TNFSF9 | 0.03300823 |
| ISG20 | 0.03253554 |
| CCL3L1 | 0.03244689 |
| PKM | 0.03164835 |
| CXCR3 | 0.03160576 |
| SLA | 0.03077559 |
| XCL2 | 0.03022319 |
| TBX21 | 0.02981124 |
| FASLG | 0.02965684 |
| RNF213 | 0.02941825 |
| SLAMF7 | 0.02896132 |
| CD70 | 0.02891628 |
| FABP5 | 0.02871164 |
| FCRL6 | 0.02843698 |
| ITM2A | 0.02792281 |
| SYTL3 | 0.02776929 |
| S1PR5 | 0.02763959 |
| RGS1 | 0.02762577 |
| TXNIP | 0.02746667 |
| LGALS3 | 0.02741297 |
| KLRG1 | 0.02715867 |
| TYROBP | 0.02707809 |
| RPS27L | 0.02704993 |
| H2AFZ | 0.02703339 |
| TRAT1 | 0.02688795 |
| ITGA1 | 0.0268685 |
| XCL1 | 0.02667611 |
| RGCC | 0.02655055 |
| CACYBP | 0.02653767 |
| LYST | 0.02621355 |
| GGA2 | 0.02590172 |
| ID2 | 0.02578471 |
| SAMSN1 | 0.02578401 |
| PTPN7 | 0.02543192 |
| MT2A | 0.02527319 |
| TGFB1 | 0.02501246 |
| HAVCR2 | 0.02491684 |
| ISG15 | 0.02412499 |

TABLE 1-continued

| Gene | Weight |
| --- | --- |
| GBPS | 0.02334112 |
| KRT86 | 0.02326803 |
| MAP3K8 | 0.02320523 |
| SYNE1 | 0.02314846 |
| SLC7A5 | 0.02304304 |
| ARHGAP30 | 0.02301441 |
| HSPH1 | 0.02300987 |
| CORO1B | 0.02258396 |
| KIAA1551 | 0.02231347 |
| PARP8 | 0.022299 |
| THEMIS | 0.02223858 |
| MYO1F | 0.02199791 |
| FKBP4 | 0.02191047 |

Example 2. Determining Cytotoxic CD4 Gene
Profile Using Immunohistochemical (IHC) Staining Specimen types: IHC staining for cytotoxic CD4+ T cells can be performed on fresh-frozen or formalin fixed paraffin embedded (FFPE) preserved slides of tumor biopsies or resections. This method can be applied to any solid tumor of any stage.

Protocol: IHC staining protocol are known in the art (see, e.g., Crosby et al., Immunohistochemistry Protocol for Paraffin-embedded Tissue Sections, Jove (2014), doi: 10.3791/5064). Briefly, antibodies that recognize a target antigen of interest are applied to a prepared sample. The antibody-antigen interaction is then visualized using either chromogenic or fluorescent detection. Suitable antibodies for the identification of cytotoxic CD4+ T cells include, for example, antibodies against CD4, Granzyme B, Granzyme K, pan-HLA II and pan-cytokeratin. In some embodiments, a multiplex IHC method may be employed, allowing for simultaneous detection of multiple markers on a single tissue section. Multiplex IHC techniques are known in the art (see, e.g., Tan et al., Overview of multiplex immunohistochemistry/immunofluorescence techniques in the era of cancer immunotherapy, Cancer Commun (Lond). (2020) 40(4): 135-153).

Identification of cytotoxic CD4 T cells and HLA-II expression tumor cells: Cytotoxic CD4 T cells are identified by the co-localization of the CD4 and Granzyme B stains and HLA-II expressing tumor cells are identified by the co-localization of the pan-HLA-II and pan-cytokeratin stains. Cell identification can be performed through either expert pathologist review or computer based IHC scoring.

Example 3. Determining Cytotoxic CD4 Gene
Profile Using Whole-Transcriptome RNA
Sequencing Whole-transcriptome RNA sequencing data may be deconvoluted to reveal a cytotoxic CD4 gene profile data. For example, a plurality of specimens may be sequenced using both whole-transcriptome RNA sequencing and single-cell RNA sequencing in order to develop the relevant gene profile; such a gene profile may then be used in the deconvolution. Cytotoxic CD4+ T cells can be identified using a cytotoxic CD4 gene signature, such as a cytotoxic CD4 gene signature described above in Example 1 (e.g., the first 25 genes listed in Table 1). Additionally or alternatively, a signature can be calculated by taking the geometric mean of the gene list (or selected genes from the list, such as the top 5, 10, 25, etc.) or by performing single sample gene set enrichment. In other examples, a cohort of RNA whole-transcriptome data, on a pan-cancer basis or a sub-type basis, may be used to determine threshold values (e.g., to determine whether cytotoxic CD4+ T cells are present or not).

For example, a patient's tumor specimen could be sequenced using whole transcriptome sequencing. The patient's tumor would be scored using the cytotoxic CD4+ gene signature described Example 1. A patient's tumor would be reported as having a high cytotoxic status if their cytotoxic score is above a threshold set based on a training set of RNAseq data from IO treated patients. Table 3 shows the cytotoxic scores for such patients.

Example 4. Model Training

For the training set, the geometric mean of the expression level of the top 25 genes of Table 1 were evaluated in a cohort of 149 IO treated subjects to derive the CS score, i.e., the "score" in table 3. The threshold value was calculated by identifying a set of genes associated with cytotoxic CD4 and CD8 T cells in single cell RNAseq data. Then the association of each gene with time to progression in the NSCLC IO training cohort is evaluated using a Cox proportional hazards model. Genes with a hazard ratio less than 1 are selected for the final CYT gene signature. The CYT gene signature is calculated as the arithmetic mean of the log-transformed, normalized RNA counts for the selected genes. Then a multivariate Cox proportional hazards model is trained using the NSCLC training cohort with the CYT gene signature and tumor mutational burden (TMB) status as features to predict time to progression. The threshold is set to binarize the model scores into high risk and low risk by identifying the model score that maximized the separation of the Kaplan-Meier curves for the two risk categories.

Figure 17B:
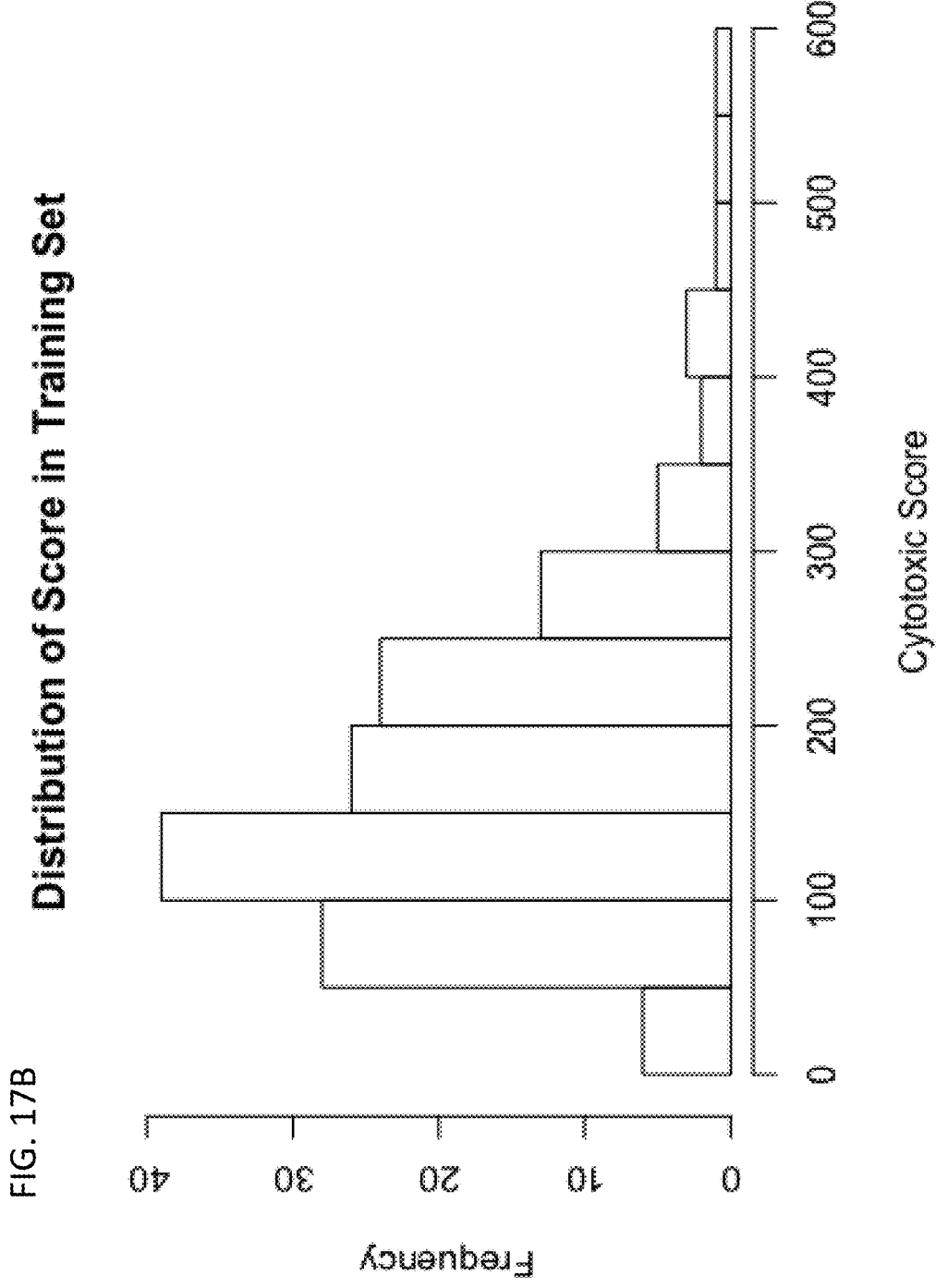

An example of calculating a cytotoxic score (CS) and comparing the score to a threshold value is shown in FIG. 17A, followed by a table showing the distribution of scores in the training set in FIG. 17B. This distribution of scores was used to derive an exemplary threshold value.

TABLE 3

Exemplary patient cytotoxic scores: training set

| Patient | Score |
|---------|-------|
| PT_1 | 141.91924 |
| PT_2 | 94.6707777 |
| PT_3 | 54.1477682 |
| PT_4 | 144.248283 |
| PT_5 | 138.166115 |
| PT_6 | 291.311476 |
| PT_7 | 145.678524 |
| PT_8 | 48.7694824 |
| PT_9 | 134.379726 |
| PT_10 | 184.296065 |
| PT_11 | 299.305716 |
| PT_12 | 234.803816 |
| PT_13 | 146.315236 |
| PT_14 | 190.849713 |
| PT_15 | 437.639552 |
| PT_16 | 77.5932285 |
| PT_17 | 198.412965 |
| PT_18 | 210.637815 |
| PT_19 | 70.4133944 |
| PT_20 | 112.588945 |
| PT_21 | 72.9006656 |
| PT_22 | 134.537763 |

TABLE 3-continued

Exemplary patient cytotoxic scores: training set

| Patient | Score |
|---------|-------|
| PT_23 | 222.469761 |
| PT_24 | 244.240183 |
| PT_25 | 215.157773 |
| PT_26 | 76.6309279 |
| PT_27 | 283.541605 |
| PT_28 | 79.3303358 |
| PT_29 | 224.698123 |
| PT_30 | 283.998596 |
| PT_31 | 194.069392 |
| PT_32 | 364.707646 |
| PT_33 | 237.987557 |
| PT_34 | 126.255546 |
| PT_35 | 109.456633 |
| PT_36 | 164.466464 |
| PT_37 | 125.828466 |
| PT_38 | 131.406361 |
| PT_39 | 262.634297 |
| PT_40 | 165.348216 |
| PT_41 | 94.6795676 |
| PT_42 | 83.1377969 |
| PT_43 | 179.360413 |
| PT_44 | 82.6772874 |
| PT_45 | 61.8897222 |
| PT_46 | 176.684785 |
| PT_47 | 392.228913 |
| PT_48 | 215.352897 |
| PT_49 | 118.322274 |
| PT_50 | 261.737136 |
| PT_51 | 82.6032579 |
| PT_52 | 72.5922113 |
| PT_53 | 114.611231 |
| PT_54 | 141.014839 |
| PT_55 | 186.321409 |
| PT_56 | 255.405118 |
| PT_57 | 253.277139 |
| PT_58 | 189.301501 |
| PT_59 | 210.449045 |
| PT_60 | 238.350065 |
| PT_61 | 512.21066 |
| PT_62 | 76.4730105 |
| PT_63 | 211.649554 |
| PT_64 | 160.732088 |
| PT_65 | 91.7711144 |
| PT_66 | 67.7901627 |
| PT_67 | 120.944681 |
| PT_68 | 135.319597 |
| PT_69 | 340.061303 |
| PT_70 | 95.2016012 |
| PT_71 | 28.5781473 |
| PT_72 | 147.524961 |
| PT_73 | 411.805822 |
| PT_74 | 114.189703 |
| PT_75 | 272.34779 |
| PT_76 | 191.69898 |
| PT_77 | 419.70769 |
| PT_78 | 251.371965 |
| PT_79 | 68.1757953 |
| PT_80 | 122.478714 |
| PT_81 | 141.540281 |
| PT_82 | 122.49218 |
| PT_83 | 267.609751 |
| PT_84 | 97.3849447 |
| PT_85 | 230.386965 |
| PT_86 | 247.370717 |
| PT_87 | 105.82382 |
| PT_88 | 154.777573 |
| PT_89 | 196.338718 |
| PT_90 | 132.474135 |
| PT_91 | 115.374156 |
| PT_92 | 191.885266 |
| PT_93 | 177.294035 |
| PT_94 | 122.696253 |
| PT_95 | 141.429956 |
| PT_96 | 231.725657 |
| PT_97 | 108.380531 |
| PT_98 | 189.885293 |

TABLE 3-continued

| Exemplary patient cytotoxic scores: training set | |
| --- | --- |
| Patient | Score |
| PT_99 | 573.775132 |
| PT_100 | 165.355789 |
| PT_101 | 82.1092551 |
| PT_102 | 70.527204 |
| PT_103 | 135.070284 |
| PT_104 | 82.3445222 |
| PT_105 | 132.668484 |
| PT_106 | 74.2279894 |
| PT_107 | 147.549709 |
| PT_108 | 37.2708382 |
| PT_109 | 123.407538 |
| PT_110 | 107.818117 |
| PT_111 | 19.5990801 |
| PT_112 | 215.455257 |
| PT_113 | 83.068781 |
| PT_114 | 213.452001 |
| PT_115 | 343.01147 |
| PT_116 | 200.161884 |
| PT_117 | 159.015793 |
| PT_118 | 465.688463 |
| PT_119 | 199.836634 |
| PT_120 | 17.5574514 |
| PT_121 | 156.056212 |
| PT_122 | 49.605319 |
| PT_123 | 232.979692 |
| PT_124 | 50.7167914 |
| PT_125 | 117.888933 |
| PT_126 | 179.532144 |
| PT_127 | 320.641687 |
| PT_128 | 214.024939 |
| PT_129 | 213.893871 |
| PT_130 | 159.514734 |
| PT_131 | 179.266125 |
| PT_132 | 269.165866 |
| PT_133 | 300.662547 |
| PT_134 | 74.3044976 |
| PT_135 | 185.136549 |
| PT_136 | 272.921005 |
| PT_137 | 228.355076 |
| PT_138 | 110.954531 |
| PT_139 | 122.831355 |
| PT_140 | 103.676856 |
| PT_141 | 105.270868 |
| PT_142 | 132.729697 |
| PT_143 | 80.3549247 |
| PT_144 | 80.8077136 |
| PT_145 | 156.799862 |
| PT_146 | 220.780079 |
| PT_147 | 205.321806 |
| PT_148 | 345.280279 |
| PT_149 | 218.955629 |

Example 5. CD4+ T-Cell Cytotoxic Signature Predicts Therapy Response

Figure 3:
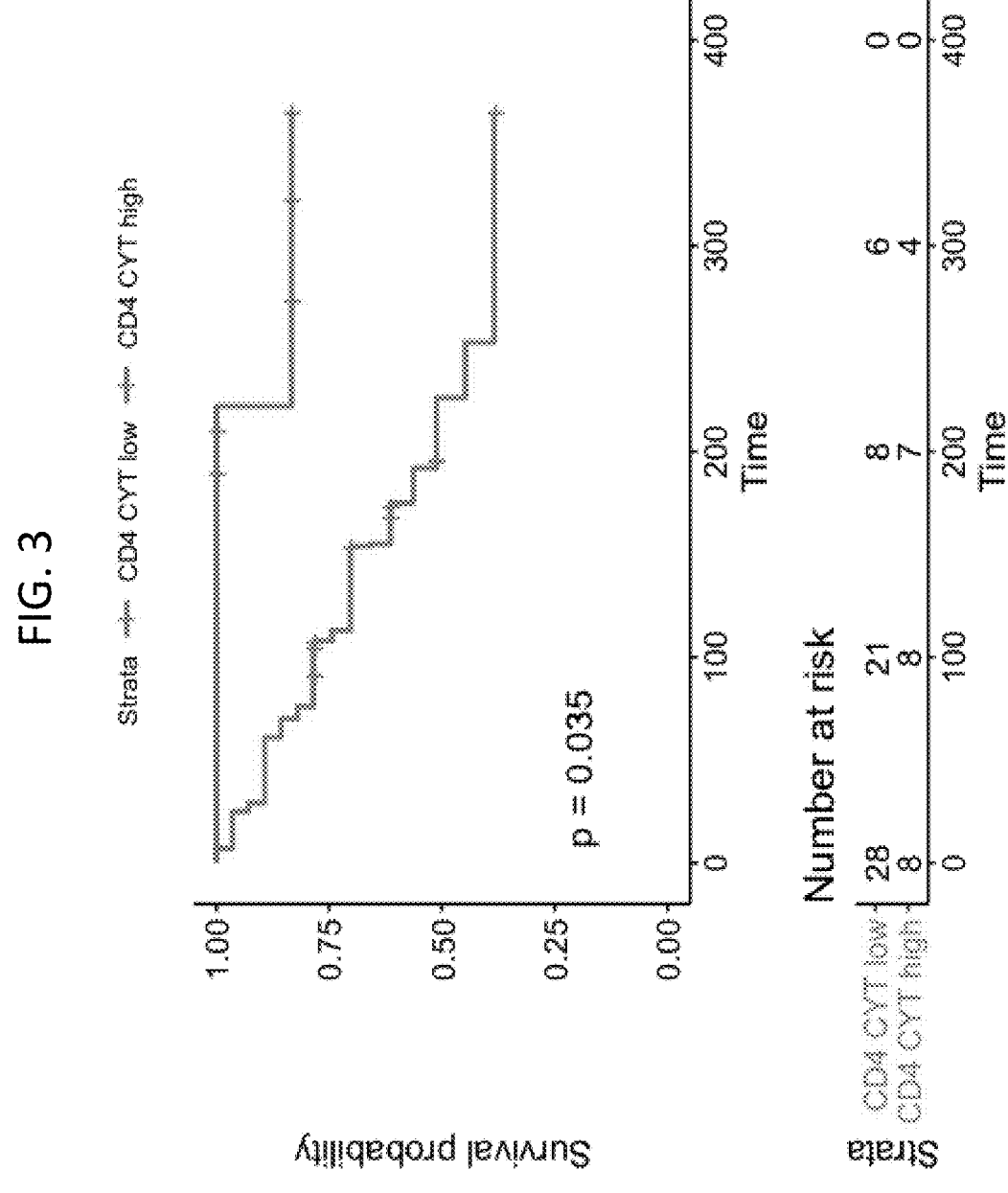
FIG. 3. A CD4+ T cell cytotoxic gene signature is associated with progression free survival in a cohort of NSCLC patients (n=36) with loss of heterozygosity in HLA class I genes (HLA-LOH) treated with checkpoint inhibitor regimens. All patients had metastatic NSCLC. Patients were treated with a Food and Drug Administration (FDA) approved checkpoint inhibitor regimen and underwent Tempus genomic profiling as part of their clinical care. Patients were ranked based on their tumor's expression of the CD4+ T cell cytotoxic gene signature, as described in Example 1. Survival probability over time was higher for patients who had higher expression of the genes defining the CD4+ T cell cytotoxic gene signature (log rank test, p=0.035).

In this example, a set of 36 clinomic records from patients with HLA-LOH were analyzed for response to immunotherapy. All patients had metastatic non-small cell lung cancer (NSCLC), were treated with an FDA approved checkpoint inhibitor regimen and received comprehensive genomic profiling using a DNA sequencing panel of more than 300 genes and whole-transcriptome RNA sequencing. HLA-LOH status was determined by comparing changes in coverage between alleles, in the context of the expected tumor purity between the tumor and matched normal samples; for further details, see U.S. patent application Ser. No. 16/789,413, filed Feb. 12, 2020 (U.S. Pat. No. 11,081, 210) and incorporated herein by reference in its entirety. When LOH occurs in the class I HLA locus in the tumor, CD8+ T cells are no longer able to recognize and kill tumor cells. Studies have shown that this is a common mechanism of immune escape and is associated with worse outcomes for patients treated with immunotherapy (4,5). Surprisingly, however, some patients with HLA-LOH did respond to immunotherapy as measured by progression free survival. As shown in FIG. 3, progression free survival was improved for patients who had higher expression of the cytotoxic profile. Specifically, with respect to FIG. 3, a gene signature for cytotoxic T cells was associated with progression free survival in a cohort of NSCLC patients with HLA LOH treated with checkpoint inhibitor regimens (n=36). For this cohort, the inventors first identified 25 genes associated with cytotoxic CD4 and CD8 T cells in single cell RNA-seq data. The inventors then evaluated the association of each gene with time to progression in the NSCLC IO training cohort using a Cox proportional hazards model. Genes with a hazard ratio less than 1, e.g., NKG7, CCL5, GZMA, CCL4, CST7, GZMH', 'GZMB', 'GZMK', 'PRF1', 'GNLY', 'CCL4L2', 'CD74', 'IL32', 'CD52', 'CCL3', 'LAG3', 'CTSW', 'CTSC', 'CXCR6', 'ABI3', 'S100A4', were selected for the final CYT gene signature. The CYT gene signature was calculated as the arithmetic mean of the log-transformed, normalized RNA counts for the selected genes. We then trained a multivariate Cox proportional hazards model using the NSCLC training cohort with the CYT gene signature and TMB status as features to predict time to progression. We set a threshold to binarize the model scores into high risk and low risk by identifying the model score that maximized the separation of the Kaplan-Meier curves for the two risk categories. All patients had metastatic NSCLC and were treated with an FDA approved checkpoint inhibitor regimen and received comprehensive genomic profiling as part of their clinical care. Patients were ranked based on their tumor's expression of the cytotoxic gene signature described in Example 1. Progression free survival was improved for patients who had higher expression of the cytotoxic profile (log rank test, p=0.035).

Example 6. Cytotoxic CD4+ T Cells Contribute to Anti-Tumor Immune Responses in NSCLC In this example, the inventors build on the work described in Examples 1-4 to characterize a population of CD4+ T cells with a cytotoxic phenotype that is associated with effective anti-tumor immune responses. In this analysis, the inventors used T cell receptor (TCR) profiling in additional to single cell RNA sequencing (scRNAseq) to determine IO Progression Risk.

A. Methods

1. Single Cell Profiling—Control

Single Cell Profiling. Single cell profiling using the 10× Genomics Chromium platform (described in Example 1) was performed on 10 NSCLC dissociated tumor samples. The samples were split into CD45+ and CD45− fractions as described in Example 1 and single cell RNA sequencing was performed on both fractions. Additionally, single cell TCR and cell surface protein profiling (to confirm the presence of the protein receptors identified by RNA analysis) were performed on the CD45+ fraction.

For a description of TCR profiling methods, see U.S. Provisional Patent No. 63/084,459, which is hereby incorporated by reference in its entirety. Raw sequencing files were processed through the 10× CellRanger pipeline and then analyzed using scanpy 1 and scirpy2. Scrublet[3] was used for doublet detection and BBkNN[4] was used for batch correction. HLA typing and quantification was performed using ArcasHLA[5] and scHLAcount[6].

Cell surface protein profiling was performed as described in Stoeckius et al, Simultaneous epitope and transcriptome measurement in single cells. Nat. Methods 14, 865-868 (2017), herein incorporated by reference in its entirety. Briefly, the cells were incubated with a cocktail of 30 TotalSeq antibodies specific to immunology surface markers (BioLegend, San Diego, CA) for 30 minutes at 4° C. and washed twice with FACS buffer as described in Stoeckius et al., 2. Real World Cohort Analysis Real World NSCLC Cohort Analysis. We used a proprietary database to identify 148 de-identified records of patients with metastatic, non-squamous non-small cell lung cancer (NSCLC) who were treated with an FDA approved checkpoint inhibitor (CPI) regimen. Samples were profiled using targeted oncology panel sequencing or whole exome DNA sequencing, and whole transcriptome RNA sequencing on CPI naïve tumor samples. The response to therapy was evaluated using time to progression (TTP), defined as the time from CPI start to the first progression event, censored on the last known physician encounter.

NSCLC Cohort Selection. The NSCLC cohort was selected by filtering the proprietary database of patient records for patients that met the following criteria (for example, inclusion and/or exclusion criteria). The selected patients were (1) assigned NSCLC as their primary diagnosis, (2) had non-squamous histology, (3) were treated with an FDA approved IO regimen as a first line of therapy (in other examples, the IO regimen could be any line of therapy), (4) were metastatic at IO treatment start, and (5) had completed DNA and RNA sequencing results for an IO and checkpoint inhibitor naive sample. Patients that did not have a documented progression event were required to have at least 90 days of follow up (for example, clinical information and/or therapy response data dated at least 90 days after the start of IO therapy). Fine needle aspirate samples were excluded from the analysis. In various embodiments, cohort selection may include multiple iterations of enriched abstraction followed by expert adjudication and clinical data quality control (for example, cleaning and processing). In various embodiments, other inclusion and/or exclusion criteria may be selected for defining the patient cohort.

Clinical Endpoint. The selected clinical endpoint for this study was time to progression (TTP), which is defined as the time from start of the IO or checkpoint inhibitor regime to the first progression event, censored on the patient's last known physician encounter, death, or a treatment stop for a reason other than progression.

3. Tumor Immune Profiling

In this example, a comprehensive, multimodal tumor-immune profile was determined that can assess both tumors' susceptibility to immune recognition and the presence of immune cells with the ability to kill tumor cells. The profiling includes an analysis of the tumor-infiltrating cytotoxic CD4+ T-cells RNA and DNA. RNA analysis is used to determine a cytotoxic T-cell score (see e.g., Examples 1-4, and section (b), below). DNA analysis is used to determine Tumor mutation burden (TMB) as describe below in section (a).

a. TMB Calculation

First, a targeted panel DNA Next Generation Sequencing (NGS) assay, was used. Exemplary panels are described in U.S. patent application Ser. No. 16/789,288 titled Targeted-Panel Tumor Mutational Burden Calculation Systems And Methods and filed Feb. 12, 2020, incorporated herein by reference in its entirety. In some embodiments, the panel comprises one or more genes selected from the group consisting of ABCB1, ABCC3, ABL1, ABL2, FAM175A, ACTA2, ACVR1, ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf34, CALR, CARD11, CARM1, CASP8, CASR, CBFB, CBL, CBLB, CBLC, CBR3, CCDC6, CCND1, CCND2, CCND3, CCNE1, CD19, CD22, CD274, CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYNC2H1, EBF1, ECT2L, EGF, EGFR, EGLN1, EIF1AX, ELF3, TCEB1, C11orf30, ENG, EP300, EPCAM, EPHA2, EPHA7, EPHB1, EPHB2, EPOR, ERBB2, ERBB3, ERBB4, ERCC1, ERCC2, ERCC3, ERCC4, ERCC5, ERCC6, ERG, ERRFI1, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANCI, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOXP1, FOXQ1, FRS2, FUBP1, FUS, G6PD, GABRA6, GALNT12, GATA1, GATA2, GATA3, GATA4, GATA6, GEN1, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HIST1H1E, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDO1, IFIT1, IFIT2, IFIT3, IFNAR1, IFNAR2, IFNGR1, IFNGR2, IFNL3, IKBKE, IKZF1, IL10RA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEF1, LMNA, LMO1, LRP1B, LYN, LZTR1, MAD2L2, MAF, MAFB, MAGI2, MALT1, MAP2K1, MAP2K2, MAP2K4, MAP3K1, MAP3K7, MAPK1, MAX, MC1R, MCL1, MDM2, MDM4, MED12, MEF2B, MEN1, MET, MGMT, MIB1, MITF, MKI67, MLH1, MLH3, MLLT3, MN1, MPL, MRE11A, MS4A1, MSH2, MSH3, MSH6, MTAP, MTHFD2, MTHFR, MTOR, MTRR, MUTYH, MYB, MYC, MYCL, MYCN, MYD88, MYH11, NBN, NCOR1, NCOR2, NF1, NF2, NFE2L2, NFKBIA, NHP2, NKX2-1, NOP10, NOTCH1, NOTCH2, NOTCH3, NOTCH4, NPM1, NQO1, NRAS, NRG1, NSD1, WHSC1, NT5C2, NTHL1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCD1LG2, PDGFRA, PDGFRB, PDK1, PHF6, PHGDH, PHLPP1, PHLPP2, PHOX2B, PIAS4, PIK3C2B, PIK3CA, PIK3CB, PIK3CD, PIK3CG, PIK3R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2R1A, PPP2R2A, PPP6C, PRCC, PRDM1, PREX2, PRKAR1A, PRKDC, PARK2, PRSS1, PTCH1, PTCH2, PTEN, PTPN11, PTPN13, PTPN22, PTPRD, PTPRT, QKI, RAC1, RAD21, RAD50, RAD51, RAD51B, RAD51C, RAD51D, RAD54L, RAF1, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNX1T1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SMAD2, SMAD3, SMAD4, SMARCA1, SMARCA4, SMARCB1, SMARCE1, SMC1A, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STATE, STK11, SUFU, SUZ12, SYK, SYNE1, TAF1, TANC1, TAP1, TAP2, TARBP2, TBC1D12, TBL1XR1, TBX3, TCF3, TCF7L2, TCL1A, TERT, TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, C10orf54, WEE1, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, and ZRSR2. In some embodiments, the panel comprises each of the above-listed genes. In some embodiments, the panel consists of each of the above-listed genes.

The assay includes reagents, software, instruments, and procedures for testing DNA extracted from formalin-fixed, paraffin-embedded (FFPE) tumor specimens and matched normal saliva or blood specimens. The assay is designed to detect and identify somatic alterations for use and interpretation by qualified healthcare professionals to aid in the clinical management of previously diagnosed cancer patients with solid malignant neoplasms.

The DNA sequencing assay is used to analyze a patient specimen to generate genetic data and calculate TMB for that specimen from the genetic data. For an example of TMB calculation and assay methods, see U.S. patent application Ser. No. 16/789,288. Briefly, in some embodiments, a TMB score determined as follows: (1) using NGS methods, sequencing the patient's germline specimen (such as a saliva or blood specimen) to identify sequences of nucleotides in the germline specimen using the targeted-panel to generate germline sequencing results; (2) sequencing the patient's somatic specimen (such as a tumor sample) to identify sequences of nucleotides in the somatic specimen using the targeted-panel to generate somatic sequencing results; (3) quality control (QC) testing on the germ line sequencing results to generate a germline QC score and on the somatic sequencing results to generate a somatic QC score; (4) optionally, generating at least one clinical report, wherein the clinical report comprises a tumor mutational burden (TMB) score associated with the patient, wherein the TMB score is based at least in part on the identified sequences of nucleotides in the germline specimen and identified sequences of nucleotides in the somatic specimen, and wherein the TMB score is calculated from: (i) mutations in the germ line sequencing results and a panel size of the targeted panel when the germline QC score is above a passing threshold and the somatic QC score is below a passing threshold; (ii) mutations in the somatic sequencing results and the panel size of the targeted-panel when the somatic QC score is above the passing threshold and the germline QC score is below the passing threshold; and (iii) mutations in the somatic sequencing results, mutations in the germline sequencing results, and the panel size of the targeted-panel when the somatic QC score is above the passing threshold and the germline QC score is above the passing threshold.

TMB is calculated as the number of non-synonymous somatic mutations divided by the amount of DNA sequenced, using the variant annotation output from a tumor-normal matched targeted sequencing panel for oncology patient specimens and the bioinformatics variant calling pipeline corresponding to the sequencing panel, and Equation 1. Somatic variants are defined as non-synonymous if the variant results in change to the amino acid sequence of the protein.

Equation 1

$$TMB = \frac{(\text{number of non-synonymous somatic mutations})}{(\text{megabases of DNA sequenced})}$$

In this example, the TMB calculation was performed as above and did not include synonymous mutations. In other embodiments, the TMB calculation does include synonymous mutations.

b. Cytotoxic Score (CYT Score) Calculation

Cytotoxic T-cell scores can be calculated according the methods disclosed herein, for example, as described in Examples 1-4. In some embodiments, an RNA-seq assay is used.

The RNA-seq assay is a laboratory developed test (LDT) RNA sequencing assay using next-generation sequencing (NGS) technology that quantifies the expression of over 20,000 genes in tumor tissue from previously diagnosed cancer patients that can be used to develop gene expression profiles. The assay provides information regarding gene expression profiles for use by qualified health care professionals in accordance with professional guidelines in oncology for patients with solid or hematologic neoplasms.

The operation of the RNA-seq assay includes several components and processes. Briefly, FFPE tumor specimens with a minimum tumor content of 20% from solid tumors or 1 mL of fresh peripheral blood or bone marrow aspirate for hematologic malignancies are prepared following standard pathology practices. Total nucleic acid (TNA) is extracted from tissue, treated with DNase to degrade DNA, and remaining RNA is assessed for quality. Library preparation is performed using the KAPA RNA HyperPrep Kit for Illumina with IDT unique dual indexed (UDI) unique molecular identifier (UMI) adapters. Following library preparation and amplification, targets are captured by hybridization, clean-up of captured targets is performed, and unbound fragments are washed away. The amplified target-captured libraries are sequenced to an average of 50 million reads on an Illumina NovaSeq 6000 System using patterned flow cell technology. To pass quality control, each tumor sample must have at least 30 million sequenced reads (15 million read pairs), PCR duplication rate less than or equal to 80%, average GC content between 45% and 59%, and >12,000 expressed genes detected, as assessed during data analysis.

RNA reads are mapped to the Grch37 (hg19) Ensembl reference using pseudo-alignment as implemented in the kallisto2 tool (Nicolas L Bray, Harold Pimentel, Páll Melsted and Lior Pachter, Near-optimal probabilistic RNA-seq quantification, Nature Biotechnology 34, 525-527 (2016), doi: 10.1038/nbt.3519). In its raw form, this mapping results in 180,253 mapped transcripts. All transcripts associated with a specific gene are aggregated in order to compute gene-level transcript counts. In some embodiments, the RNA sequencing data generated by this assay can be used to determine CYT score, or TMB. That is, TMB may be calculated using RNA data, DNA data, or both. In some embodiments, the CYT score is derived from RNA data and the TMB is derived from DNA data.

The cytotoxic score or CYT score, takes the mean gene-level transcript counts of a set of genes from Table 1 (e.g., CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, and DUSP4, or CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, DUSP4, CTSC, CXCR6, ABI3, S100A4, and FGFBP2), which may be expressed by infiltrating immune cells in the TIME. Expression of these genes was quantified by a whole transcriptome RNA-seq assay. The CYT score characterizes the presence and activity of cells that function in immune cell mediated killing of tumor cells.

Increased TMB in tumor cells broadly correlates with increased levels of neoantigens expressed by tumor cells. These neoantigens are more likely to be recognized as non-self by the patient's immune system. CYT measures the cytotoxic activity of tumor infiltrating immune cells, which helps to characterize underlying sensitivity and/or responsiveness to IO in the TIME.

c. IO Progression Risk Determination

Following TMB and CYT calculation, thresholds, derived as described above, are used to determine if a tumor has a TMB greater than the TMB threshold, or CYT score is greater than the CYT threshold, or both. Those results are then used to assign progression risk, using the ruleset outlined in Table 2. If the TMB score is below the TMB threshold, and the CYT score is below the CYT threshold, the IO Progression Risk test will determine "increased progression risk." In all other cases, "no increased progression risk detected" will be determined (Table 2, below). The optimized threshold for TMB and CYT were identified using a proprietary method in a RWE study cohort of metastatic NSCLC patients.

TABLE 2

Feature combination and risk assignment for the Tempus IO Progression Risk Test

| | TMB ≥ threshold | TMB < threshold |
|---|---|---|
| CYT > threshold | no increased progression risk detected | no increased progression risk detected |
| CYT < threshold | no increased progression risk detected | increased progression risk |

B. Results

Figures 4A, 4B:
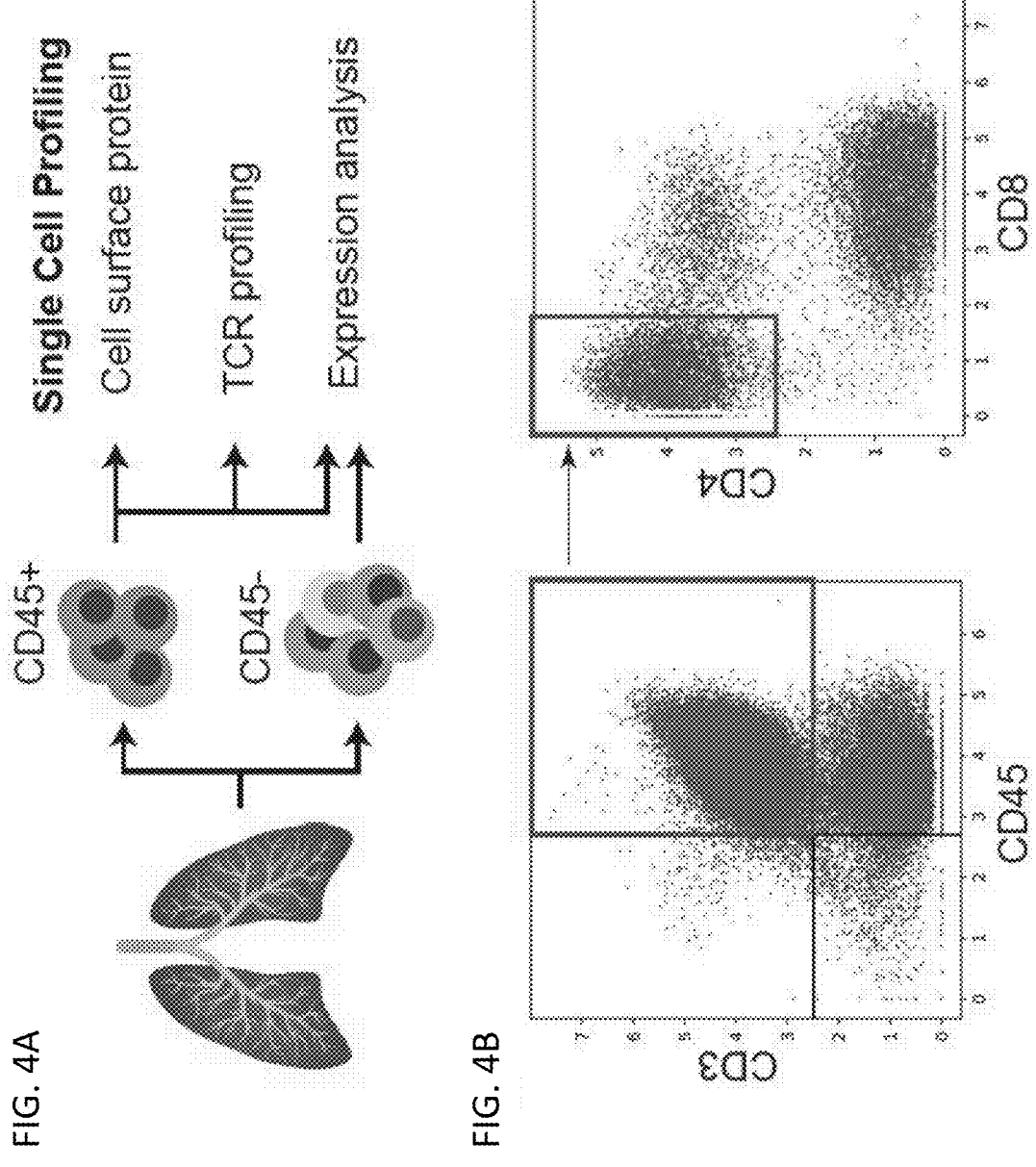
FIG. 4A-C. Single cell RNAseq identifies a subset of tumor infiltrating cytotoxic CD4+ T cells in NSCLC. A) Schematic overview of the experimental design. B) Gating strategy for the computational isolation of the CD4+ T cell compartment using CiteSeq. C) Non-negative matrix factorization (NMF) identified distinct transcriptional programs in the CD4+ T compartment. UMAP projection shows the cells labeled based on the most highly weighted transcriptional program.
Figure 4C:
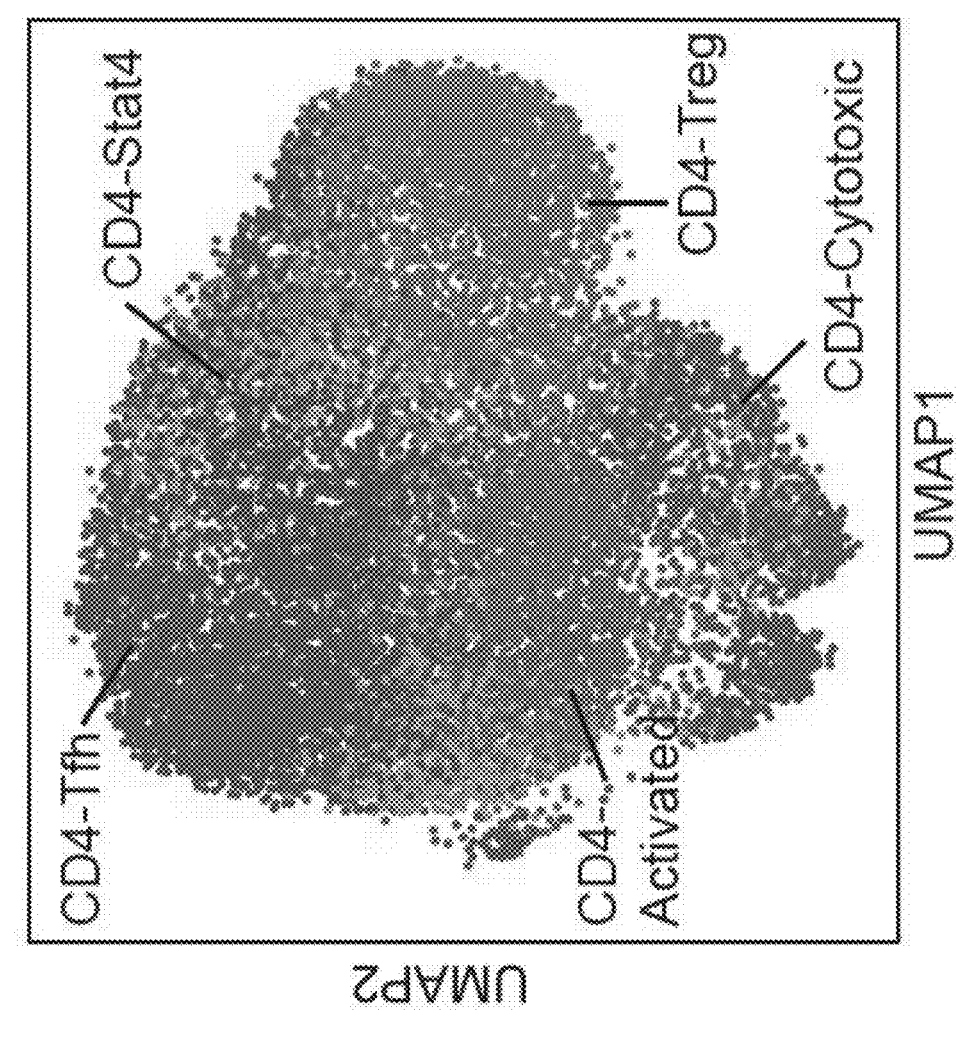
Figures 5A, 5B, 5C:
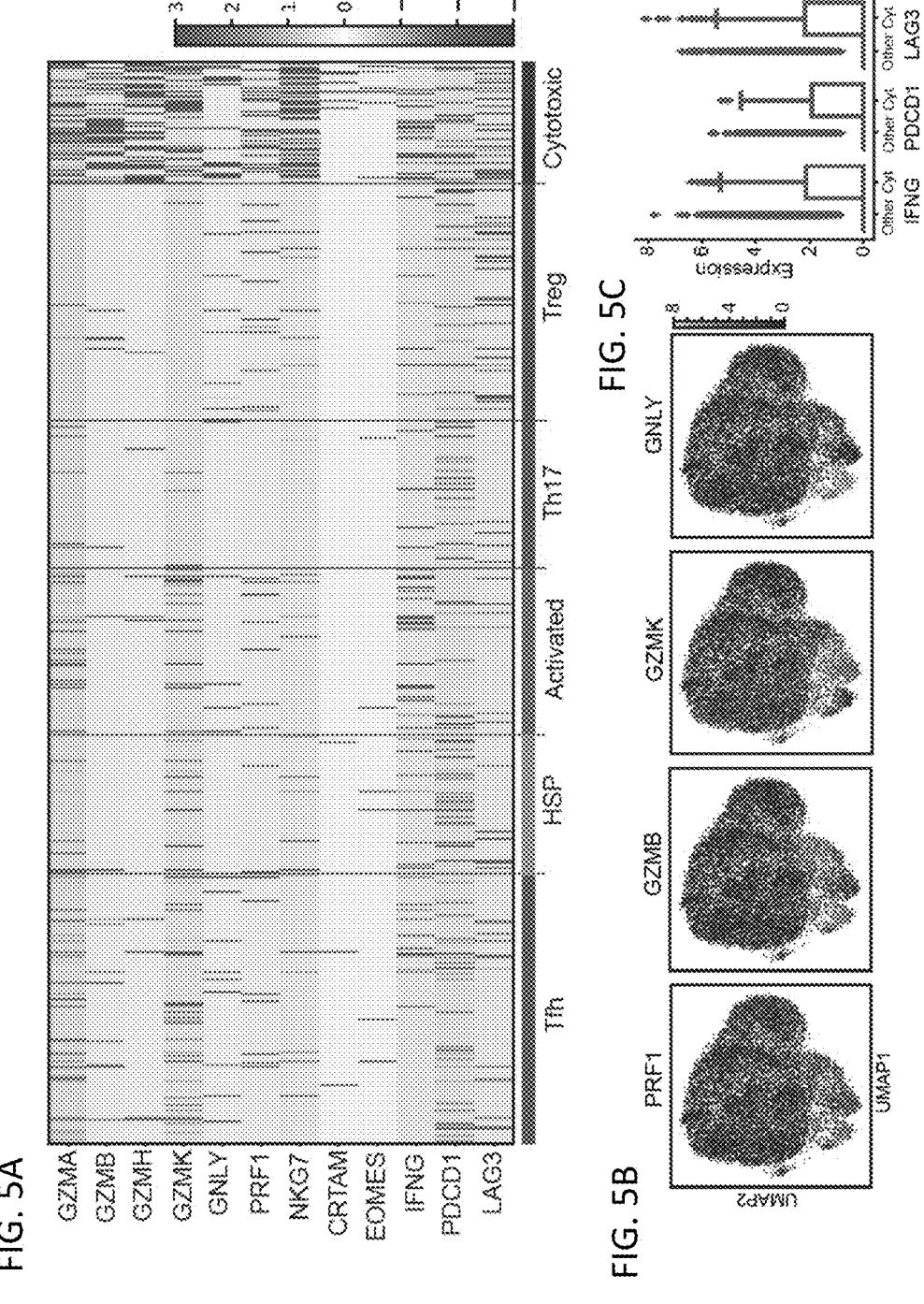
FIG. 5A-C. Cytotoxic CD4+ T cells have heterogeneous expression patterns of cytotoxic genes and upregulate IFNG and PD-1. A) Heatmap shows the expression of key cytotoxic and immune checkpoint genes in cytotoxic CD4+ T cell program. B) UMAP projections display the distinct patterns of expression for key cytotoxic genes. C) Expression of checkpoints IFNG, PDCD1, and LAG3 is higher in the cytotoxic population compared to the other CD4+ T cells ($p<0.0001$, $p<0.0001$, $p<0.0001$, Mann Whitney U).
Figures 6A, 6B, 6C:
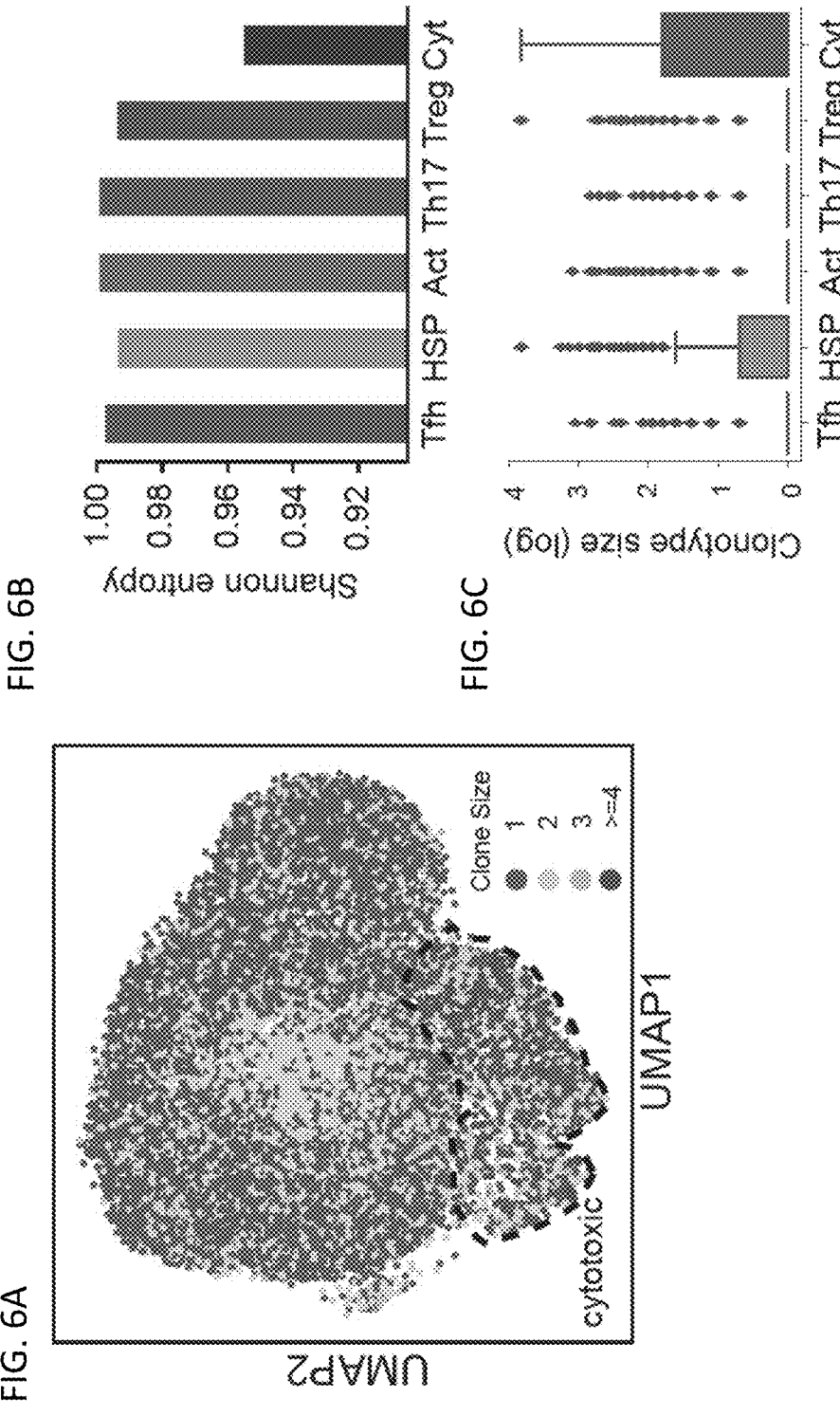
FIG. 6A-C. Cytotoxic CD4+ T cells are clonally expanded in NSCLC. A) UMAP projection showing the clone size associated with the TCR for each cell. B) TCR diversity, as measured by Shannon entropy, for each NMF cluster. C) Log transformed TCR clonotype size of the cytotoxic CD4+ T cell population compared to other CD4+ T cells ($p<0.001$, Kruskal Wallis).

Analysis of the single cell RNA sequencing data of the 10 NSCLC tumor samples identified a subset of tumor infiltrating cytotoxic CD4+ T cells in NSCLC dissociated tumor samples (FIG. 4). Thus, cytotoxic CD4+ T cells are present in the tumor infiltrating immune compartment of NSCLC patients. The cytotoxic CD4+ T cells exhibit heterogeneous expression patterns of cytotoxic genes and upregulate the checkpoint proteins IFNG, PDCD1, and LAG3 as compared to other CD4+ T cells (FIG. 5). Cytotoxic CD4+ T cells are clonally expanded in NSCLC tumor samples (FIG. 6). Further, the data showed that a subpopulation of NSCLC tumor cells express HLA class II molecules (HLA-II) (FIG. 7). Thus, these tumor cells can present antigen directly to cytotoxic CD4+ T cells via HLA-II.

Based on these results, a 20 gene signature for cytotoxicity (CCL5, GZMA, NKG7, CCL4, GZMH, CST7, GZMB, GZMK, GNLY, PRF1, CCL4L2, CD52, IL32, CD74, CTSW, CRIP1, CCL3, ITM2C, LAG3, and DUSP4) was developed. Each of the 148 patient's tumor was scored using this cytotoxic CD4+ gene signature, and it was shown that this cytotoxic score (CS/CYT score) is significantly associated with time to progression (TTP) in this cohort, including in patients that are HLA-I deficient (FIG. 8). Thus, this cytotoxicity is associated with checkpoint inhibitor response in NSCLC, and is independent of HLA-I status.

Figures 8A, 8B, 8C, 8D:
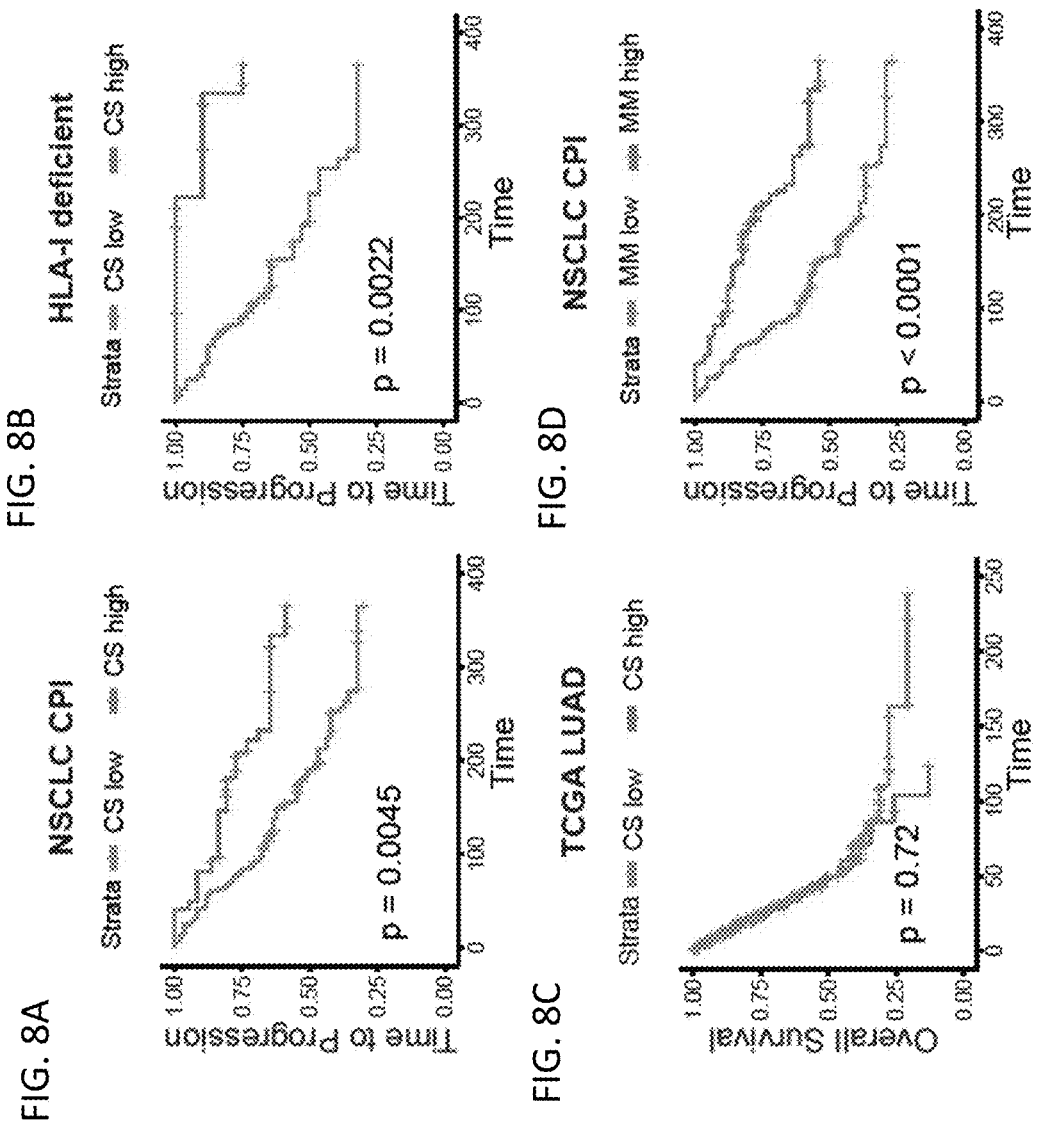
FIG. 8A-E. Gene signature of cytotoxicity is associated with CPI response in a real world NSCLC cohort, irrespective of HLA-I status. We developed a 20 gene signature for cytotoxicity. KM plots show that the cytotoxic score (CS) is significantly associated with TTP in patients in the A) Tempus NSCLC CPI cohort ($HR=0.42$), including the patients in the B) HLA-I deficient (LOH, homozygous or B2M mutation) sub-cohort ($HR=0.16$). As shown in figures A and B, the cytotoxic score is associated with IO response, even in HLA-1 deficient patients. C) CS is not associated with survival in the TCGA lung adenocarcinoma (LUAD) cohort ($HR=0.99$), which was primarily treated with chemotherapy. D) Combining CS with TMB into a simple multimodal model (MM) improves CPI response prediction compared to either biomarker alone ($HR=0.37$). E) TMB and CS are not significantly correlated ($R=0.031$, $p=0.71$, Pearson correlation).
Figure 8E:
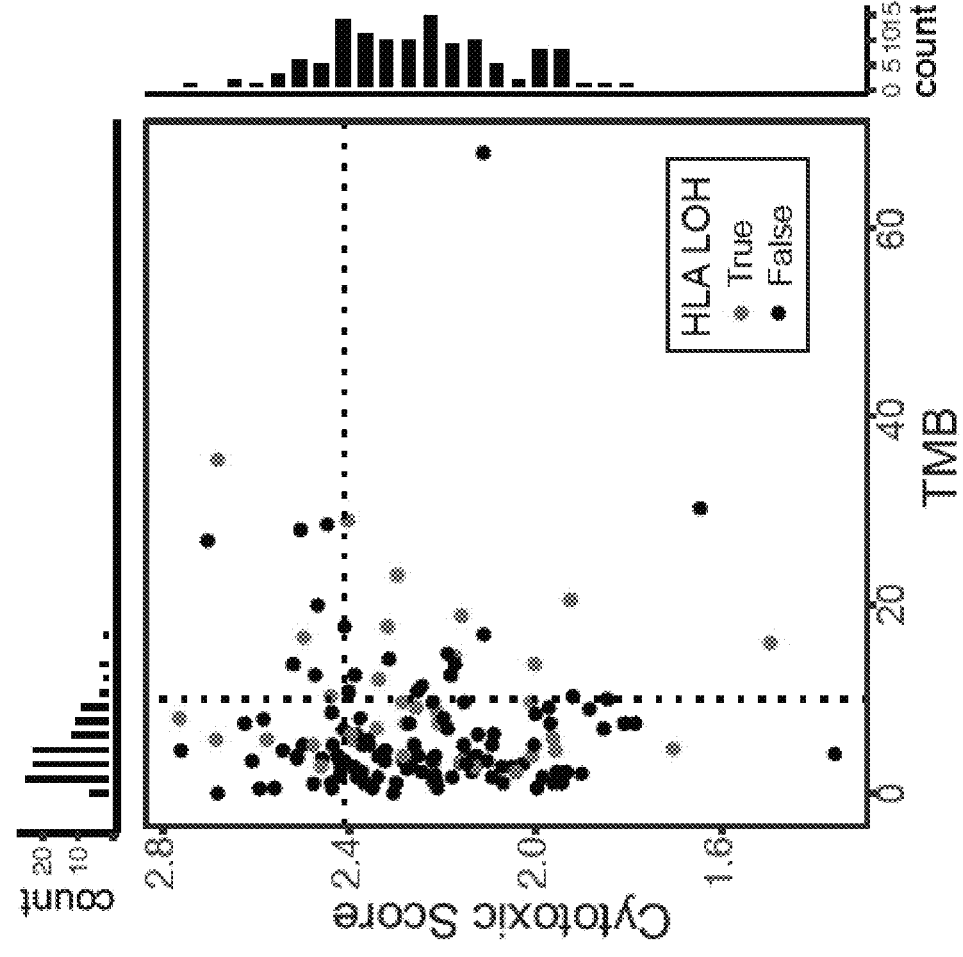

Additionally, it was found that combining the cytotoxic score (CYT score) (also termed (CS)) with the tumor mutational burden (TMB) in a simple multimodal model (MM) improves the ability to predict the response to a checkpoint inhibitor regime as compared to either indicator alone (FIG. 8D). Importantly, the TMB and CYT score/CS are not significantly correlated (FIG. 8E). Thus, TMB alone cannot be used to predict this CD4 cytotoxicity score.

C. Discussion

The methods described in this Example use next-generation sequencing of tumor biopsy samples to generate molecular-based progression risk scores that can help inform a physician's management of immuno-oncology (IO) therapy duration. The tumor immune microenvironment (TIME) modulates tumor killing by immune cells and has prognostic value in determining the clinical course and survival of an individual patient. DNA and RNA sequencing can measure tumor and immune intrinsic mechanisms of sensitization to IO in the tumor immune micro-environment (TIME), including the tumor mutational burden (TMB) of the cancer and the cytotoxicity of tumor infiltrating immune cells (CYT).

Example 7. Validation of IO Progression Risk

In various embodiments, validation may include clinical validation to evaluate the clinical utility of the model risk categories, cytotoxic score validation with analytical validation of the CYT gene signature, analytical validation of RNA gene expression, comparison of the cytotoxic score with multiplex IHC/IF, comparison of cytotoxic score between tumors sequenced on two RNA sequencing panels, and/or TMB validation. In one example, analytical validation of RNA gene expression includes a CAP/CLIA analytical validation, comprising universal human reference (UHR) RNA correlation to published qPCR data, inter-assay concordance study, intra-assay concordance study, dynamic range study, clinical linearity study, interfering substances study, and/or input Dynamic range study. In one example, comparison of the cytotoxic score with multiplex IHC/IF comprises performing multiplex IHC or IF on approximately 40 samples to identify the percentage of cytotoxic T cells present in tumor samples where the samples are selected to represent the dynamic range of the cytotoxic score (some samples will have a low CYT score, some will have a middle CYT score, some will have a high CYT score), and comparing the multiplex IHC/IF results with the cytotoxic score to assess how well the RNA signature reflects the status of the infiltrating immune population.

Retrospective clinical, real-world study of metastatic NSCLC patients treated with a CPI regimen to evaluate the ability of the IO Progression Risk test to distinguish patients with high progression risk from those with low progression risk and to evaluate the clinical utility of the model risk categories will be performed.

Patients from a database will be selected for the study cohort if they 1) met the test inclusion criteria, 2) were not used in model training, 3) had at least 90 days of clinical follow up from treatment initiation or had a documented progression event and 4) completed DNA and RNA sequencing analysis.

The two primary endpoints in the study will be time to progression (TTP) and progression at 6 months. TTP is defined as time from IO treatment initiation to disease progression (the first progression event), censored at the last known physician contact, death, or treatment stop for reason other than progression. TTP will be evaluated for all patients. TTP will be measured using the Kaplan-Meier method and hazard ratios and associated confidence intervals will be calculated using the Cox proportional-hazards model. Progression at 6 months will be defined as whether the patient experienced disease progression within the first 6 months of CPI treatment and was evaluated for all patients with at least 6 months of clinical follow up or had a documented progression event.

Criteria for model acceptance in one example: Hazard ratio of a stratified survival model must be greater than 1.75 and the log rank test p value must be less than 0.05. Strata for the model will be regimen type. TTP=time to progression.

hi_risk=binary variable, where 1 represents patients labelled as high risk.
  io_monotherapy=binary variable where 1 represents patients who received IO as a monotherapy.

$$TTP \sim hi\_risk + strata(io\_monotherapy)$$

It is anticipated that patients classified by the IO Progression Risk Test as high progression risk will have significantly worse clinical outcomes than those classified as low progression risk. Kaplan-Meier analysis is anticipated to demonstrate a significant difference in TTP based on the IO Progression Risk test labels.

Example 8. Cytotoxic CD4+ T Cells Explain Anti-Tumor Immune Responses in HLA Class I Impaired NSCLC Summary: Immune checkpoint blockade (ICB) has produced long-term clinical responses in a portion of patients having metastatic non-small-cell lung cancer (NSCLC). However, the efficacy of ICB varies greatly across patients and treatment resistance is a major cause of disease progression and mortality. The disruption of HLA class I antigen presentation in tumors, through mechanisms such as mutations in B2M or loss of heterozygosity at the HLA class I locus (HLA-LOH), have been proposed as important mechanisms of resistance to ICB. However, real-world studies in a variety of cancer types have found that some patients, despite having disrupted HLA class I presentation in their tumor, still have durable responses to ICB. We sought to determine the existence of an HLA-I independent mechanism of ICB response in NSCLC. Here, we use single cell multiomic profiling (a combination of single-cell RNA sequencing, TCR sequencing, and surface protein profiling) to identify a population of CD4+ T cells that are tumor-infiltrating, clonally expanded, and express a canonical cytotoxic gene program. Concordantly, we found tumor cells with elevated HLA class II expression in NSCLC patients. Finally, we show that a cytotoxic gene signature is associated with improved progression-free survival (longer amount of time before progression) in a real-world cohort of NSCLC patients treated with ICB regimens, including those with loss of heterozygosity at the HLA class I locus. Overall, these results suggest a model where cytotoxic CD4+ T cells can perform direct tumor cell killing in a class II restricted manner in NSCLC.

Introduction: PD-1 and PD-L1 immune checkpoint blockade (ICB) has produced long-term clinical responses in metastatic non-small-cell lung cancer (NSCLC) (for example, see Martinez, P., Peters, S., Stammers, T. & Soria, J.-C. Immunotherapy for the First-Line Treatment of Patients with Metastatic Non-Small Cell Lung Cancer. Clin. Cancer Res. 25, 2691-2698 (2019) or Garon, E. B. et al. Five-Year Overall Survival for Patients With Advanced Non-Small-Cell Lung Cancer Treated With Pembrolizumab: Results From the Phase I KEYNOTE-001 Study. J. Clin. Oncol. Off. J. Am. Soc. Clin. Oncol. 37, 2518-2527 (2019), the contents of each of which are incorporated by reference herein in their entirety for any and all purposes). However, clinical response rates and duration of response are highly variable and ICB mechanisms of action in patients are incompletely understood. Furthermore, current biomarkers, namely immunohistochemistry assays for tumor expression of PD-L1 have been found to have limited predictive power. In the prevailing model of ICB, the primary mechanism for direct tumor cell killing occurs through a cytotoxic CD8+ T cell mediated response via tumor cell antigen presentation on class I human leukocyte antigen (HLA-I) molecules. The disruption of HLA class I antigen presentation in tumors, through mechanisms such as mutations in its co-receptor, beta 2 microglobulin (B2M), or loss of heterozygosity at the HLA class I locus (HLA-LOH), have been proposed as important mechanisms of primary and adaptive resistance to ICB (for example, see Sade-Feldman, M. et al. Resistance to checkpoint blockade therapy through inactivation of antigen presentation. Nat. Commun. 8, 1136 (2017); Gettinger, S. et al. Impaired HLA Class I Antigen Processing and Presentation as a Mechanism of Acquired Resistance to Immune Checkpoint Inhibitors in Lung Cancer. Cancer Discov. 7, 1420-1435 (2017); Zaretsky, J. M. et al. Mutations Associated with Acquired Resistance to PD-1 Blockade in Melanoma. N. Engl. J. Med. 375, 819-829 (2016); the contents of each of which are incorporated by reference herein in their entirety for any and all purposes). Accordingly, the rate of HLA-LOH has been reported as high as 40% in NSCLC patients (for example, see McGranahan, N. et al. Allele-Specific HLA Loss and Immune Escape in Lung Cancer Evolution. Cell 171, 1259-1271.e11 (2017), the contents of which are incorporated by reference herein in their entirety for any and all purposes) and has been linked to worse survival on ICB (for example, see Chowell, D. et al. Patient HLA class I genotype influences cancer response to checkpoint blockade immunotherapy. Science 359, 582-587 (2018), the contents of which are incorporated by reference herein in their entirety for any and all purposes). However, evidence has emerged that patients with disrupted tumor HLA-I presentation can have durable responses to ICB (for example, see Shim, J. H. et al. HLA-corrected tumor mutation burden and homologous recombination deficiency for the prediction of response to PD-(L) 1 blockade in advanced non-small-cell lung cancer patients. Ann. Oncol. 31, 902-911 (2020); Litchfield, K. et al. Meta-analysis of tumor- and T cell-intrinsic mechanisms of sensitization to checkpoint inhibition. Cell (2021) doi: 10.1016/j.cell.2021.01.002; Rodig, S. J. et al. MHC proteins confer differential sensitivity to CTLA-4 and PD-1 blockade in untreated metastatic melanoma. Sci. Transl. Med. 10, (2018); or Anagnostou, V. et al. Multimodal genomic features predict outcome of immune checkpoint blockade in non-small-cell lung cancer. Nat. Cancer 1, 99-111 (2020), the contents of each of which are incorporated by reference herein in their entirety for any and all purposes). This indicates that an HLA class I independent pathway for anti-tumor immunity exists and may be sufficient in some patients to modulate long-term tumor control.

One possible mechanism for an HLA class I independent immune response is through CD4+ T cells. Classically, effector CD4+ T cells play a supportive role to CD8+ T cells via dendritic cell licensing and secretion of pro-inflammatory cytokines (for example, see, Borst, J., Ahrends, T., Babala, N., Melief, C. J. M. & Kastenmüller, W. CD4+ T cell help in cancer immunology and immunotherapy. Nat. Rev. Immunol. 18, 635-647 (2018); or Tay, R. E., Richardson, E. K. & Toh, H. C. Revisiting the role of CD4+ T cells in cancer immunotherapy—new insights into old paradigms. Cancer Gene Ther. 1-13 (2020) doi:10.1038/s41417-020-0183-x, the contents of each of which are incorporated by reference herein in their entirety for any and all purposes). However, earlier studies in animal models have shown that CD4+ T cells, which recognize antigen via HLA class II rather than HLA class I, can directly kill tumor cells. Additionally, a number of pre-clinical studies using single cell RNA sequencing (scRNAseq) have recently identified cytotoxic CD4+ T cells in various cancers, including melanoma, breast cancer, hepatocellular carcinoma, and head and neck cancer (for example, see, Xie, Y. et al. Naive tumor-specific CD4(+) T cells differentiated in vivo eradicate established melanoma. J. Exp. Med. 207, 651-667 (2010); Quezada, S. A. et al. Tumor-reactive CD4+ T cells develop cytotoxic activity and eradicate large established melanoma after transfer into lymphopenic hosts. J. Exp. Med. 207, 637-650 (2010); Sledzińska, A. et al. Regulatory T Cells Restrain Interleukin-2- and Blimp-1-Dependent Acquisition of Cytotoxic Function by CD4+ T Cells. Immunity 52, 151-166.e6 (2020); or Takeuchi, A. et al. CRTAM determines the CD4+ cytotoxic T lymphocyte lineage. J. Exp. Med. 213, 123-138 (2015), the contents of each of which are incorporated by reference herein in their entirety for any and all purposes). Furthermore, a heterogeneous population of cytotoxic CD4+ T cells were identified in bladder cancer that were associated with improved response to ICB. While cytotoxic CD4+ T cells have yet to be identified in NSCLC, a number of studies have found that HLA class II, which is typically expressed only on immune cells, can also be expressed on NSCLC tumor cells (for example, see, Neuwelt, A. J. et al. Cancer cell-intrinsic expression of MHC II in lung cancer cell lines is actively restricted by MEK/ERK signaling and epigenetic mechanisms. J. Immunother. Cancer 8, (2020); Kamma, H., Yazawa, T., Ogata, T., Horiguchi, H. & Iijima, T. Expression of MHC class II antigens in human lung cancer cells. Virchows Arch. B Cell Pathol. Incl. Mol. Pathol. 60, 407-412 (1991); or He, Y. et al. MHC class II expression in lung cancer. Lung Cancer Amst. Neth. 112, 75-80 (2017), the contents of each of which are incorporated by reference herein in their entirety for any and all purposes). We therefore sought to determine the existence and mechanism of this axis in NSCLC, the largest patient population indicated for ICB therapy.

Here, we used single cell multiomic profiling, to evaluate the tumor and T cell compartments in NSCLC tumors from 10 patients representing smoker and never-smoker populations. We identified a robust population of tumor-infiltrating, clonally expanded CD4+ T cells expressing a canonical cytotoxic gene program, as well as tumor cells with elevated HLA class II expression in NSCLC. We further determined that a gene signature of cytotoxic T cells was associated with ICB outcomes in a real-world cohort of NSCLC patients, including HLA-I disrupted and HLA-I intact tumors. Overall, this study demonstrates that tumor infiltrating cytotoxic CD4+ T cells exist in NSCLC, and that they may mediate anti-tumor immunity in NSCLC patients. Our findings also suggest that future ICB biomarker and immunotherapy development should account for this HLA-I independent mechanism of ICB response.

Results

HLA class I deficient NSCLC patients can have durable responses to checkpoint inhibitors: To evaluate whether patients with HLA-I disrupted NSCLC tumors are able to experience responses to ICB, we assembled a real-world cohort of 147 patients with metastatic, non-squamous NSCLC from a proprietary database, who were treated with standard of care ICB. Patients with actionable EGFR or ALK alterations were excluded from the cohort. This exclusion criterion is based on NCCN guidelines that all metastatic NSCLC patients, regardless of PD-L1 status, are to receive immune checkpoint therapy (either as a monotherapy or in combination with platinum chemotherapy) unless the patient has an actionable an ALK alteration or EGFR mutation. Baseline (ICB naïve) patient samples were profiled using targeted DNA sequencing (for example, see Beaubier, N. et al. Clinical validation of the tempus xT next-generation targeted oncology sequencing assay. Oncotarget 10, 2384-2396 (2019); or Beaubier, N. et al. Clinical validation of the Tempus xO assay. Oncotarget 9, 25826-25832 (2018), the contents of each of which are incorporated by reference herein in their entirety for any and all purposes) or whole exome sequencing, along with whole transcriptome RNA sequencing. Additionally, DNA sequencing was performed on matched normal samples when available (121/147). Response to therapy was evaluated using time to progression (TTP) (for example, see Griffith, S. D. et al. Characterizing the Feasibility and Performance of Real-World Tumor Progression End Points and Their Association With Overall Survival in a Large Advanced Non-Small-Cell Lung Cancer Data Set. JCO Clin. Cancer Inform. 3, 1-13 (2019), the contents of which are incorporated by reference herein in their entirety for any and all purposes) with a median cohort TTP of 226 days. 45% of patients received ICB as a monotherapy while the rest were treated in combination with chemotherapy. Other clinical metrics are detailed in Table 4.

TABLE 4

| NSCLC IO Cohort characteristics | |
| --- | --- |
| | n (%) |
| Total cohort | 147 (100) |
| Sex | |
| Female | 71 (48) |
| Male | 76 (51) |

TABLE 4-continued

| NSCLC IO Cohort characteristics | |
| --- | --- |
| | n (%) |
| Age | |
| <=40 | 4 (3) |
| 41-60 | 28 (19) |
| 61-80 | 97 (66) |
| >=81 | 12 (8) |
| ECOG performance status | |
| 0 | 19 (13) |
| 1 | 30 (20) |
| 2 | 10 (7) |
| unknown | 87 (59) |
| Line of Therapy | |
| 1 | 61 (41) |
| 2+ | 86 (58) |
| Regimen | |
| Pembro monotherapy | 32 (22) |
| Pembro combination | 63 (43) |
| Nivo monotherapy | 35 (24) |
| Atezo monotherapy | 8 (5) |
| Atezo combination | 5 (3) |
| Durva monotherapy | 2 (1) |

TABLE 5

| NSCLC Platinum Cohort characteristics | |
| --- | --- |
| | n (%) |
| Total cohort | 95 (100) |
| Sex | |
| Female | 46 (45) |
| Male | 49 (48) |
| Age | |
| <=40 | 1 (1) |
| 41-60 | 24 (25) |
| 61-80 | 64 (67) |
| >=81 | 6 (6) |
| Regimen | |
| platinum doublet | 85 (89) |
| platinum doublet + bevacizumab | 10 (11) |

Figure 9A:
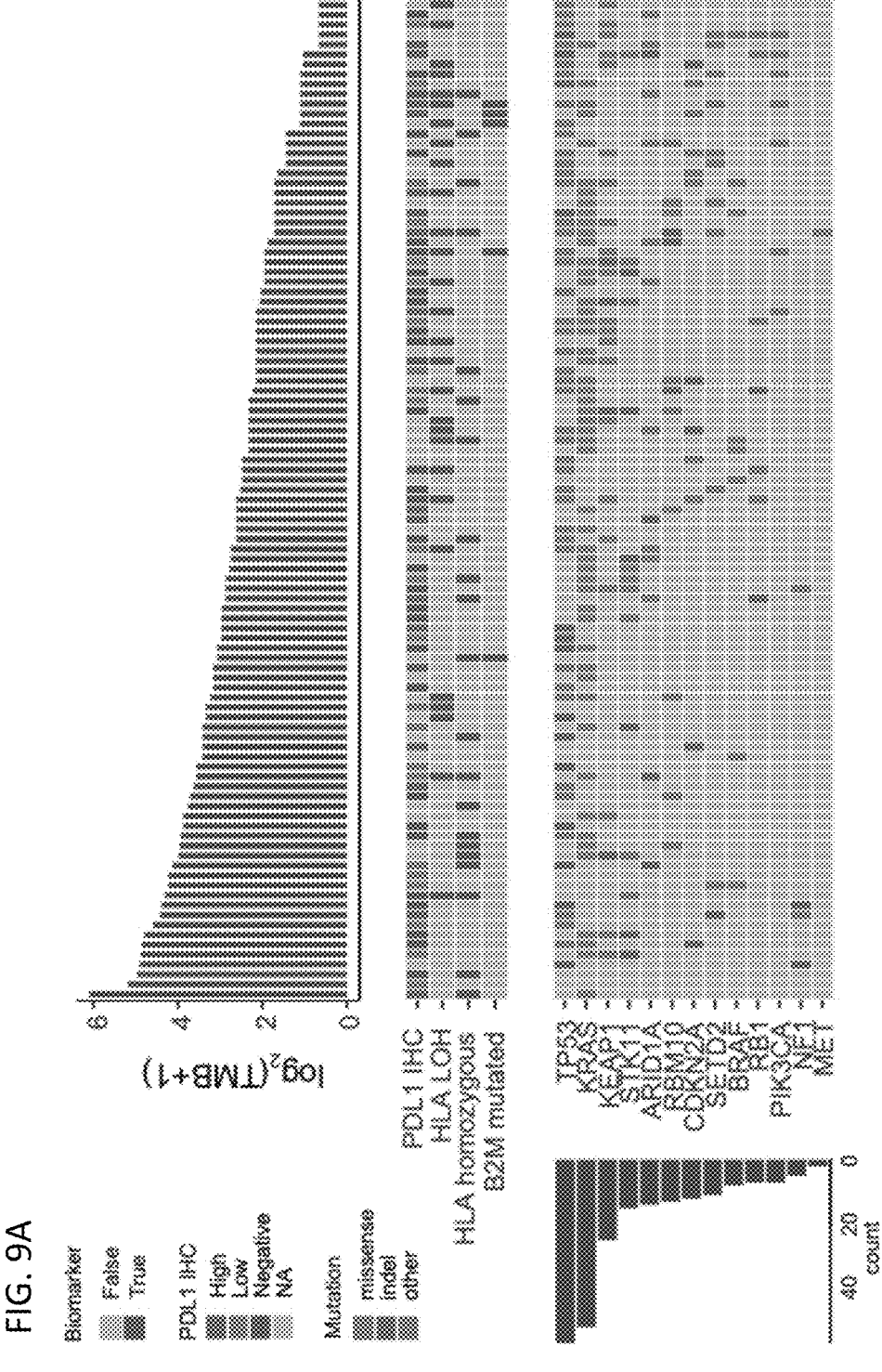

The most commonly mutated driver genes were TP53 (58%), followed by KRAS (45%) and KEAP1 (22%) (FIG. 9A). Other examples of mutated driver genes include STK11, ALK, EGFR, etc. In the future, more genes may be determined to be driver genes for NSCLC. There was no significant relationship between mutation status and TTP for any of the driver genes listed in FIG. 9. In this cohort, we also looked at a number of previously described immunotherapy biomarkers, such as PDL1 expression, TMB, and HLA-LOH. PDL1 high patients had modestly better TTP than PDL1 negative and low patients (HR=0.56, p=0.07, log rank) (FIG. 9B). Additionally, this cohort's tumors were highly mutated, with a median tumor mutational burden (TMB) of 4.93 mutations per megabase and patients with a high TMB (more than 10 mutations per megabase) had significantly longer TTP than those with a low TMB (HR=0.42, p=0.0057, log rank) (FIG. 9C).

Figures 14A, 14B, 14C:
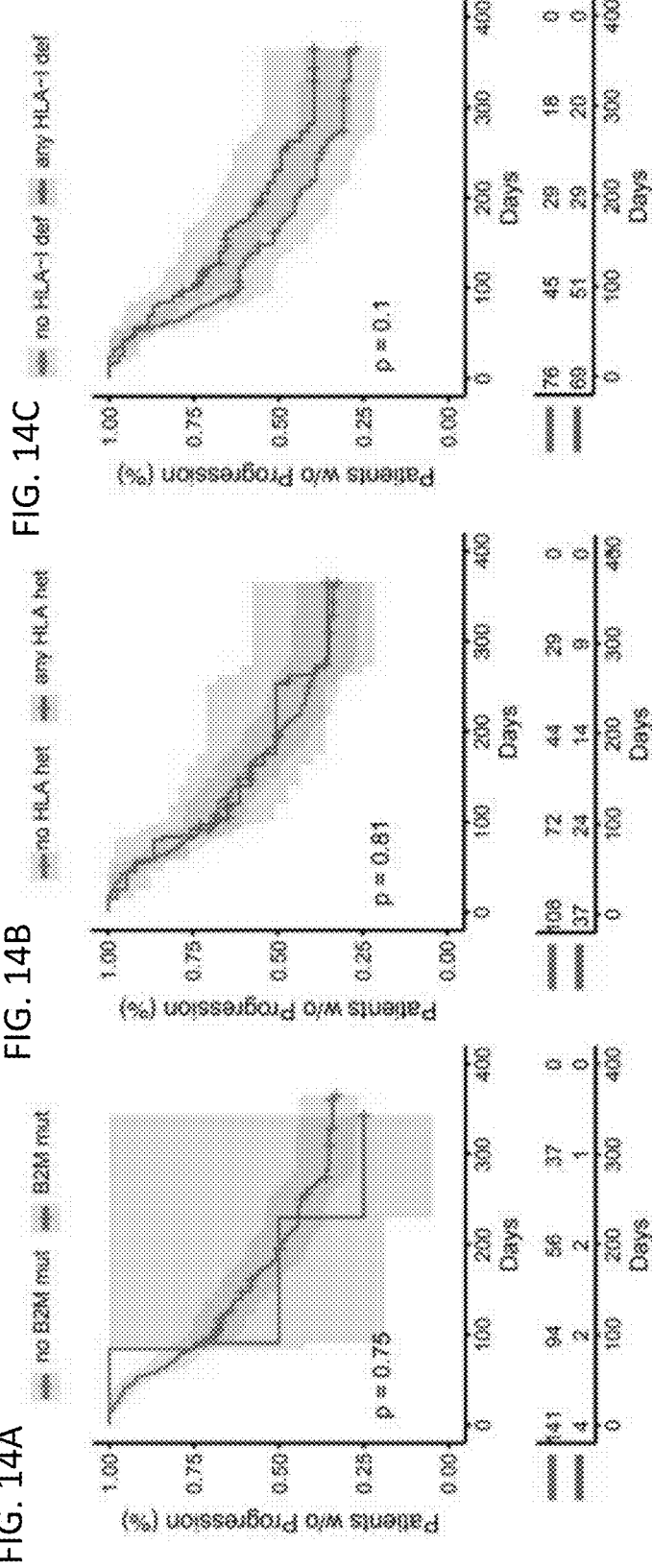
FIG. 14A-C. HLA class I deficiencies and TTP in the NSCLC IO cohort. A, Kaplan-Meier plots showing time to progression on ICB therapy, stratified by HLA LOH status ($p=0.23$, $HR=0.69$, Cox PH), B, HLA homozygosity status ($p=0.8$, $HR=0.92$, Cox PH), and C, B2M mutation status ($p=0.62$, $HR=0.71$, Cox PH).

Similar to previous studies (for example, see McGranahan et al (2017) or Chowell et al (2018)), we found that a significant proportion of the real-world cohort had defects in class I antigen presentation, with 27% having loss of heterozygosity in at least one HLA class I allele and 5% having a B2M mutation (FIG. 9A, center). Furthermore, 21% of patients were homozygous for at least one HLA class I allele. There was no significant association between these class I features and TTP, either individually or in combination (HLA LOH: p=0.13, HR=0.56, B2M: p=0.78, HR=0.85, HLA homozygosity: p=0.90, HR=0.97, pooled: p=0.04, HR=0.58, log rank) (FIGS. 9D, 14). These data show that some patients with limitations in class I antigen presentation are still able to have durable clinical responses to immunotherapy, lending credence to the existence of a class I independent mechanism for ICB response in NSCLC patients.

Figure 10A:
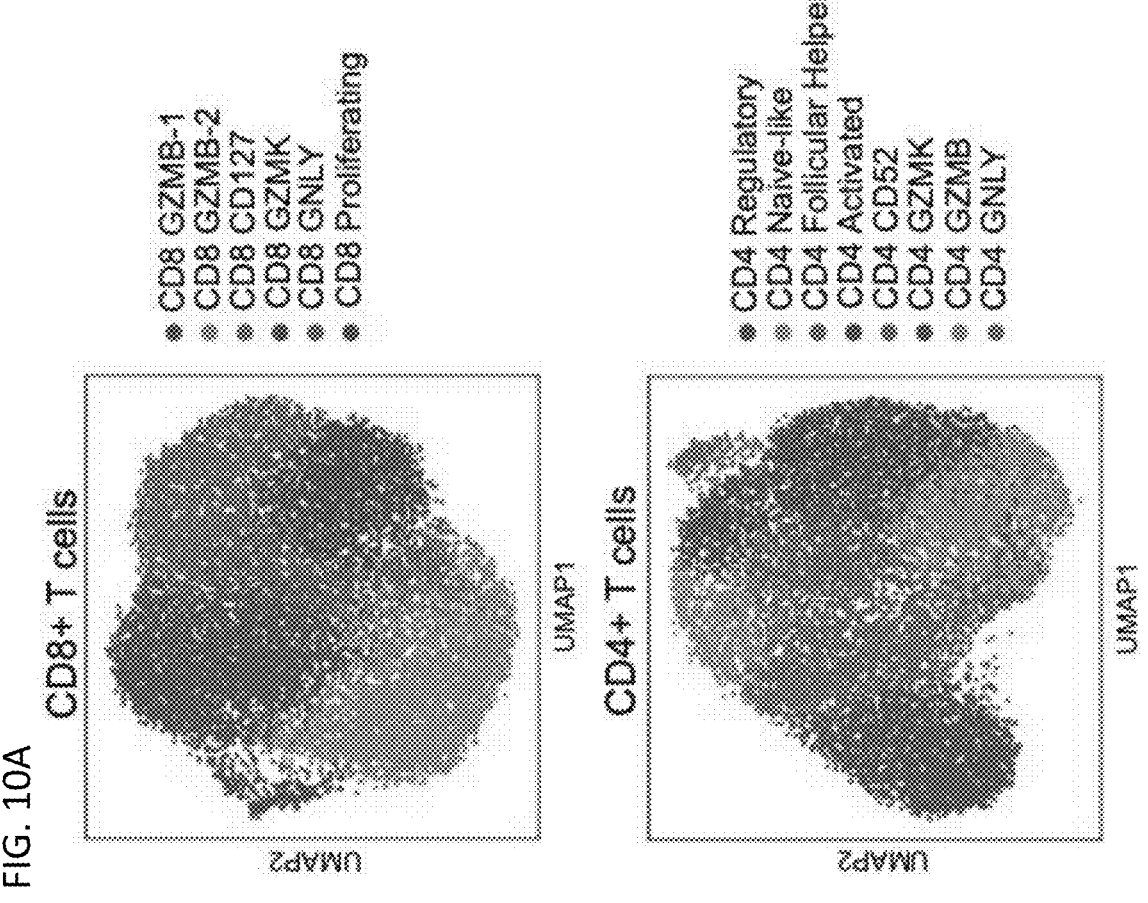
FIG. 10A-D. A-C) UMAP projections show the distinct patterns of expression for the cytotoxic genes PRF1, GZMB, GZMK, and GNLY. D) Boxplots show the log transformed RNA expression of IFNG of the Leiden clusters. * represent clusters with significantly different expression ($p<0.05$) compared to the other clusters (Wilcoxon rank sum).

Identification of multiple cytotoxic T cell sub-populations in NSCLC: To identify HLA-I independent mechanisms of ICB response, we performed single cell profiling on 10 dissociated tumor samples obtained from treatment naive NSCLC patients. Samples were separated into CD45+ and CD45− fractions using flow cytometry, and then subjected to gene expression profiling through scRNAseq using the 10× Genomics Chromium platform. The CD45+ fraction additionally underwent single cell TCR and cell surface protein profiling using a panel of DNA-barcoded antibodies (FIG. 4A). We profiled 2,806 CD45− cells and 62,723 CD45+ cells. We computationally isolated the CD4+ T cell compartment (16,008 cells) and the CD8+ T cell compartment (13,935 cells) for our analysis using protein expression of lineage specific markers (FIG. 4B). After filtering on highly variable genes and scaling the expression data to unit variance, we performed Leiden clustering to identify sub-populations within the CD4+ and CD8+ T cell compartments with distinct transcriptional programs (FIG. 10A).

Figure 10B:
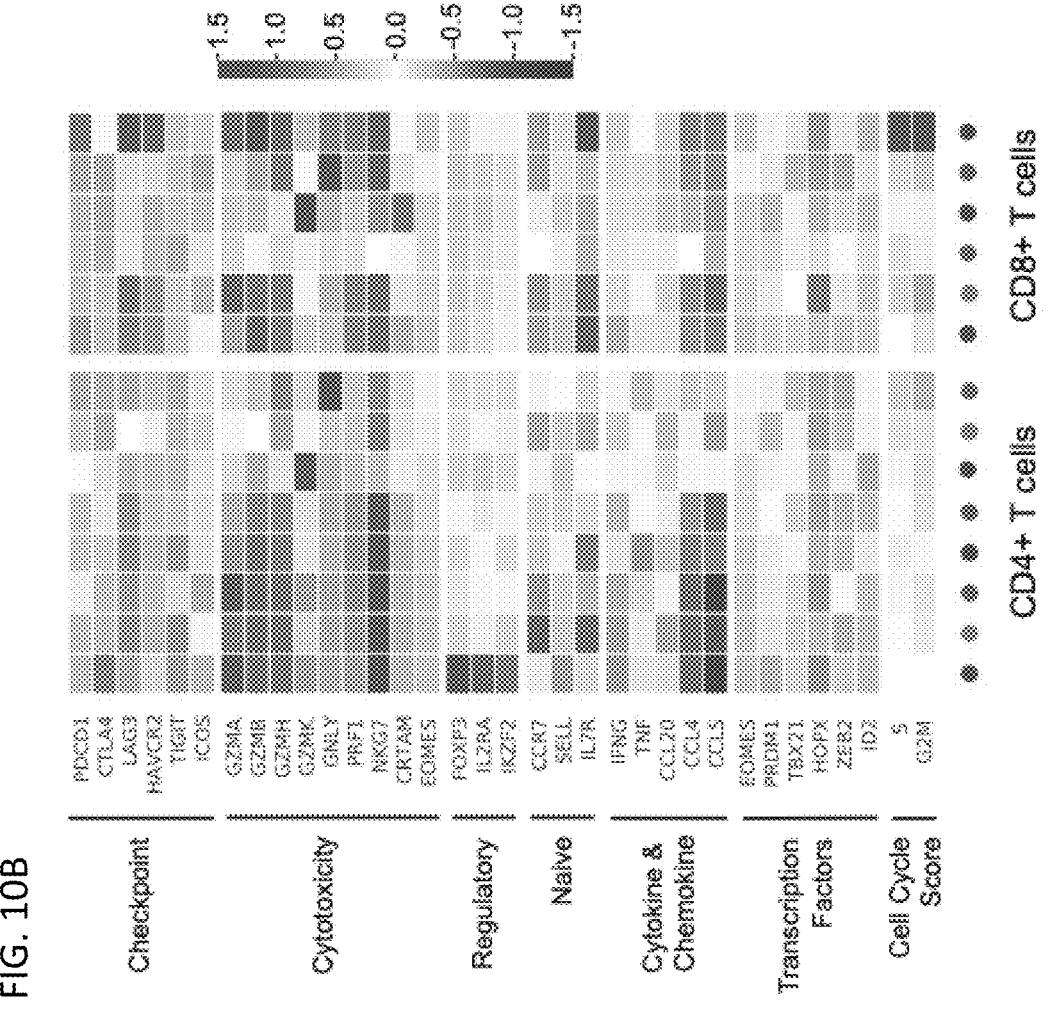
Figure 10C:
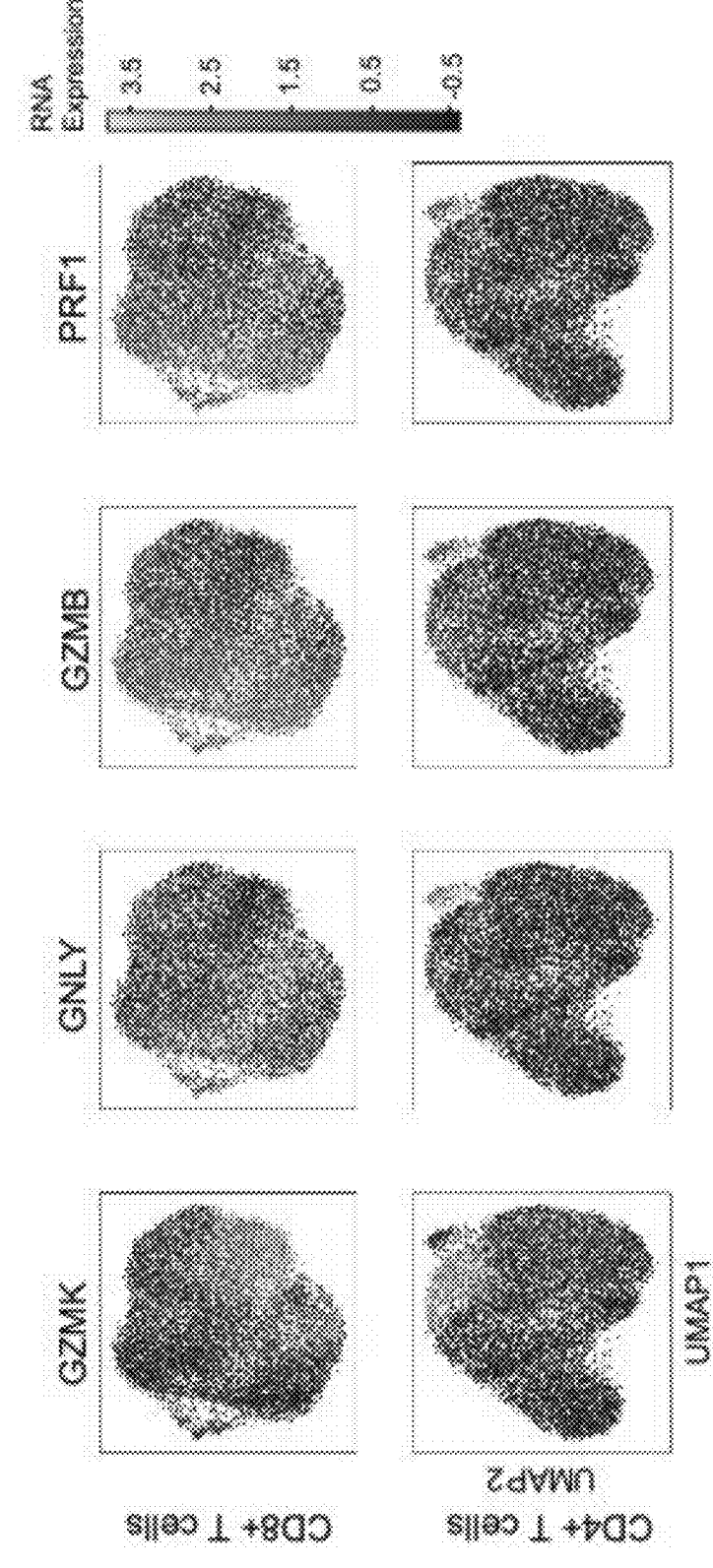
Figures 15A, 15B:
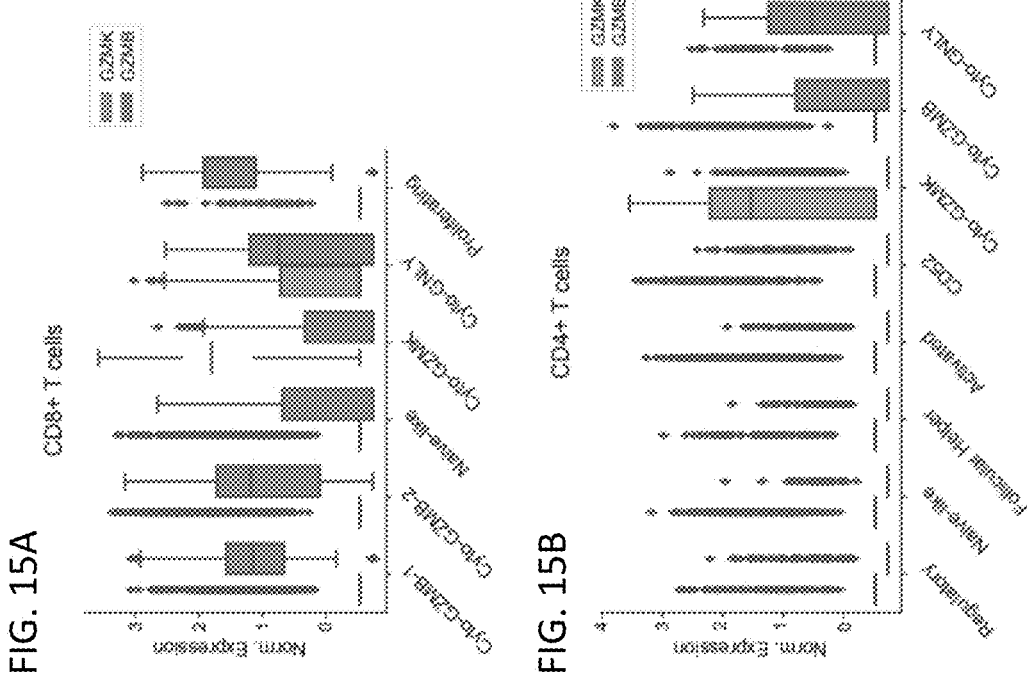
FIG. 15A-B. GZMB and GZMK expression in CD4+ and CD8+ T cells. A, Normalized RNA expression of GZMK and GZMB for each Leiden cluster in the CD8+ and B, CD4+ T cell population.

Within the CD8+ T cell compartment, we identified six sub-populations. Notably, five of the six clusters, $CD8_{GZMK}$, $CD8_{GNLY}$, $CD8_{GZMB-1}$, CD8GZMB-2, and $CD8_{prolif}$ exhibited elevated expression of canonical cytotoxic genes, including granzymes and perforins, as well as associated transcription factors like EOMES and CRTAM (FIG. 10B). We found that the pattern of expression for specific cytotoxic genes varied across the CD8+ T cell compartment (FIG. 10C). Expression of granzyme factors GZMA, GZMH, and NKG7 occurred broadly across the cytotoxic CD8+ population, however, elevated expression of GZMB and GZMK was observed in distinct clusters (FIGS. 10C, 15A). CRTAM, an immunoglobulin superfamily protein induced after TCR activation (for example, see Boles, K. S., Barchet, W., Diacovo, T., Cella, M. & Colonna, M. The tumor suppressor TSLC1/NECL-2 triggers NK-cell and CD8+ T-cell responses through the cell-surface receptor CRTAM. Blood 106, 779-786 (2005); or Takeuchi, A. et al. CRTAM confers late-stage activation of CD8+ T cells to regulate retention within lymph node. J. Immunol. Baltim. Md. 1950 183, 4220-4228 (2009), the contents of each of which are incorporated herein by reference in their entirety for any and all purposes) was primarily expressed in the CD8GZMK population, suggesting that they are in an earlier stage of effector cell differentiation than the other cytotoxic CD8 populations. Interestingly, the CD8GNLY cluster, which had the highest expression of the pore forming peptide granulysin (GNLY), expressed both GZMB and GZMK, suggesting an intermediate state in between the CD8GZMK and CD8GZMB clusters.

The two GZMB high clusters, CD8GzMB-1 and CD8GZMB-2, share a number of characteristics. They both express CD103 and CD39, a phenotype that has been previously shown to enrich for tumor reactive T cells (for example, see Duhen, T. et al. Co-expression of CD39 and CD103 identifies tumor-reactive CD8 T cells in human solid tumors. Nat. Commun. 9, 2724 (2018); or Franciszkiewicz, K. et al. Intratumoral induction of CD103 triggers tumor-specific CTL function and CCR5-dependent T-cell retention. Cancer Res. 69, 6249-6255 (2009), the contents of each of which are incorporated by reference herein in their entirety for any and all purposes). They also express high levels of immune checkpoint genes, like PDCD1, LAG3 and TIGIT, suggesting that they are exhausted and could be targeted using ICB regimens. Additionally, they also express CXCL13, which has previously been shown to be associated with better response and survival in NSCLC patients treated with PD-1 blockade, due to improved immune cell recruitment to tertiary lymphoid structures (for example, see Thommen, D. S. et al. A transcriptionally and functionally distinct PD-1+CD8+ T cell pool with predictive potential in non-small cell lung cancer treated with PD-1 blockade. Nat. Med. 24, 994-1004 (2018), the contents of which are incorporated by reference herein in their entirety for any and all purposes). Interestingly, the $CD8_{GZMB-1}$ population is enriched for FABP5 and 41BB expressing cells, which is a sign of increased oxidative metabolism. A similar population has been observed in hepatocellular carcinoma, and the metabolic adaptation of these cells is hypothesized to provide a survival advantage in the tumor microenvironment (for example, see Liu, F. et al. Identification of FABP5 as an immunometabolic marker in human hepatocellular carcinoma. J. Immunother. Cancer 8, e000501 (2020), the contents of which are incorporated by reference herein in their entirety for any and all purposes).

Another cytotoxic cluster, $CD8_{prolif}$, appears to be actively proliferating as shown by high S and G2M cell cycle scores and elevated MKI67 expression relative to other clusters. These cells most likely represent clones that were recently TCR stimulated and are now undergoing active clonal expansion (FIG. 10B). The only non-cytotoxic cluster, $CD8_{naïve-like}$, expressed markers such as CCR7 and IL7R, and most likely represent bystander T cells.

Within the CD4+ T cell compartment, we also identified populations of cytotoxic T cells as has been previously described in other cancers (for example, see Xie et al (2010), Quezada et al (2010), Śledzińska et al (2020), or Takeuchi et al (2015)). Similar to the CD8+ T cells, the cytotoxic gene expression pattern was also heterogeneous, broadly following the same patterns observed as in the CD8+ T cell compartment (FIG. 10C). GZMB and GZMK expression was again elevated in distinct clusters (FIGS. 10C, 15B). The GNLY high cluster, CD4GNLY, co-expressed GZMB, but not GZMK. CRTAM and EOMES, both genes associated with induction of the cytotoxic program in CD4 T cells (for example, see Takeuchi et al (2015) or Takeuchi, A. & Saito, T. CD4 CTL, a Cytotoxic Subset of CD4+ T Cells, Their Differentiation and Function. Front. Immunol. 8, (2017), the contents of which are incorporated herein by reference in their entirety for any and all purposes) were most highly expressed in the CD4GZMK population, similar to the $CD8_{GZMK}$ cells. Interestingly, the $CD4_{GZMB}$ cluster but not the $CD4_{GZMK}$ or $CD4_{GNLY}$ clusters, expressed high levels of immune checkpoints such as PDCD1 and CTLA4 (FIG. 10B).

Figure 10D:
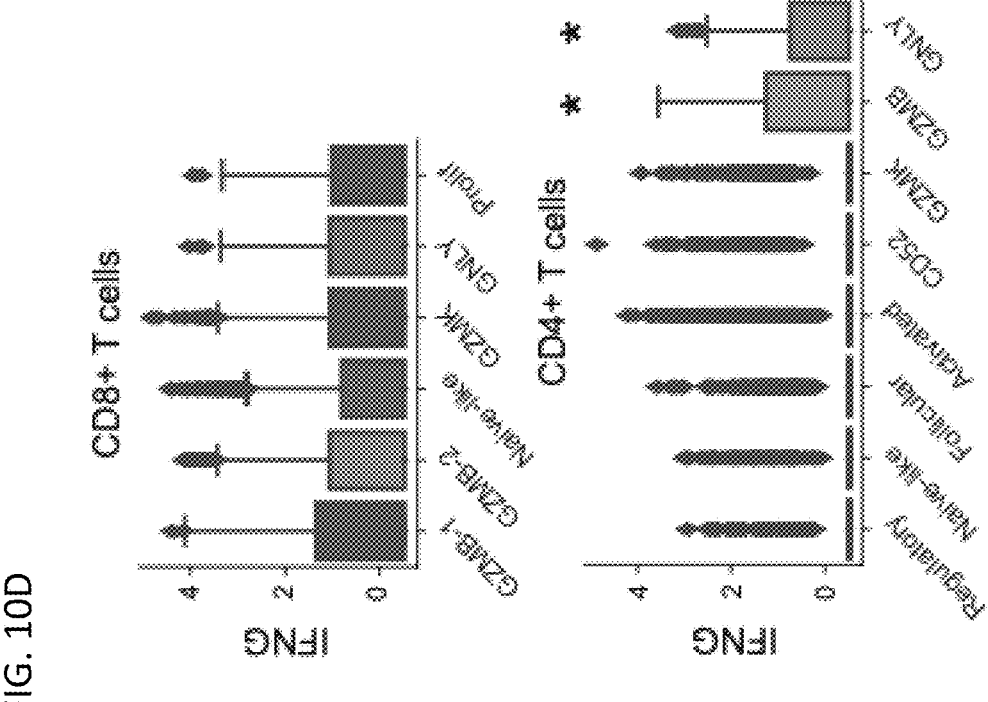

Notably, cytotoxic CD4+ T cells, particularly the CD4GZMB and CD4GNLY cells, expressed IFNG at significantly higher levels than non-cytotoxic CD4+ T cells (p<0.0001, p<0.0001, Mann Whitney U) (FIG. 10D). IFNG has been shown to directly increase HLA class II expression in tumors (for example, see Quezada et al (2010), or Berrih, S. et al. Interferon-gamma modulates HLA class II antigen expression on cultured human thymic epithelial cells. J. Immunol. Baltim. Md. 1950 135, 1165-1171 (1985), the contents of which are incorporated by reference herein in their entirety for any and all purposes). Thus, cytotoxic CD4+ T cells may serve as a reservoir for paracrine induction of HLA class II antigen presentation machinery in tumor cells.

Consistent with other known functions of CD4+ T cells, we identified a T follicular helper cluster, $CD4_{follicular}$, with high IL7R and CD200 expression. Single cell analyses in NSCLC have previously suggested that T follicular helper cells promote cytotoxic T cell proliferation and tissue residence in the tumor microenvironment (for example, see Singh, D. et al. CD4+ follicular helper-like T cells are key players in anti-tumor immunity. bioRxiv 2020.01.08.898346 (2020) doi:10.1101/2020.01.08.898346, the contents of which are incorporated herein by reference in their entirety for any and all purposes). In addition, we also identified a regulatory T cell cluster, $CD4_{regulatory}$, with high FOXP3 expression and an activated T cell cluster, $CD4_{activated}$, characterized by CD69 expression (FIG. 10B).

Cytotoxic T cells are clonally expanded and express elevated levels of immune checkpoint genes: A common trait of antigen experienced T cells is clonal expansion. To assess if the cytotoxic T cell populations identified via single cell RNA expression profiling had evidence of clonal expansion within the tumor microenvironment, we analyzed TCR clonality using scirpy (for example, see Sturm, G. et al. Scirpy: a Scanpy extension for analyzing single-cell T-cell receptor-sequencing data. Bioinformatics doi:10.1093/bioinformatics/btaa611, the contents of which are incorporated herein by reference in their entirety for any and all purposes). We defined TCR clonality as populations of more than one cell possessing identical TCR alpha and TCR beta CDR3 sequences and found evidence of extensive clonal expansion within all cytotoxic T cell populations.

Figures 11A, 11B:
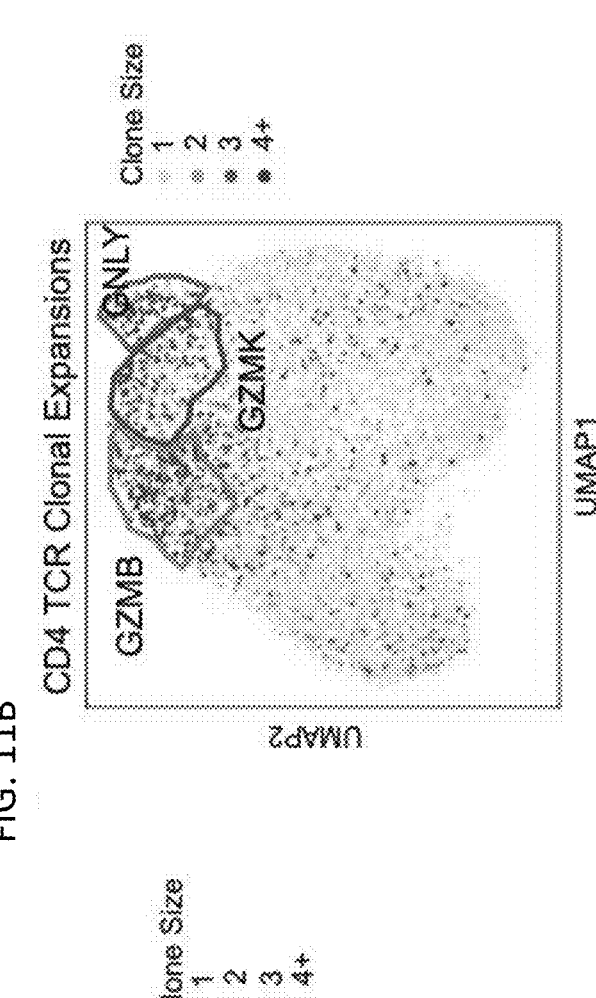
FIG. 11A-D. Cytotoxic CD4+ and CD8+ T cells are clonally expanded in NSCLC. A, UMAP projection showing the clone size associated with the TCR for each cell in CD8+ and B, CD4+ T cells. C, D TCR clonal association between phenotypic states visualized using a graph structure. Each node represents a Leiden cluster and the width of each directed edge represents the percent of clones from the starting node shared with the target node. Edges with weights in the lowest tertile for CD4 and lowest quartile for CD8 are not shown for clarity.
Figures 11C, 11D:
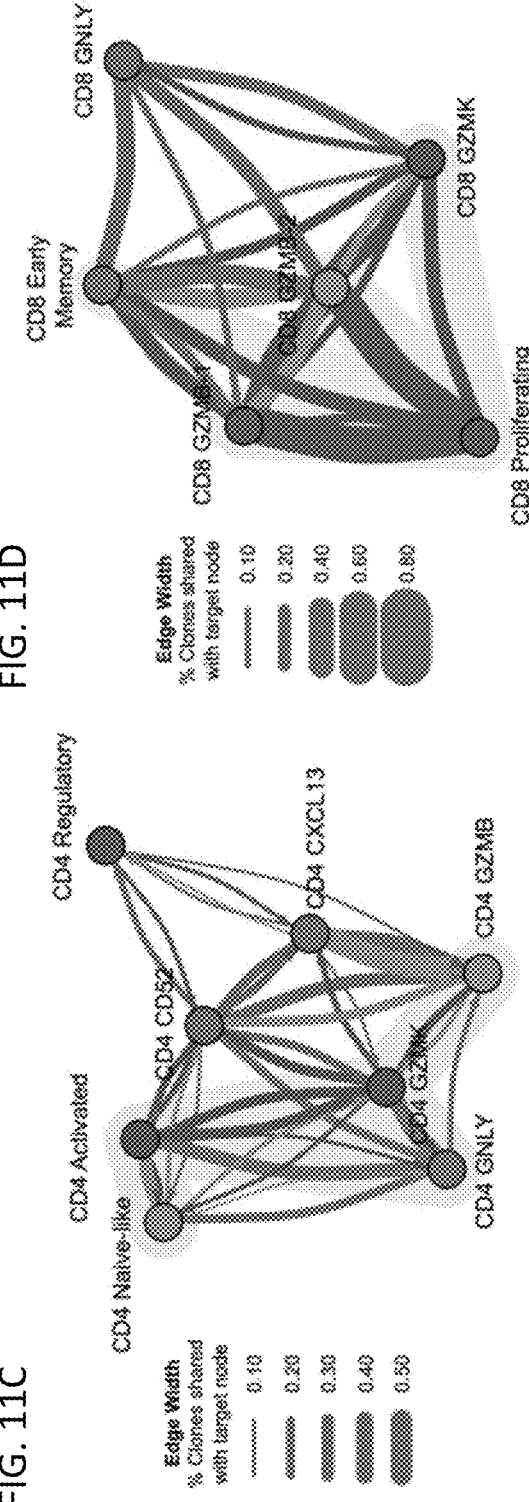
Figures 16A, 16B:
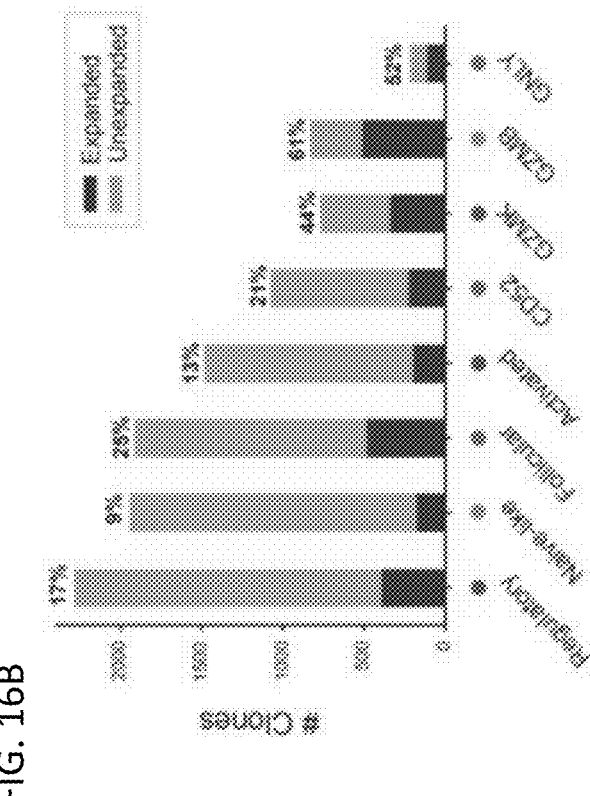
FIG. 16A-B. Clonal expansion in CD4+ and CD8+ T cells. A, B Proportion of clones that are expanded (more than one cell) for each Leiden cluster. The percentage of expanded clones is shown above each bar.

Notably, 83% of all CD8+ cytotoxic cells belonged to an expanded T cell clone. The $CD8_{prolif}$ population contained the greatest proportion of clonally expanded cells, followed by the $CD8_{GZMB-1}$ and $CD8_{GZMB-2}$ clusters (FIGS. 11A, 16A). Overall, 64% of CD8 T cell clones contained cell from more than one Leiden cluster. Of particular note, the $CD8_{prolif}$ clustering had very high degrees of TCR clone sharing with the two $CD8_{GZMB}$ populations, suggesting that these effector cells are being antigen stimulated and actively undergoing clonal expansion (FIG. 11D). A smaller fraction of $CD8_{GZMK}$ and very few $CD8_{GNLY}$ clones were shared with the CD8− proliferating cluster, suggesting that these earlier stage cytotoxic CD8 T cells are less actively proliferating.

Compared to the CD8+ T cells, there were far fewer clonally expanded CD4+ T cells (FIGS. 11B, 16B). However, larger clonal expansions were specifically identified within the cytotoxic CD4+ populations, with 54% of all CD4+ cytotoxic cells belonging to an expanded clone. This suggests that these cells are responding to tumor antigen, similar to cytotoxic CD8+ T cells.

When analyzing prevalence of shared clones across CD4+ T cell sub-populations, we found that 26% of $CD4_{GZMK}$ and 35% of CD4GNLY clones are shared with the $CD4_{activated}$ cells, but only 3% of clones from the $CD4_{GZMB}$ cells are shared with that population (FIG. 11C). This provides further support that $CD4_{GZMK}$ and $CD4_{GNLY}$ cells are earlier stage cytotoxic cells that are differentiated from recently activated CD4 cells.

The CD4GZMB population instead shares some clones with the other cytotoxic populations, but surprisingly, shares over 54% of its clones with the CD4$_{follicular}$ population (FIG. 11C). T follicular helper cells have been suggested to augment cytotoxic CD8 T cell responses in NSCLC32. The shared clonal lineage suggests that the CD4+ T cells that can mediate direct tumor cell killing and those that provision CD8+ T cell help stem from a common precursor.

In sum, this clonal analysis suggests that CD4+ and CD8+ T cells undergo transcriptional changes that likely reflect differentiation into various effector states as they undergo clonal expansion in response to antigen stimulation.

Figures 12A, 12B, 12C:
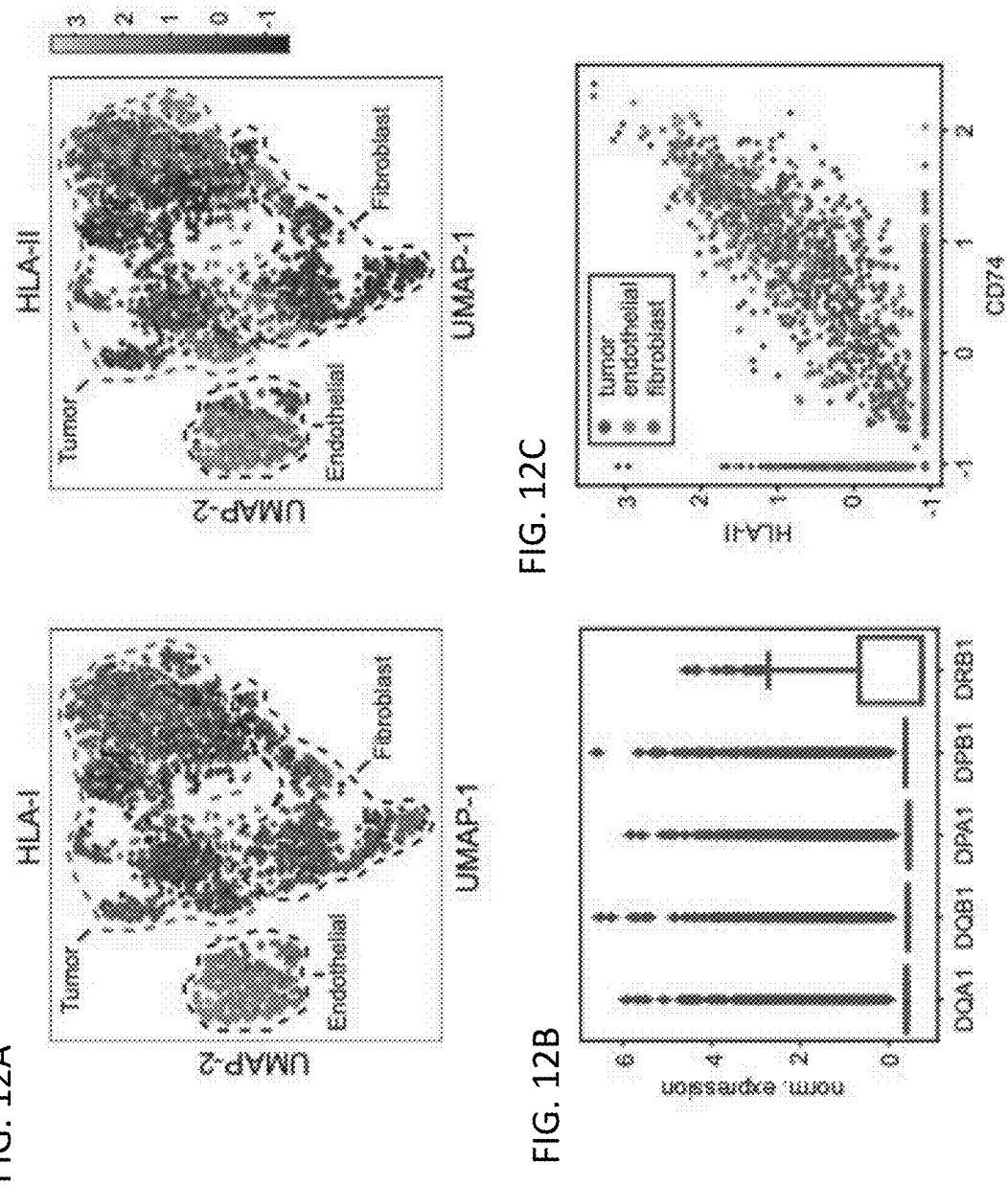
FIG. 12A-D. A subpopulation of tumor cells express HLA class II in NSCLC. UMAP projections showing the expression of A, HLA class I and HLA class II in the CD45– fraction. B, Boxplots show the log transformed expression of the individual HLA class II genes assessed ($p<0.0001$, Kruskal-Wallis). C, Comparison of HLA class II and CD74 (invariant chain) expression ($R=0.627$, $p<0.0001$, Pearson correlation). D, Representative multiplex immunofluorescent staining of CD8 (blue), CD4 (red), GZMB (green), PanCK (magenta), HLA-DR (cyan), and DAPI (grey) of NSCLC tumor. Overlay without DAPI are shown for CD8, CD4 and GZMB, and for PanCK and HLA-DR, along with corresponding H&E. Scale bar, 25 μm.

NSCLC tumor cells express HLA class II: To determine if NSCLC tumor cells have the ability to directly present antigen to cytotoxic CD4+ T cells, we used scHLAcount (for example, see Darby, C. A., Stubbington, M. J. T., Marks, P. J., Martinez Barrio, Á. & Fiddes, I. T. scHLAcount: allele-specific HLA expression from single-cell gene expression data. Bioinformatics 36, 3905-3906 (2020), the contents of which are incorporated herein by reference in their entirety for any and all purposes) to evaluate HLA expression in the CD45− cell fraction. We sequenced 2,152 CD45− cells and identified distinct populations of tumor, endothelial, and fibroblast cells using Leiden clustering and lineage markers. Because HLA class I is expressed by nearly all human cells, the vast majority of cells had detectable levels of HLA class I RNA (FIG. 12A).

HLA class II expression is typically restricted to antigen presenting cells and endothelial cells. However, studies have shown that HLA class II can be expressed on epithelial cells, including in the lung (for example, see Wosen, J. E., Mukhopadhyay, D., Macaubas, C. & Mellins, E. D. Epithelial MHC Class II Expression and Its Role in Antigen Presentation in the Gastrointestinal and Respiratory Tracts. Front. Immunol. 9, (2018), the contents of which are incorporated herein by reference in their entirety for any and all purposes). We found that HLA class II is expressed by a subset of tumor cells and that HLA class II expression is strongly correlated with its chaperone, CD74 (invariant chain) (R=0.627, p0.0001, Pearson correlation) (FIGS. 12A and 12C). Interestingly, HLA class II expression was not uniform across the genes studied, with HLA-DRB1 expressing significantly higher than HLA-DQA1, HLA-DQB1, and HLA-DPB1 (p0.0001, Kruskal-Wallis) (FIG. 12B).

Figure 12D:
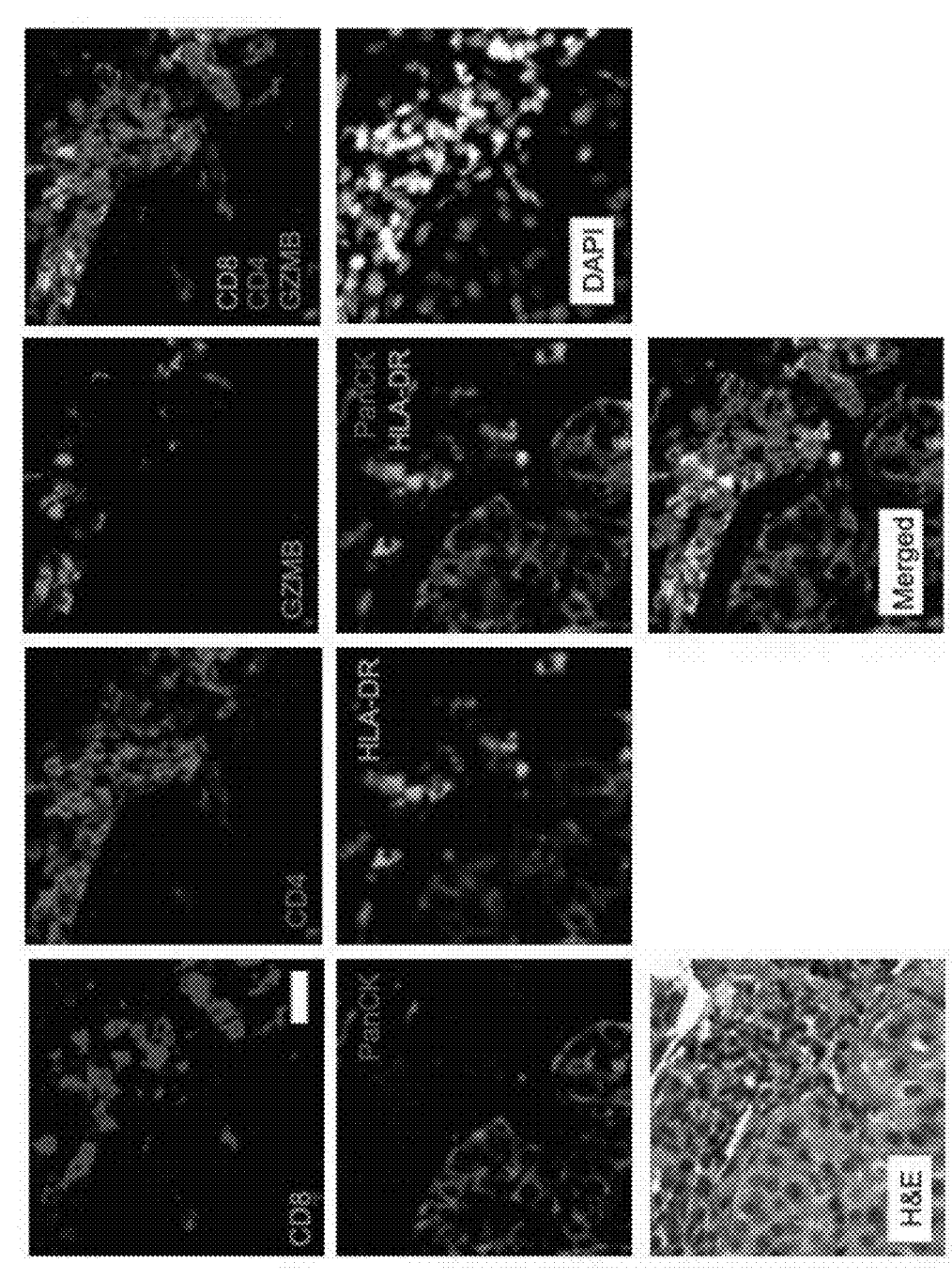

We further investigated the presence of cytotoxic CD4+ T cells and HLA-II expressing tumor cells in NSCLC using immunofluorescence on tumor tissue in a treatment naïve NSCLC sample (FIG. 12D). We tested and optimized a panel of tumor epithelial and lymphocyte specific markers. Pan-cytokeratin staining was utilized to identify epithelial populations within tumor samples and CD4 and CD8 staining was used to highlight tumor infiltrating T cells. We also included HLA-DR to assess HLA-II expression and GZMB to mark cytotoxic lymphocyte populations. Similar to our findings from the single cell profiling data, we found regions within tumor samples where T cells co-expressed CD4 and GZMB and tumor cells co-expressed pan-CK and HLA-DR. These populations were found in some instances to be in close proximity. H&E staining of an adjacent slide revealed nests of malignant cells abutting clusters of lymphocytes, consistent with lymphocytes primed for an anti-tumor immune response.

Figure 13E:
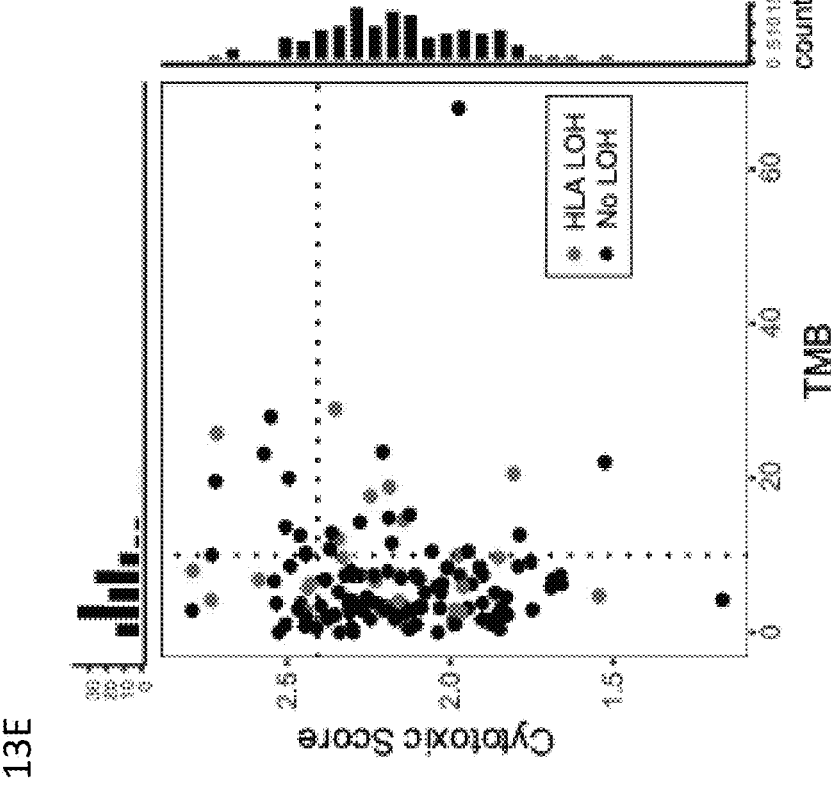

Cytotoxic gene signature predicts immunotherapy response in HLA class I deficient NSCLC patients: To assess the clinical relevance of cytotoxic activity from CD4+ and CD8+ cells, we tested whether a gene signature of cytotoxicity could predict response to checkpoint inhibitors in HLA-I deficient or impaired patients as well as NSCLC patients in general. We created a canonical cytotoxic gene signature score that includes genes that were highly expressed by both CD4+ and CD8+ cytotoxic T cells in our single cell data. In our ICB-treated NSCLC cohort, we found that our cytotoxic score (CS) was significantly associated with TTP (HR=0.45, p=0.004, log rank) (FIG. 13A), but not in a separate NSCLC cohort of patients treated with platinum therapy (HR=1.34, p=0.37, log rank) or the TCGA LUAD cohort that consists of patients primarily treated with platinum therapy (HR=0.98, p=0.91, log rank) (FIG. 13B). Within the ICB-treated HLA-LOH subcohort, CS was also significantly associated with TTP (HR=0.15, p=0.039, log rank), implying that cytotoxic activity from CD4+ T cells can contribute to the checkpoint inhibitor-induced immune response to NSCLC (FIG. 13C).

In the ICB-treated NSCLC cohort, CS was not associated with TMB (R=0.08, p=0.35, Pearson correlation) (FIG. 13D). We combined TMB and CS into a simple multi-modal model (MM) to capture both the immune phenotype of the tumor microenvironment, as well as the immunogenicity of the tumor itself. Patients were labeled as high risk if their tumors were TMB high or CS high. All other patients were labeled as low risk. The MM score was significantly associated with TTP (HR=2.28, p=0.0048, log rank) in the Tempus NSCLC IO cohort but not in a separate Tempus NSCLC cohort of patients treated with platinum therapy (HR=1.27, p=0.85, log rank). This suggests that the association between the MM score to improved TTP is specific to ICB.

These findings show that detecting cytotoxic cells in NSCLC patients, including those with HLA class I deficiencies, can predict ICB outcomes, particularly when combined with TMB.

Discussion: ICB therapy is now used in the majority of metastatic NSCLC patients as the standard of care and has significantly improved the prognosis of these patients. However, the mechanisms underlying ICB response remains incompletely understood. While the classical CD8+ T cell driven tumor killing has been deeply characterized, the contribution of HLA class I independent mechanisms to tumor cell killing in NSCLC remains poorly explored. A better understanding of the role of the cytotoxic capabilities of other immune cell populations, like CD4+ T cells, will facilitate the development of the next generation of CPI (ICB) drugs and improve biomarkers for existing CPI regimens.

In this study, we characterized the tumor infiltrating CD4+ T cell compartment in 10 NSCLC tumors to assess the potential for an HLA class I independent mechanism for tumor killing. We identified a CD4+ T cell population that expresses a canonical cytotoxic program similar to classical CD8+ T cells. Cytotoxic CD4+ T cells in cancer have primarily been characterized in pre-clinical models though recent studies have identified them in patients in multiple cancer types (for example, see Xie et al (2010) or Quezada et al (2010)). However, the presence, functional importance and clinical implications of these cells in NSCLC remained largely unknown. Here, we show that cytotoxic CD4+ T cells are a notable component of the tumor infiltrating immune population in NSCLC. Additionally, we demonstrated these cytotoxic CD4+ T cells are clonally expanded, suggesting they are specific for tumor antigen and express IFNG, which can upregulate HLA class II expression on NSCLC cells. Finally, we show that HLA class II is expressed in a sub-population of NSCLC cells, allowing for direct engagement with CD4+ T cells. We propose that cytotoxic CD4+ T cells can recognize tumor antigen presented by NSCLC cells and directly kill them. As these cells upregulate PDCD1, CTLA4, and TIGIT, they are also likely to be responsive to current ICB therapies. Given the evidence of cytotoxic CD4+ T cells in other solid tumors, we suggest that cytotoxic CD4+ T cells are a fundamental component of the anti-tumor immune response across cancer types.

We also assessed the association of cytotoxicity with ICB response in a real-world cohort of NSCLC patients. We developed a gene signature for cytotoxicity that captures the activity of both CD4+ and CD8+ cytotoxic T cells. Previous studies in other cancer types have shown that cytotoxic gene signatures can be a ICB biomarker (for example, see Cristescu, R. et al. Pan-tumor genomic biomarkers for PD-1 checkpoint blockade-based immunotherapy. Science 362, (2018); Ayers, M. et al. IFN-γ-related mRNA profile predicts clinical response to PD-1 blockade. J. Clin. Invest. 127, 2930-2940 (2017); Rooney, M. S., Shukla, S. A., Wu, C. J., Getz, G. & Hacohen, N. Molecular and Genetic Properties of Tumors Associated with Local Immune Cytolytic Activity. Cell 160, 48-61 (2015); Jiang, P. et al. Signatures of T cell dysfunction and exclusion predict cancer immunotherapy response. Nat. Med. 24, 1550-1558 (2018); or Prat, A. et al. Immune-Related Gene Expression Profiling After PD-1 Blockade in Non-Small Cell Lung Carcinoma, Head and Neck Squamous Cell Carcinoma, and Melanoma. Cancer Res. 77, 3540-3550 (2017) the contents of each of which are incorporated herein by reference in their entirety for any and all purposes), but the predictive ability of these metrics has not been thoroughly explored in NSCLC. One small study with a cohort of 38 patients found that a cytotoxic gene signature was associated with ICB response in NSCLC, but the gene list was not reported (for example, see Damotte, D. et al. The tumor inflammation signature (TIS) is associated with anti-PD-1 treatment benefit in the CERTIM pan-cancer cohort. J. Transl. Med. 17, 357 (2019), the contents of which are incorporated herein by reference in their entirety for any and all purposes). To our knowledge, this is the first comprehensive assessment of a cytotoxic gene signature in a well powered ICB treated NSCLC cohort. We show that patients with higher expression of our cytotoxic score had significantly longer time to progression on ICB compared to those who had lower expression, regardless of HLA class I antigen presentation ability. This metric was also independent of tumor mutational burden and had greater predictive power than PDL1 IHC status. These observations show that an RNA profile of cytotoxicity can be an effective biomarker for identifying NSCLC patients who are more likely to respond to ICB and remains robust even in populations with high levels of HLA loss of heterozygosity or other antigen presentation associated resistance mechanisms.

Overall, this work highlights the importance of the cytotoxic CD4+ T cell compartment in the anti-tumor response and identifies a novel genomic biomarker for ICB response in NSCLC. This study advances our understanding on class I independent mechanisms for tumor cell killing and lays the groundwork for improved biomarker identification and future ICB drug discovery and development.

Methods

NSCLC IO and Platinum Cohort and Clinical Endpoints

Patients were selected from a de-identified Real-World Evidence (RWE) database. For inclusion in this study, patients were required to 1) have a diagnosis of metastatic NSCLC with a non-squamous histology, 2) have received an FDA approved checkpoint inhibitor regimen for the IO (ICB) cohort or an FDA approved platinum chemotherapy regimen for the platinum cohort, 3) have a documented progression event after treatment initiation or have at least 90 days of follow up from treatment initiation, 4) completed next generation DNA and RNA sequencing on a checkpoint inhibitor or platinum naïve biopsy and 5) have no actionable driver mutations (for example, no EGFR or ALK variants/alterations). The primary clinical endpoint was real world time to progression (rwTTP), defined as the time from the initiation of the checkpoint inhibitor regimen to the first progression event, censored on the last known clinical encounter. Patients who ended treatment due to an adverse event, non-compliance, or other non-progression related reason were censored at the time of treatment stop.

Clinical Data Abstraction

Clinical features for this study were derived from unstructured physician progress notes. The physician notes were abstracted using a standardized enriched curation process. A data dictionary and template were developed with the advice of a panel of oncologists. The data dictionary includes every field, the associated value sets, the definition of the fields, and scenarios to clarify for abstraction. Each patient case was curated by at least two abstractors and any discordance was reviewed by a third abstractor and if needed, a lung oncologist.

DNA and RNA Sequencing

Formalin-fixed, paraffin embedded patient samples were profiled using targeted panel (596, 624, or 1700 genes) or whole exome DNA sequencing, as well as whole transcriptome RNA sequencing. DNA and RNA sequencing was performed as previously described (for example, see Beaubier et al (2018) and Beaubier et al (2019)).

Tumor Mutational Burden

TMB was calculated by dividing the number of non-synonymous mutations by the megabase size of the panel. All non-silent somatic coding mutations, including missense, indel and stop-loss variants with coverage greater than 100× and an allelic fraction greater than 5% for targeted gene panels and coverage greater than 30× and an allelic fraction greater than 10% for whole exome, were counted as non-synonymous mutations.

HLA Loss of Heterozygosity

We assessed HLA LOH status for all patients with a matched normal sample. Four digit class I HLA typing was performed on the matched normal samples using Optitype (for example, see Szolek, A. et al. OptiType: precision HLA typing from next-generation sequencing data. Bioinformatics 30, 3310-3316 (2014), the contents of which are incorporated herein by reference in their entirety for any and all purposes) and custom HLA reference file for each patient was generated. All HLA mapping reads, as well as unmapped reads were extracted from the tumor and normal BAM files and remapped to the patient's HLA reference. After accounting for potential germline variants present in the sample's HLA, the alignments were updated and allele specific coverage was determined. Changes in coverage between alleles, in the context of the expected tumor purity, were assessed to determine if any reduction in allele coverage was consistent with a clonal loss of a specific HLA allele.

Transcriptomic Analysis

Transcript-level quantification to GRCh37 was performed using Kallisto 0.44. Transcript counts were then corrected for GC content and length using quantile normalization and adjusted for sequencing depth via a size factor method. Normalized counts in protein coding transcripts covered by the exome panel were then summed to obtain gene-level counts. Subsequent expression analyses were performed on log 10-transformed counts.

PDL1 status

PDL1 status imputed from CD274 expression using a model trained on an independent cohort of solid tumor samples with matched IHC and whole transcriptome data. Tumors are considered PDL1 positive if they are predicted to be >=1% tumor cell PDL1 staining. (for example, see U.S. patent application Ser. No. 16/888,357 filed May 29, 2020, the contents of which are incorporated by reference herein in their entirety for any and all purposes)

Single Cell Multiomic Sequencing

Samples for single cell multiomic sequencing were previously frozen dissociated tumor cells (DTCs) (Discovery Life Sciences, Huntsville, AL). DTCs were thawed and washed with FACS buffer (PBS, 0.04% BSA). The cells were first incubated with Human TruStain FcX™ (Fc Receptor Blocking Solution (Cat #422301, BioLegend) and then stained with FITC-conjugated anti-Human-CD45 antibody (Cat #304006, BioLegend), and DAPI for flow cytometry, along with a cocktail of 30 TotalSeq antibodies specific to immunology surface markers (BioLegend, San Diego, CA) for 30 minutes at 40 C and washed twice with FACS buffer.

Samples were sorted using SH800S cells sorter (Sony Biotechnology). Live cells were gated on DAPI– cells, sorted as CD45+ and CD45– populations and collected in RPMI. The sorted CD45+ and CD45– cells were pelleted and resuspended to recover a target of 3000 cells after 10× droplet formation. Cellular suspensions were barcoded using a Chromium Single Cell Controller instrument (10× Genomics) and 10× Genomics Chromium Single Cell A Chip Kit (P/N 120236, 10× Genomics) to generate single-cell Gel Beads-in-Emulsion (GEMs) for reverse transcription. Single-cell RNA-Seq libraries may be prepared using the Chromium Single Cell 5' Library and Gel Bead Kit (P/N 1000020, 10× Genomics) as per manufacturer's instructions. For each tumor sample, four libraries were generated: CD45– 5' gene expression library, CD45+ 5' gene expression library, CD45+ TCR library, and CD45+ cell surface protein library.

Single Cell Multiomic Analysis

Raw sequencing files were processed through the Cell-Ranger pipeline (version 3.1.0) and then analyzed using scanpy (version 1.6) (for example, see Wolf, F. A., Angerer, P. & Theis, F. J. SCANPY: large-scale single-cell gene expression data analysis. Genome Biol. 19, 15 (2018), the contents of which are incorporated herein by reference in their entirety for any and all purposes) and scirpy (version 0.4) (for example, see Sturm et al doi:10.1093/bioinformatics/btaa611). Cells with detectable gene expression in less than 200 genes, greater than 6% mitochondrial genes for immune cells, greater than 20% mitochondrial genes for tumor cells or more than 2500 genes were removed from downstream analyses, as were any genes expressed in less than 3 cells. Scrublet (for example, see Wolock, S. L., Lopez, R. & Klein, A. M. Scrublet: Computational Identification of Cell Doublets in Single-Cell Transcriptomic Data. Cell Syst. 8, 281-291.e9 (2019), the contents of which are incorporated herein by reference in their entirety for any and all purposes) was used for doublet detection and removal. Gene expression values were normalized to 10,000 counts per cell and log transformed. Protein expression values were normalized using the centered log-ratio normalization.

Data from the CD45+ fraction was then filtered on the CD4+ T cell population, based on protein expression of CD45, CD3, CD4, CD8 and CD20 and RNA expression of CD68. Data from CD45-fraction was filtered to remove a minor population of contaminating immune cells. Genes from the T cell receptor and HLA loci were removed from the gene expression data. The gene expression data was then batch corrected using BBKNN (for example, see BBKNN: fast batch alignment of single cell transcriptomes|Bioinformatics|Oxford Academic, the contents of which are incorporated herein by reference in their entirety for any and all purposes), filtered on highly variable genes, and scaled to unit variance. Leiden clustering was performed using Scanpy with a resolution of 0.7 for the CD8 cells and 0.8 for the CD4 cells. Cell cycle status was assessed using the score_genes_cell_cycle function in Scanpy with the gene list from Tirosh, et al (for example, see Tirosh, I. et al. Dissecting the multicellular ecosystem of metastatic melanoma by single-cell RNA-seq. Science 352, 189-196 (2016), the contents of which are incorporated herein by reference in their entirety for any and all purposes).

To assess HLA expression, we first performed HLA typing using ArcasHLA (for example, see Orenbuch, R. et al. arcasHLA: high-resolution HLA typing from RNAseq. Bioinformatics 36, 33-40 (2020), the contents of which are incorporated by reference in their entirety for any and all purposes) and then quantified HLA expression using scHLAcount (for example, see Darby et al (2020)). Gene level raw counts were then normalized by library size and log transformed.

For the T cell receptor analysis, the most abundant TRA and TRB chains for each barcode were used for analysis. Cells without a paired TRA and TRB were removed. A TCR clonotype was defined as a group of cells with identical TRA and TRB CDR3 sequences. An expanded clone is any clone consisting of more than one cell.

Immunofluorescence Staining

Multiplex immunofluorescence staining was performed on FFPE sections as previously described (for example, see Durante, M. A. et al. Single-cell analysis reveals new evolutionary complexity in uveal melanoma. Nat. Commun. 11, 1-10 (2020), the contents of which are incorporated herein by reference in their entirety for any and all purposes). In brief, slides were deparaffinized and re-hydrated, followed by antigen retrieval. Slides were first stained with a cocktail of primary antibodies against CD4, CD8, GZMB, pan-cytokeratin, and HLA-DR diluted with antibody diluent (PBS/1% BSA/0.2% Tween 20/15 mM) for 1 h (UltraPlex detection system, Cell IDx). Slides were then washed with wash buffer and a cocktail of detection antibodies (UltraPlex detection system, Cell IDx) diluted with antibody diluent (PBS/1% BSA/0.2% Tween 20) was added to the slide and incubated for 1 hour. As a negative control, slides were incubated with the secondary detection cocktail alone. Slides were then mounted using Fluoroshield with DAPI (Immunobiosciences) and coverslips applied prior to scanning at 20× using the Leica Versa scanner. Analysis was performed on the Aperio ImageScope, (v12.4.2.5010), using Leica Quantitative Algorithm (v1).

Cytotoxic Score

The cytotoxic score is calculated by taking the arithmetic mean of 21 genes that are highly expressed in both CD4 and CD8 cytotoxic T cells. The genes are NKG7, CCL5, GZMA, CCL4, CST7, GZMH, GZMB, GZMK, PRF1, GNLY, CCL4L2, CD74, IL32, CD52, CCL3, LAG3, CTSW, DUSP4, CTSC, ABI3, S100A4.

Survival Analysis

Kaplan-Meier plots were generated using the survminer R package. The log-rank test was used to compare survival curves and hazard ratios were calculated using a Cox proportional hazards model.

Model Training

Figure 21:
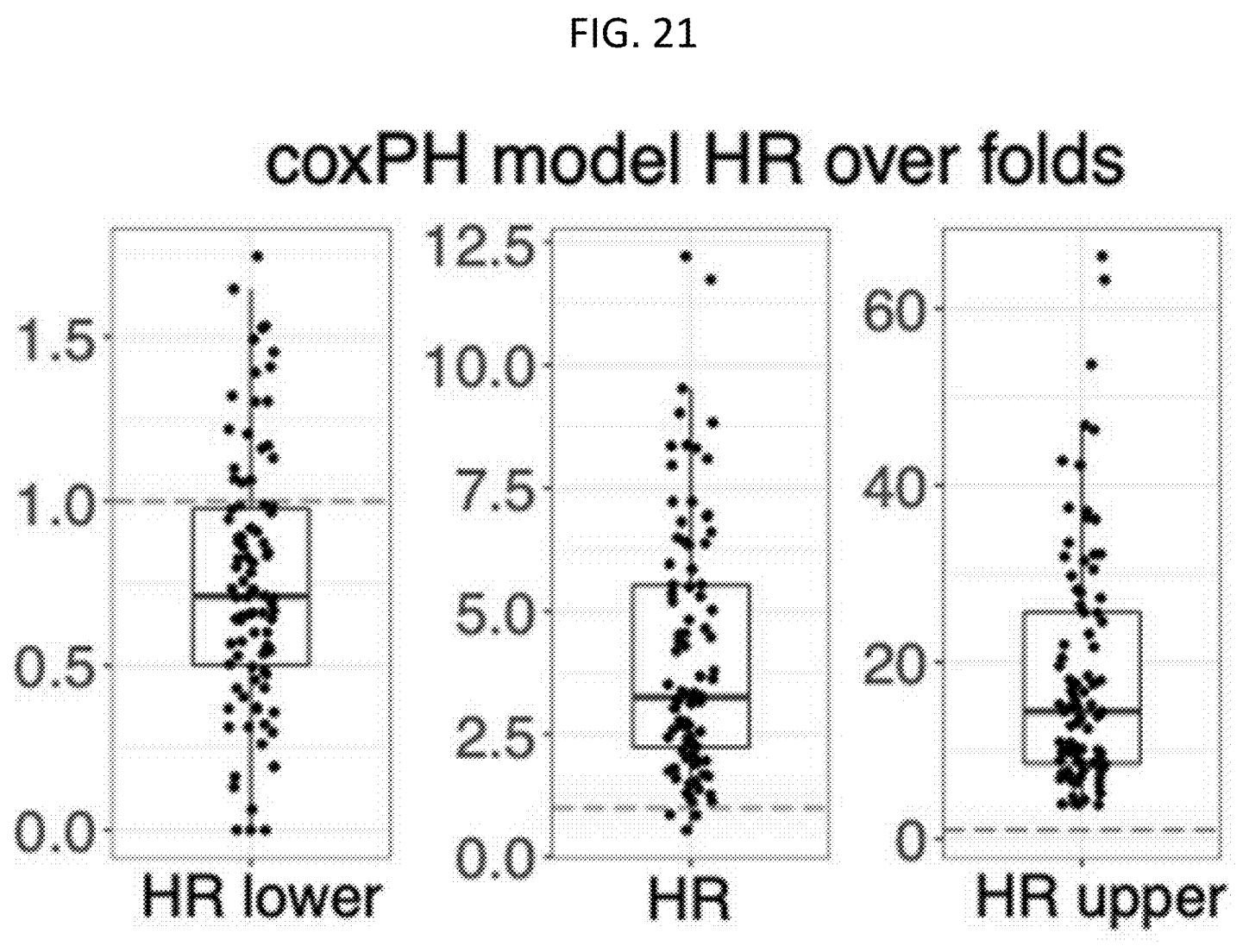
Figure 22:
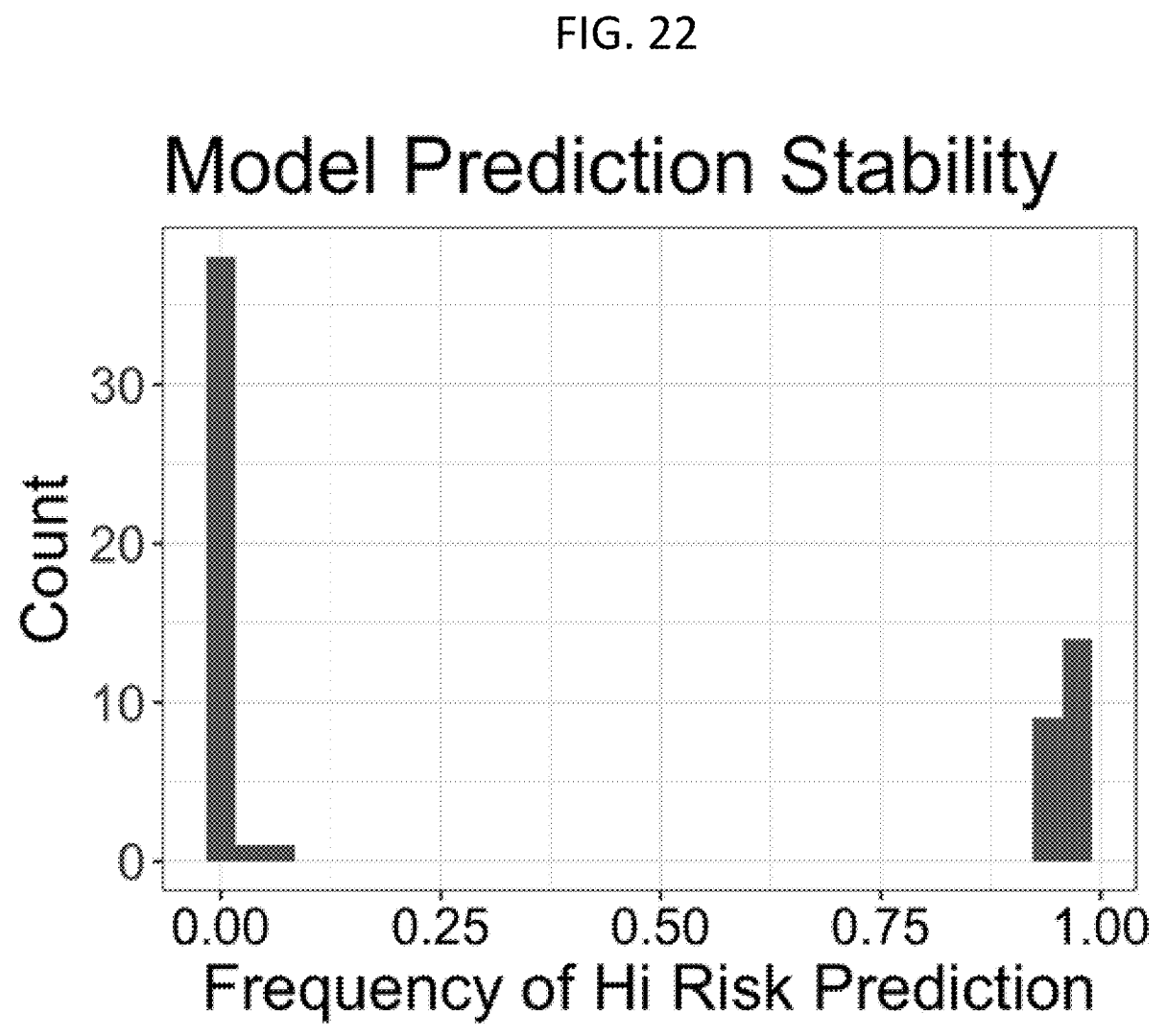

Patients in the NSCLC IO cohort were randomly split into train and test cohorts 100 times, with 75% of patients in train and 25% of patients in test for each shuffle. A multivariate Cox proportional hazards model to predict TTP was trained and evaluated for each shuffle using the scikit-survival package (for example, see Polsterl, S. scikit-survival: A Library for Time-to-Event Analysis Built on Top of scikit-learn. J. Mach. Learn. Res. 21, 1-6 (2020), the contents of which are incorporated herein by reference in their entirety for any and all purposes). A binary TMB score using 10 mutations/MB as a threshold and a scaled version of the cytotoxic score were the input features. Each patient was first scored using the mean risk score from folds where they were in the test cohort. Patients were then classified into high and low risk categories based on whether their risk score was greater than the baseline hazard of the cohort. FIG. 20 shows results after assessing a coxPH model using binarized TMB and continuous CYT score against potential clinical confounders. FIG. 21 illustrates the stability of the model performance over multiple shuffles of data (different folds of data). Test set size in each fold is on average 16. In this example, the small sample size leads to the large confidence intervals for the HR. FIG. 22 illustrates the stability of the model prediction over multiple shuffles of data (different folds of data). The majority of patients were labeled consistently as high or low risk across shuffles. See also, Tables 6-8 summarizing the above findings.

Table 6 shows the patient classification, hazard ratio, 95% confidence interval, and p-value for the coxpH model as described above.

TABLE 6

| coxPH Tests | HR | 95% CI | p-value |
|---|---|---|---|
| Surv~hi risk | 3.089 | (1.54-6.22) | 0.0016 |
| Surv~hi risk + io_monotherapy | 3.578 | (1.64-7.79) | 0.0013 |
| Surv~hi risk + strata(io_monotherapy) | 3.576 | (1.61-7.896) | 0.0016 |
| Surv~TMB High | 0.29 | (0.10-0.82) | 0.02 |
| Surv~Cyt score | 0.46 | (0.14-1.52) | 0.2 |

Table 7 shows the model performance at various time points.

TABLE 7

| Days | Group | Non-progression probability (CI) | diff in probability |
|---|---|---|---|
| 90 | High Risk | 0.65 (0.548-0.88) | 0.25 |
| | Low Risk | 0.90 (0.81-1.00) | |
| 180 | High Risk | 0.34 (0.19-0.63) | 0.38 |
| | Low Risk | 0.72 (0.58-0.88) | |
| 360 | High Risk | 0.15 (0.05-0.49) | 0.36 |
| | Low Risk | 0.51 (0.37-0.72) | |

Table 8 shows the model performance at various time points.

TABLE 8

| Days | Sensitivity mean (median) | Specificity mean (median) | AUC mean (median) |
|---|---|---|---|
| 90 | 0.64 (0.67) | 0.72 (0.73) | 0.68 (0.70) |
| 180 | 0.57 (0.56) | 0.81 (0.8) | 0.70 (0.69) |
| 380 | 0.52 (0.5) | 0.87 (1) | 0.72 (0.73) |

In various embodiments, model performance may be assessed for each sub-group of patients. For example, patients having a PD-L1 negative status, PD-L1 positive status, PD-L1 high status, primary cancer biopsy, metastatic cancer biopsy, biopsy from a specified tissue site, adenocarcinoma, adenosquamous carcinoma, non-adenocarcinoma non-squamous carcinoma cell carcinoma, follow-up clinical data for a specified period of time after the start of IO therapy (for example, 3 months, 6 months, 12 months, etc), patients who received IO as first line of therapy, patients who received IO as a second or later line of therapy, who received first line platinum chemotherapy treatment, who received IO monotherapy, who received IO combination therapy, or any other clinical or molecular characteristic.

REFERENCES

1) Quezada, S. A. et al. Tumor-reactive CD4+ T cells develop cytotoxic activity and eradicate large established melanoma after transfer into lymphopenic hosts. J Exp Med 207, 637-650 (2010).

2) Xie, Y. et al. Naive tumor-specific CD4(+) T cells differentiated in vivo eradicate established melanoma. J Exp Med 207, 651-667 (2010).

3) Oh, D. Y. et al. Intratumoral CD4+ T Cells Mediate Anti-tumor Cytotoxicity in Human Bladder Cancer. Cell 181, 1612-1625.e13 (2020).

4) McGranahan, N. et al. Allele-Specific HLA Loss and Immune Escape in Lung Cancer Evolution. Cell 171, 1259-1271.e11 (2017).

5) Chowell, D. et al. Patient HLA class I genotype influences cancer response to checkpoint blockade immunotherapy. Science 359, 582-587 (2018).

6) Guo, X. et al. Global characterization of T cells in non-small-cell lung cancer by single-cell sequencing. Nature Medicine 24, 978-985 (2018).

7) Zhang, L. et al. Lineage tracking reveals dynamic relationships of T cells in colorectal cancer. Nature 564, 268-272 (2018).

8) Zheng, C. et al. Landscape of Infiltrating T Cells in Liver Cancer Revealed by Single-Cell Sequencing. Cell 169, 1342-1356.e16 (2017).

9) Wolock, S. L., Lopez, R. & Klein, A. M. Scrublet: Computational Identification of Cell Doublets in Single-Cell Transcriptomic Data. Cell Systems 8, 281-291.e9 (2019).

10) BBKNN: fast batch alignment of single cell transcriptomes Bioinformatics Oxford Academic. academic.oup-.com/bioinformatics/article/36/3/964/5545955.

11) Voskoboinik, I., Whisstock, J. C. & Trapani, J. A. Perforin and granzymes: function, dysfunction and human pathology. Nature Reviews Immunology 15, 388-400 (2015).

12) Axelrod, M. L., Cook, R. S., Johnson, D. B. & Balko, J. M. Biological Consequences of MHC-II Expression by Tumor Cells in Cancer. Clin Cancer Res 25, 2392-2402 (2019).

13) Castro, A. et al. Elevated neoantigen levels in tumors with somatic mutations in the HLA-A, HLA-B, HLA-C and B2M genes. *BMC Med Genomics* 12, (2019).

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. Patent Publication No. 2021/0090694, titled "Data Based Cancer Research and Treatment Systems and Methods", and published Mar. 25, 2021, which is incorporated herein by reference and in its entirety for any and all purposes.

For example, an implementation of one or more embodiments of the methods and systems as described above may include microservices constituting a digital and laboratory health care platform supporting IO progression risk prediction. Embodiments may include a single microservice for executing and delivering a determination of a patient's likelihood of progressing during IO therapy or may include a plurality of microservices each having a particular role which together implement one or more of the embodiments above. In one example, a first microservice may execute a CYT score determination in order to deliver a CS to a second microservice for comparing the CS to a threshold. Similarly, the second microservice may execute comparing the CS to a threshold to deliver a determination of a patient's likelihood of progressing during IO therapy according to an embodiment, above.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Patent Publication No. 2020/80365232, titled "Adaptive Order Fulfillment and Tracking Methods and Systems", and published Nov. 19, 2020, which is incorporated herein by reference and in its entirety for all purposes.

For example, continuing with the above first and second microservices, an order management system may notify the first microservice that an order for CS determination has been received and is ready for processing. The first microservice may execute and notify the order management system once the delivery of CS is ready for the second microservice. Furthermore, the order management system may identify that execution parameters (prerequisites) for the second microservice are satisfied, including that the first microservice has completed, and notify the second microservice that it may continue processing the order to compare the CS to a threshold according to an embodiment, above.

Where the digital and laboratory health care platform further includes a genetic analyzer system, the genetic analyzer system may include targeted panels and/or sequencing probes. An example of a targeted panel for sequencing cell-free (cf) DNA and determining various characteristics of a specimen based on the sequencing is disclosed, for example, in U.S. patent application Ser. No. 17/179,086, titled "Methods And Systems For Dynamic Variant Thresholding In A Liquid Biopsy Assay", and filed Feb. 18, 1921, U.S. patent application Ser. No. 17/179,267, titled "Estimation Of Circulating Tumor Fraction Using Off-Target Reads Of Targeted-Panel Sequencing", and filed Feb. 18, 1921, and U.S. patent application Ser. No. 17/179, 279, titled "Methods And Systems For Refining Copy Number Variation In A Liquid Biopsy Assay", and filed Feb. 18, 1921 which is incorporated herein by reference and in its entirety for all purposes. In one example, targeted panels may enable the delivery of next generation sequencing results (including sequencing of DNA and/or RNA from solid or cell-free specimens) for IO progression risk prediction according to an embodiment, above. An example of the design of next-generation sequencing probes is disclosed, for example, in U.S. Patent Publication No. 2021/0115511, titled "Systems and Methods for Next Generation Sequencing Uniform Probe Design", and published Jun. 22, 2021 and U.S. patent application Ser. No. 17/323,986, titled "Systems and Methods for Next Generation Sequencing Uniform Probe Design", and filed May 18, 1921, which are incorporated herein by reference and in their entirety for all purposes.

Where the digital and laboratory health care platform further includes an epigenetic analyzer system, the epigenetic analyzer system may analyze specimens to determine their epigenetic characteristics and may further use that information for monitoring a patient over time. An example of an epigenetic analyzer system is disclosed, for example, in U.S. patent application Ser. No. 17/352,231, titled "Molecular Response And Progression Detection From Circulating Cell Free DNA", and filed Jun. 18, 1921, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce IO progression risk prediction as a result.

When the digital and laboratory health care platform further includes an RNA data normalizer, any RNA read counts may be normalized before processing embodiments as described above. An example of an RNA data normalizer is disclosed, for example, in U.S. Patent Publication No. 2020/0098448, titled "Methods of Normalizing and Correcting RNA Expression Data", and published Mar. 26, 2020, which is incorporated herein by reference and in its entirety for all purposes.

When the digital and laboratory health care platform further includes a genetic data deconvolver, any system and method for deconvolving may be utilized for analyzing genetic data associated with a specimen having two or more biological components to determine the contribution of each component to the genetic data and/or determine what genetic data would be associated with any component of the specimen if it were purified. An example of a genetic data deconvolver is disclosed, for example, in U.S. Patent Publication No. 2020/0210852, published Jul. 2, 2020, and PCT/US19/69161, filed Dec. 31, 2019, both titled "Transcriptome Deconvolution of Metastatic Tissue Samples"; and U.S. patent application Ser. No. 17/074,984, titled "Calculating Cell-type RNA Profiles for Diagnosis and Treatment", and filed Oct. 20, 2020, the contents of each of which are incorporated herein by reference and in their entirety for all purposes.

RNA expression levels may be adjusted to be expressed as a value relative to a reference expression level. Furthermore, multiple RNA expression data sets may be adjusted, prepared, and/or combined for analysis and may be adjusted to avoid artifacts caused when the data sets have differences because they have not been generated by using the same methods, equipment, and/or reagents. An example of RNA data set adjustment, preparation, and/or combination is disclosed, for example, in U.S. patent application Ser. No. 17/405,025, titled "Systems and Methods for Homogenization of Disparate Datasets", and filed Aug. 18, 2021.

When the digital and laboratory health care platform further includes an automated RNA expression caller, RNA expression levels associated with multiple samples may be compared to determine whether an artifact is causing anomalies in the data. An example of an automated RNA expression caller is disclosed, for example, in U.S. Pat. No. 11,043,283, titled "Systems and Methods for Automating RNA Expression Calls in a Cancer Prediction Pipeline", and issued Jun. 22, 2021, which is incorporated herein by reference and in its entirety for all purposes.

The digital and laboratory health care platform may further include one or more insight engines to deliver information, characteristics, or determinations related to a disease state that may be based on genetic and/or clinical data associated with a patient, specimen and/or organoid. Exemplary insight engines may include a tumor of unknown origin (tumor origin) engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, a T cell receptor or B cell receptor profiling engine, a line of therapy engine, a metastatic prediction engine, and so forth.

An example tumor origin or tumor of unknown origin engine is disclosed, for example, in U.S. patent application Ser. No. 15/930,234, titled "Systems and Methods for Multi-Label Cancer Classification", and filed May 12, 1920, which is incorporated herein by reference and in its entirety for all purposes.

An example of an HLA LOH engine is disclosed, for example, in U.S. Pat. No. 11,081,210, titled "Detection of Human Leukocyte Antigen Class I Loss of Heterozygosity in Solid Tumor Types by NGS DNA Sequencing", and issued Aug. 3, 2021, which is incorporated herein by reference and in its entirety for all purposes.

An example of a tumor mutational burden (TMB) engine is disclosed, for example, in U.S. Patent Publication No. 2020/0258601, titled "Targeted-Panel Tumor Mutational Burden Calculation Systems and Methods", and published Aug. 13, 2020, which is incorporated herein by reference and in its entirety for all purposes.

An example of a PD-L1 status engine is disclosed, for example, in U.S. Patent Publication No. 2020/0395097, titled "A Pan-Cancer Model to Predict The PD-L1 Status of a Cancer Cell Sample Using RNA Expression Data and Other Patient Data", and published Dec. 17, 2020, which is incorporated herein by reference and in its entirety for all purposes. An additional example of a PD-L1 status engine is disclosed, for example, in U.S. Pat. No. 10,957,041, titled "Determining Biomarkers from Histopathology Slide Images", issued Mar. 23, 2021, which is incorporated herein by reference and in its entirety for all purposes.

An example of a homologous recombination deficiency engine is disclosed, for example, in U.S. Pat. No. 10,975,445 and PCT/US20/18002, both titled "An Integrative Machine-Learning Framework to Predict Homologous Recombination Deficiency", and filed Feb. 12, 1920, which is incorporated herein by reference and in its entirety for all purposes.

An example of a cellular pathway activation report engine is disclosed, for example, in U.S. Patent Publication No. 2021/0057042, titled "Systems And Methods For Detecting Cellular Pathway Dysregulation In Cancer Specimens", and published Feb. 25, 2021, which is incorporated herein by reference and in its entirety for all purposes.

An example of an immune infiltration engine is disclosed, for example, in U.S. Patent Publication No. 2020/0075169, titled "A Multi-Modal Approach to Predicting Immune Infiltration Based on Integrated RNA Expression and Imaging Features", and published Mar. 5, 2020, which is incorporated herein by reference and in its entirety for all purposes.

An example of an MSI engine is disclosed, for example, in U.S. Patent Publication No. 2020/0118644, titled "Microsatellite Instability Determination System and Related Methods", and published Apr. 16, 2020, which is incorporated herein by reference and in its entirety for all purposes. An additional example of an MSI engine is disclosed, for example, in U.S. Patent Publication No. 2021/0098078, titled "Systems and Methods for Detecting Microsatellite Instability of a Cancer Using a Liquid Biopsy", and published Apr. 1, 2021, which is incorporated herein by reference and in its entirety for all purposes.

An example of a pathogen infection status engine is disclosed, for example, in U.S. Pat. No. 11,043,304, titled "Systems And Methods For Using Sequencing Data For Pathogen Detection", and issued Jun. 22, 2021, which is incorporated herein by reference and in its entirety for all purposes. Another example of a pathogen infection status engine is disclosed, for example, in PCT/US21/18619, titled "Systems And Methods For Detecting Viral DNA From Sequencing", and filed Feb. 18, 2021, which is incorporated herein by reference and in its entirety for all purposes.

An example of a T cell receptor or B cell receptor profiling engine is disclosed, for example, in U.S. patent application Ser. No. 17/302,030, titled "TCR/BCR Profiling", and filed Apr. 21, 2021, which is incorporated herein by reference and in its entirety for all purposes.

An example of a line of therapy engine is disclosed, for example, in U.S. Patent Publication No. 2021/0057071, titled "Unsupervised Learning And Prediction Of Lines Of Therapy From High-Dimensional Longitudinal Medications Data", and published Feb. 25, 2021, which is incorporated herein by reference and in its entirety for all purposes.

An example of a metastatic prediction engine is disclosed, for example, in U.S. Pat. No. 11,145,416, titled "Predicting likelihood and site of metastasis from patient records", and issued Oct. 12, 2021, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ.

The report may include therapies and/or clinical trials matched based on a portion or all of the genetic profile or insight engine findings and summaries. For example, the clinical trials may be matched according to the systems and methods disclosed in U.S. Patent Publication No. 2020/0381087, titled "Systems and Methods of Clinical Trial Evaluation", published Dec. 3, 2020, which is incorporated herein by reference and in its entirety for all purposes.

The report may include a comparison of the results (for example, molecular and/or clinical patient data) to a database of results from many specimens. An example of methods and systems for comparing results to a database of results are disclosed in U.S. Patent Publication No. 2020/0135303 titled "User Interface, System, And Method For Cohort Analysis" and published Apr. 30, 2020, and U.S. Patent Publication No. 2020/0211716 titled "A Method and Process for Predicting and Analyzing Patient Cohort Response, Progression and Survival", and published Jul. 2, 2020, which is incorporated herein by reference and in its entirety for all purposes. The information may be used, sometimes in conjunction with similar information from additional specimens and/or clinical response information, to match therapies likely to be successful in treating a patient, discover biomarkers or design a clinical trial.

Any data generated by the systems and methods and/or the digital and laboratory health care platform may be downloaded by the user. In one example, the data may be downloaded as a CSV file comprising clinical and/or molecular data associated with tests, data structuring, and/or other services ordered by the user. In various embodiments, this may be accomplished by aggregating clinical data in a system backend and making it available via a portal. This data may include not only variants and RNA expression data, but also data associated with immunotherapy markers such as MSI and TMB, as well as RNA fusions.

When the digital and laboratory health care platform further includes a device comprising a microphone and speaker for receiving audible queries or instructions from a user and delivering answers or other information, the methods and systems described above may be utilized to add data to a database the device can access. An example of such a device is disclosed, for example, in U.S. Patent Publication No. 2020/0335102, titled "Collaborative Artificial Intelligence Method And System", and published Oct. 22, 2020, which is incorporated herein by reference and in its entirety for all purposes.

When the digital and laboratory health care platform further includes a mobile application for ingesting patient records, including genomic sequencing records and/or results even if they were not generated by the same digital and laboratory health care platform, the methods and systems described above may be utilized to receive ingested patient records. An example of such a mobile application is disclosed, for example, in U.S. Pat. No. 10,395,772, titled "Mobile Supplementation, Extraction, And Analysis Of Health Records", and issued Aug. 27, 2019, which is incorporated herein by reference and in its entirety for all purposes. Another example of such a mobile application is disclosed, for example, in U.S. Pat. No. 10,902,952, titled "Mobile Supplementation, Extraction, And Analysis Of Health Records", and issued Jan. 26, 2021, which is incorporated herein by reference and in its entirety for all purposes. Another example of such a mobile application is disclosed, for example, in U.S. Patent Publication No. 2021/0151192, titled "Mobile Supplementation, Extraction, And Analysis Of Health Records", and filed May 20, 2021, which is incorporated herein by reference and in its entirety for all purposes.

When the digital and laboratory health care platform further includes organoids developed in connection with the platform (for example, from the patient specimen), the methods and systems may be used to further evaluate genetic sequencing data derived from an organoid and/or the organoid sensitivity, especially to therapies matched based on a portion or all of the information determined by the systems and methods, including predicted cancer type(s), likely tumor origin(s), etc. These therapies may be tested on the organoid, derivatives of that organoid, and/or similar organoids to determine an organoid's sensitivity to those therapies. Any of the results may be included in a report. If the organoid is associated with a patient specimen, any of the results may be included in a report associated with that patient and/or delivered to the patient or patient's physician or clinician. In various examples, organoids may be cultured and tested according to the systems and methods disclosed in U.S. Patent Publication No. 2021/0155989, titled "Tumor Organoid Culture Compositions, Systems, and Methods", published May 27, 2021; PCT/US20/56930, titled "Systems and Methods for Predicting Therapeutic Sensitivity", filed Oct. 22, 2020; U.S. Patent Publication No. 2021/0172931, titled "Large Scale Organoid Analysis", published Jun. 10, 2021; PCT/US2020/063619, titled "Systems and Methods for High Throughput Drug Screening", filed Dec. 7, 2020 and U.S. patent application Ser. No. 17/301,975, titled "Artificial Fluorescent Image Systems and Methods", filed Apr. 20, 2021 which are each incorporated herein by reference and in their entirety for all purposes. In one example, the drug sensitivity assays may be especially informative if the systems and methods return results that match with a variety of therapies, or multiple results (for example, multiple equally or similarly likely cancer types or tumor origins), each matching with at least one therapy.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Patent Publication No. 2021/0118559, titled "Artificial Intelligence Assisted Precision Medicine Enhancements to Standardized Laboratory Diagnostic Testing", and published Apr. 22, 2021, which is incorporated herein by reference and in its entirety for all purposes.

It should be understood that the examples given above are illustrative and do not limit the uses of the systems and methods described herein in combination with a digital and laboratory health care platform.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method comprising:
(A) performing RNA sequencing on a sample of a cancer from a subject to provide RNA sequence data;

at a computer system having one or more processors, and memory storing one or more programs for execution by the one or more processors:
(B) processing the RNA sequence data to provide expression level data for at least 10 signature genes selected from the group consisting of CCL5, GZMA, NKG7, CCL4, GZMH, CST7, GZMB, GZMK, GNLY, PRF1, CCL4L2, CD52, IL32, CD74, CRIP1, CCL3, ITM2C, S100A10, TUBA4A, FGFBP2, S100A4, EOMES, HOPX, DUSP4, PLEK, S100A11, LGALS1, CTSC, ZNF683, SRRT, CLEC2B, LDHA, ENC1, OASL, ZEB2, HSPE1, GIMAP4, PTMS, GIMAP7, TNFSF9, ISG20, CCL3L1, PKM, CXCR3, SLA, XCL2, RNF213, SLAMF7, FABP5, FCRL6, ITM2A, SYTL3, TXNIP, TYROBP, RPS27L, H2AFZ, ITGA1, XCL1, RGCC, CACYBP, LYST, GGA2, ID2, PTPN7, MT2A, TGFB1, HAVCR2, ISG15, GBP5, KRT86, MAP3K8, SYNE1, SLC7A5, ARHGAP30, HSPH1, CORO1B, KIAA1551, PARP8, THEMIS, MYO1F, FKBP4, CTSW, IFNG, LAG3, ABI3, KLRD1, S1PR5, RGS1, LGALS3, KLRG1, TRAT1, SAMSN1, CRTAM, DUSP2, CXCR6, DNAJA1, PDCD1, TBX21, FASLG, and CD70, wherein the at least 10 signature genes comprises CCL5, granzyme A, NKG7, CCL4, granzyme B, granzyme H, granulysin, CCL4L2, and perforin 1;
(C) inputting the expression levels of the at least 10 signature genes to one or more models that are collectively trained to identify subjects as not likely to experience a progression event while being treated with an immune checkpoint inhibitor (ICI) therapy; and
(D) identifying the subject as not likely to experience a progression event while being treated with the ICI therapy; and
(E) administering the ICI therapy to the subject identified as not likely to experience a progression event while being treated with the ICI therapy.

2. The method of claim 1, wherein the one or more models are collectively trained to provide a cytotoxic (CT) score.

3. The method of claim 1, wherein the one or more models are collectively trained to provide a tumor mutation burden (TMB) for the subject's cancer wherein the TMB is determined based on an analysis of a mutation status for the one or more genes in the subject's cancer, and wherein the one or more genes is selected from ABCB1, ABCC3, ABL1, ABL2, FAM175A, ACTA2, ACVR1, ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf34, CALR, CARD11, CARM1, CASP8, CASR, CBFB, CBL, CBLB, CBLC, CBR3, CCDC6, CCND1, CCND2, CCND3, CCNE1, CD19, CD22, CD274, CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYNC2H1, EBF1, ECT2L, EGF, EGFR, EGLN1, EIF1AX, ELF3, TCEB1, C11orf30, ENG, EP300, EPCAM, EPHA2, EPHA7, EPHB1, EPHB2, EPOR, ERBB2, ERBB3, ERBB4, ERCC1, ERCC2, ERCC3, ERCC4, ERCC5, ERCC6, ERG, ERRFI1, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANCI, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOXP1, FOXQ1, FRS2, FUBP1, FUS, G6PD, GABRA6, GALNT12, GATA1, GATA2, GATA3, GATA4, GATA6, GEN1, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HISTIHIE, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDO1, IFIT1, IFIT2, IFIT3, IFNAR1, IFNAR2, IFNGR1, IFNGR2, IFNL3, IKBKE, IKZF1, IL1ORA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEF1, LMNA, LMO1, LRP1B, LYN, LZTR1, MAD2L2, MAF, MAFB, MAGI2, MALT1, MAP2K1, MAP2K2, MAP2K4, MAP3K1, MAP3K7, MAPK1, MAX, MCIR, MCL1, MDM2, MDM4, MED12, MEF2B, MEN1, MET, MGMT, MIB1, MITF, MKI67, MLH1, MLH3, MLLT3, MN1, MPL, MRE11A, MS4A1, MSH2, MSH3, MSH6, MTAP, MTHFD2, MTHFR, MTOR, MTRR, MUTYH, MYB, MYC, MYCL, MYCN, MYD88, MYH11, NBN, NCOR1, NCOR2, NF1, NF2, NFE2L2, NFKBIA, NHP2, NKX2-1, NOP10, NOTCH1, NOTCH2, NOTCH3, NOTCH4, NPM1, NQO1, NRAS, NRG1, NSD1, WHSC1, NT5C2, NTHL1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCDILG2, PDGFRA, PDG-FRB, PDK1, PHF6, PHGDH, PHLPP1, PHLPP2, PHOX2B, PIAS4, PIK3C2B, PIK3CA, PIK3CB, PIK3CD, PIK3CG, PIK3R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2RIA, PPP2R2A, PPP6C, PRCC, PRDM1, PREX2, PRKAR1A, PRKDC, PARK2, PRSS1, PTCH1, PTCH2, PTEN, PTPN11, PTPN13, PTPN22, PTPRD, PTPRT, QKI, RAC1, RAD21, RAD50, RAD51, RAD51B, RAD51C, RAD51D, RAD54L, RAF1, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNXIT1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SMAD2, SMAD3, SMAD4, SMARCA1, SMARCA4, SMARCB1, SMARCE1, SMCIA, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STAT6, STK11, SUFU, SUZ12, SYK, SYNE1, TAF1, TANC1, TAP1, TAP2, TARBP2, TBC1D12, TBL1XR1, TBX3, TCF3, TCF7L2, TCL1A, TERT, TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, C10orf54, WEE1, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, and ZRSR2.

4. The method of claim 1, wherein at least one of the one or more models generate an IO Progression Risk Score.

5. The method of claim 4, wherein the IO Progression Risk Score reflects the probability of a progression event occurring in 3 months.

6. The method of claim 4, wherein the IO Progression Risk Score reflects the probability of a progression event occurring in 6 months.

7. The method of claim 1, wherein the subject's cancer is stage IV.

8. The method of claim 1, wherein the subject's cancer is non-small cell lung carcinoma (NSCLC).

9. The method of claim 1, wherein the subject's cancer is stage IV NSCLC, or non-stage IV NSCLC with a metastasis event.

10. The method of claim 1, wherein the subject's cancer is stage IV, or is earlier than stage IV with a metastasis event and no prior treatment with immune-oncology (IO) therapy.

11. The method of claim 1, wherein at least one of the one or more models calculates a CT score, at least one of the one or more models calculates a TMB, and at least one of the one or more models calculates an IO Progression risk score.

12. The method of claim 11, wherein the IO Progression Risk score is calculated based on the CT score and the TMB.

13. The method of claim 1, wherein the subject's cancer has a tumor mutational burden (TMB) below a TMB threshold.

14. The method of claim 1, wherein the at least 10 signature genes comprise NKG7, CCL5, GZMA, CCL4, CST7, GZMH, GZMB, GZMK, PRF1, GNLY, CCL4L2, CD74, IL32, CD52, CCL3, LAG3, CTSW, CTSC, CXCR6, ABI3, S100A4.

* * * * *